US010292719B2

(12) United States Patent
Burger et al.

(10) Patent No.: US 10,292,719 B2
(45) Date of Patent: May 21, 2019

(54) STEERABLE CURVABLE VERTEBROPLASTY DRILL

(71) Applicant: Merit Medical Systems, Inc., South Jordan, UT (US)

(72) Inventors: Keith Burger, San Francisco, CA (US); Joshua Cheatwood, Windsor, CA (US); Shixin Chen, Santa Rosa, CA (US)

(73) Assignee: Merit Medical Systems, Inc., South Jordan, UT (US)

( * ) Notice: Subject to any disclaimer, the term of this patent is extended or adjusted under 35 U.S.C. 154(b) by 211 days.

(21) Appl. No.: 14/139,372

(22) Filed: Dec. 23, 2013

(65) Prior Publication Data

US 2014/0316413 A1 Oct. 23, 2014

Related U.S. Application Data

(63) Continuation of application No. 13/215,098, filed on Aug. 22, 2011, now abandoned, which is a
(Continued)

(51) Int. Cl.
*A61B 17/16* (2006.01)
*A61B 17/88* (2006.01)
*A61B 17/00* (2006.01)

(52) U.S. Cl.
CPC ...... *A61B 17/1671* (2013.01); *A61B 17/1642* (2013.01); *A61B 17/8811* (2013.01);
(Continued)

(58) Field of Classification Search
CPC ............ A61B 17/1642; A61B 17/1671; A61B 17/8808; A61B 2017/00327
See application file for complete search history.

(56) References Cited

U.S. PATENT DOCUMENTS 6,106,539 A * 8/2000 Fortier ............... A61B 17/3417
604/164.06
6,408,889 B1 * 6/2002 Komachi ............. A61B 1/0055
138/120
(Continued)

OTHER PUBLICATIONS

International Search Report and Written Opinion dated Jul. 20, 2010 for PCT/US2010/035687.
Office Action dated Jun. 20, 2013 for U.S. Appl. No. 13/215,098.

*Primary Examiner* — Samuel S Hanna
(74) *Attorney, Agent, or Firm* — Stoel Rives LLP

(57) ABSTRACT

Disclosed herein is a steerable and curvable drill that can be used for various applications including vertebroplasty. The drill can include an elongate, tubular body, having a proximal end, a distal end, and a central lumen extending therethrough; a deflectable zone on the distal end of the tubular body including one or more laser cuts, deflectable through an angular range; an insertable wire insertable into at least a portion of the central lumen of the elongate, tubular body; a handle on the proximal end of the tubular body; a deflection control on the handle; a drill control on the handle; a drive shaft within the elongate tubular body having a proximal end and a distal end; and a boring element on the distal end of the device for creating a cavity within bone. The boring element can be operably connected to the distal end of the drive shaft via a crimping mechanism. Systems and methods involving the drill are also disclosed.

13 Claims, 41 Drawing Sheets

Related U.S. Application Data continuation of application No. 12/983,771, filed on Jan. 3, 2011, now abandoned, which is a continuation of application No. 12/784,422, filed on May 20, 2010, now abandoned, which is a continuation-in-part of application No. 12/469,611, filed on May 20, 2009, now abandoned.

(52) U.S. Cl.
CPC ...... *A61B 17/8819* (2013.01); *A61B 17/8855* (2013.01); *A61B 17/8827* (2013.01); *A61B 2017/00557* (2013.01)

(56) References Cited

U.S. PATENT DOCUMENTS

| | | | |
|---|---|---|---|
| 6,740,090 B1 | 5/2004 | Cragg et al. | |
| 7,004,930 B2 | 2/2006 | Marshall | |
| RE44,883 E * | 5/2014 | Cha | A61B 17/1671 606/80 |
| 2004/0220577 A1* | 11/2004 | Cragg | A61B 17/1617 606/80 |
| 2005/0177168 A1 | 8/2005 | Brunnett et al. | |
| 2006/0084977 A1* | 4/2006 | Lieberman | A61B 17/1757 606/60 |
| 2006/0229625 A1 | 10/2006 | Truckai et al. | |
| 2007/0055260 A1 | 3/2007 | Cragg | |
| 2007/0093840 A1* | 4/2007 | Pacelli | A61B 17/1631 606/80 |
| 2008/0249481 A1 | 10/2008 | Crainich et al. | |
| 2009/0131948 A1* | 5/2009 | Liu | A61B 17/8811 606/93 |

* cited by examiner

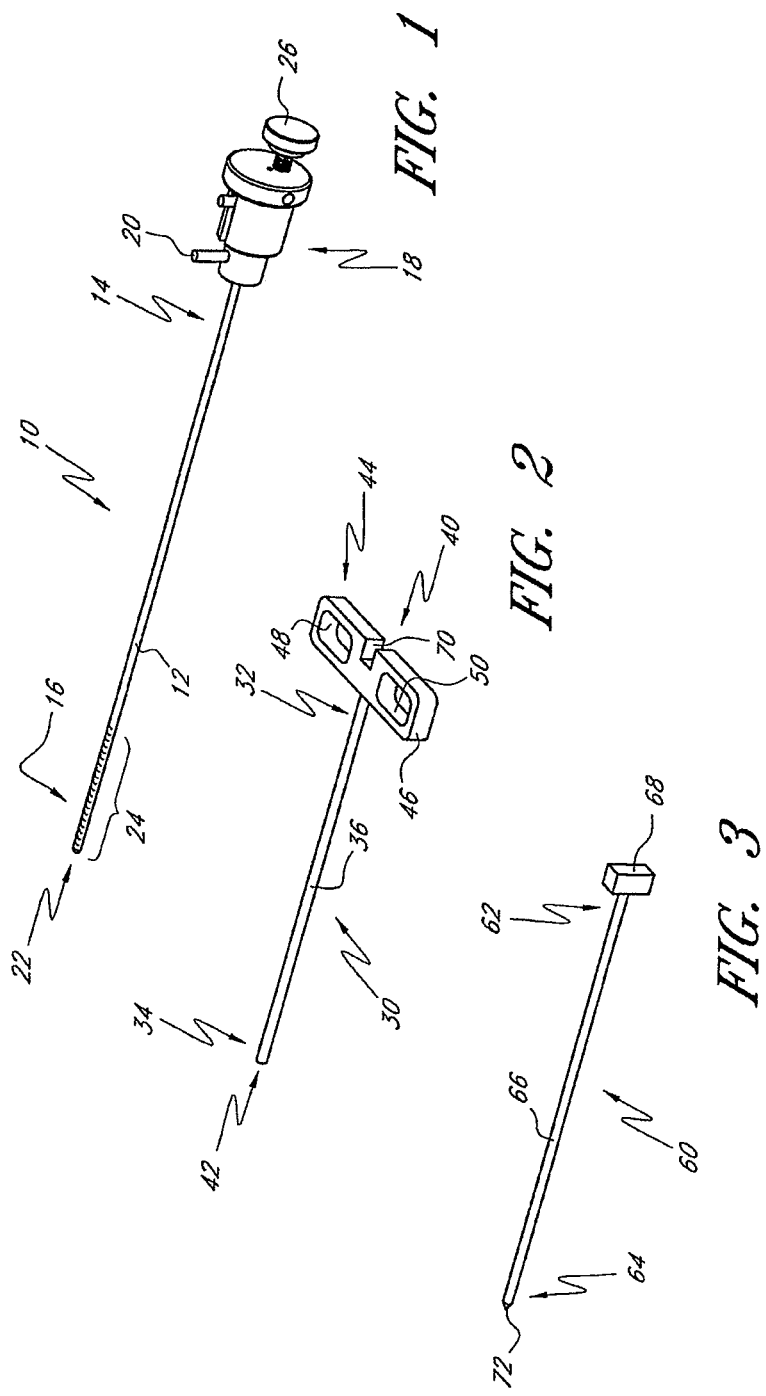

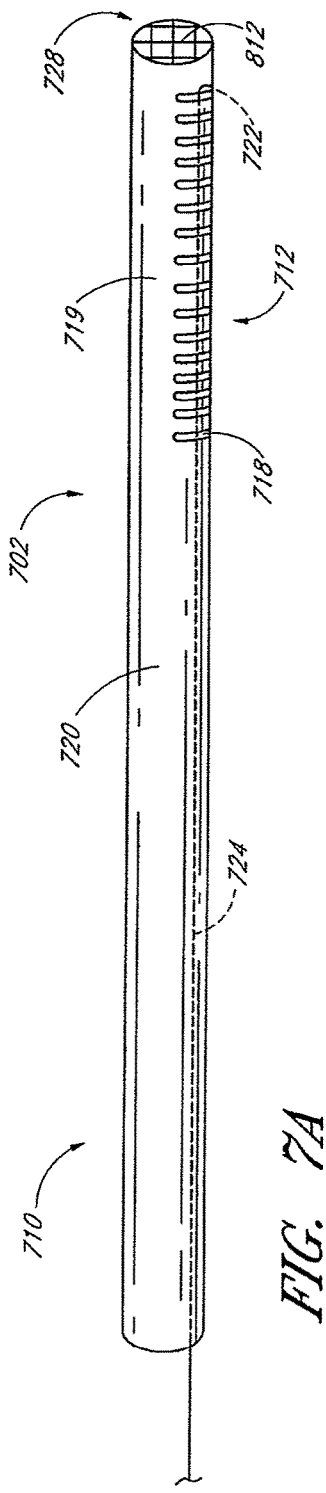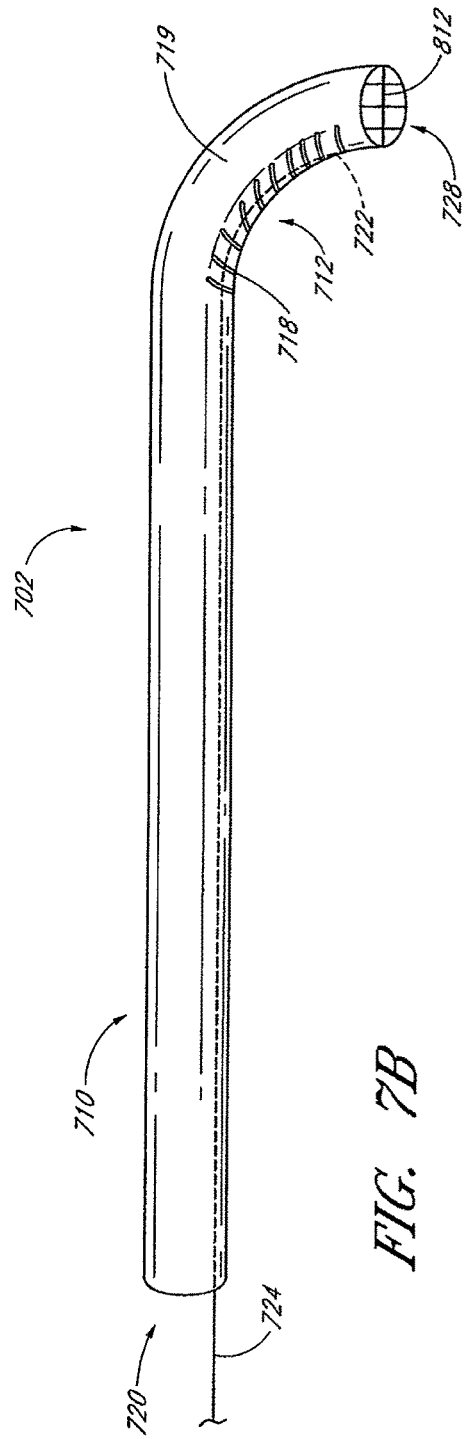
FIG. 7A
FIG. 7B

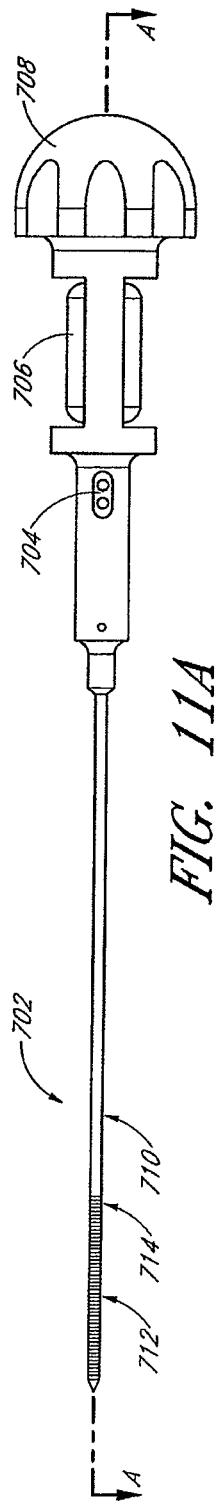
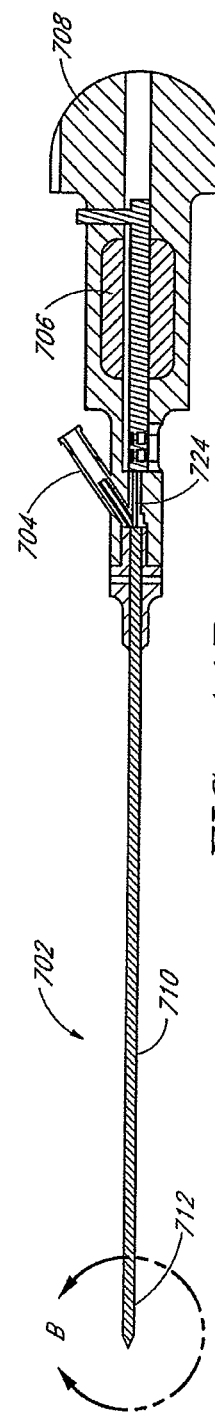
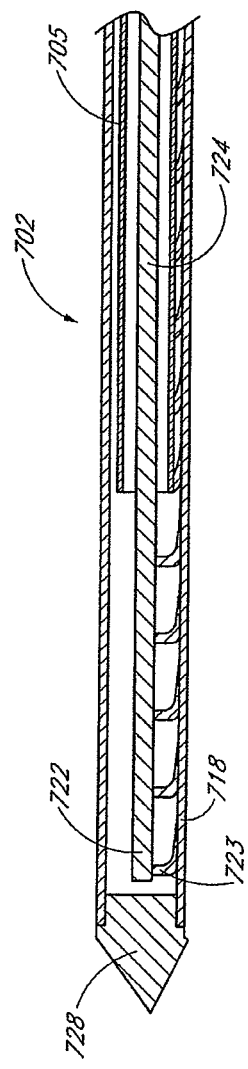
FIG. 11A
FIG. 11B
FIG. 11C

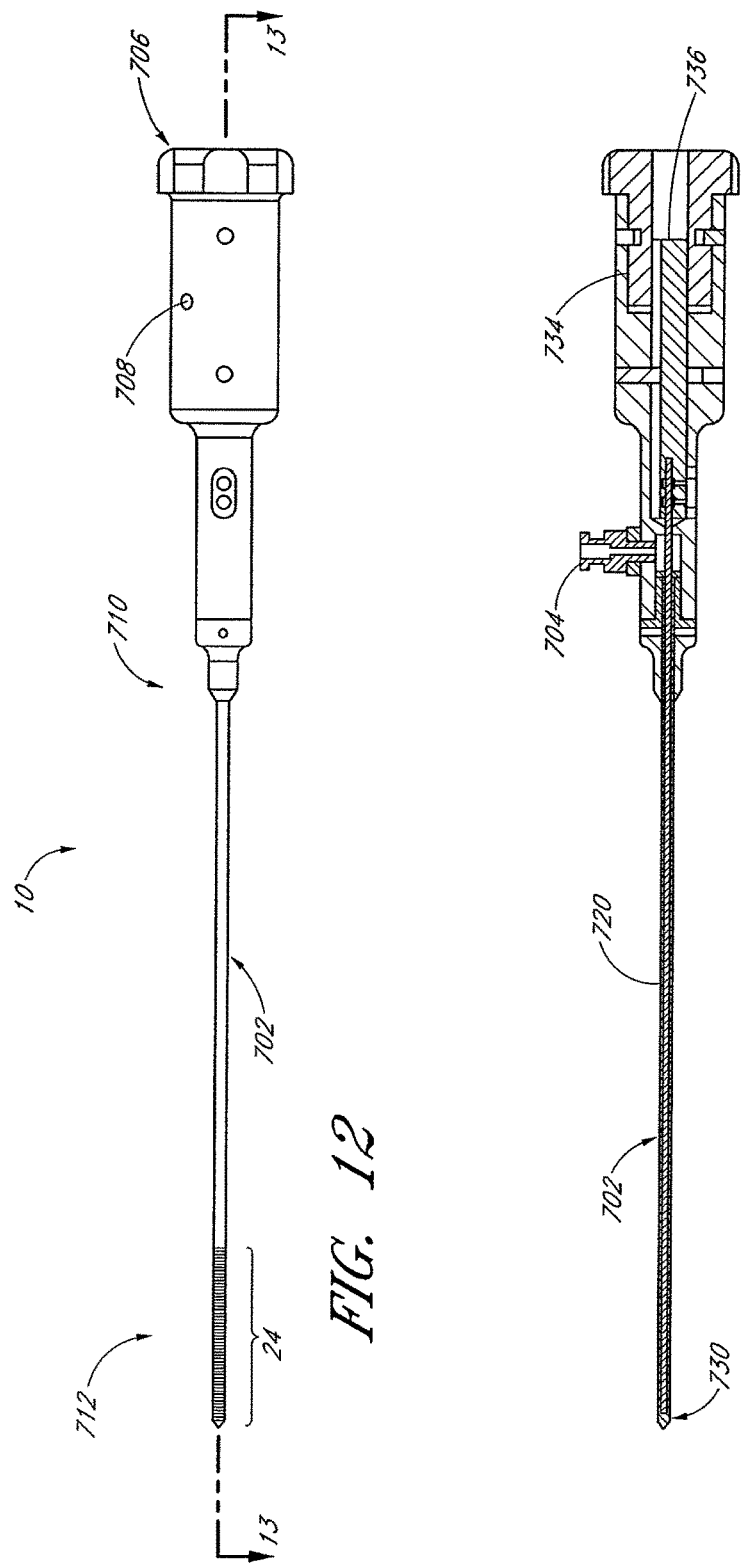

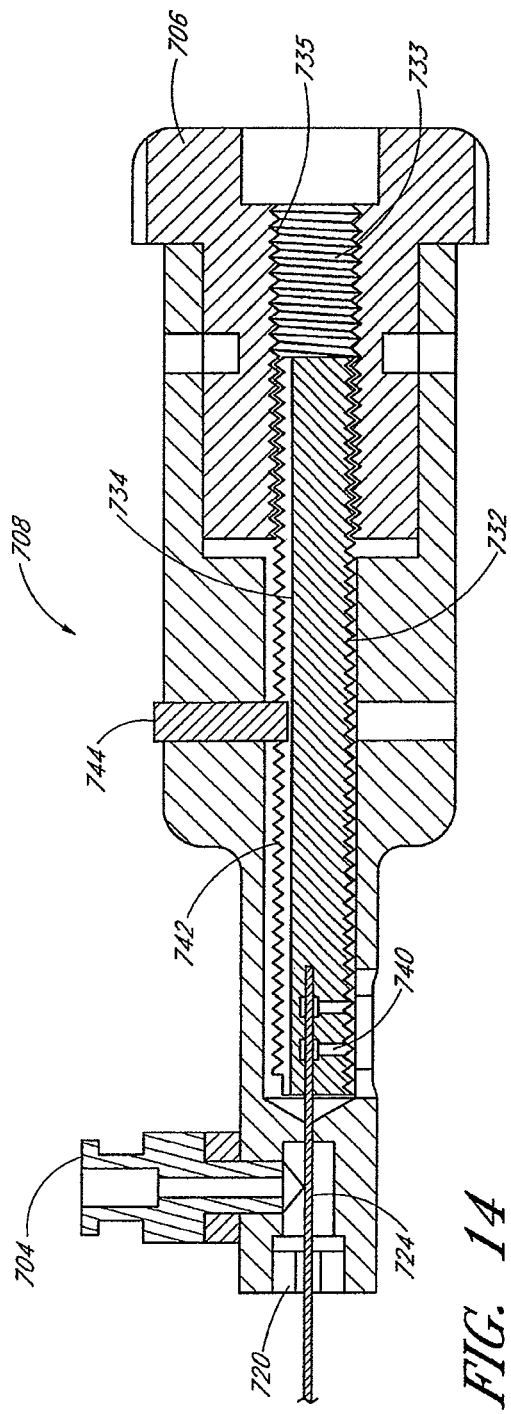
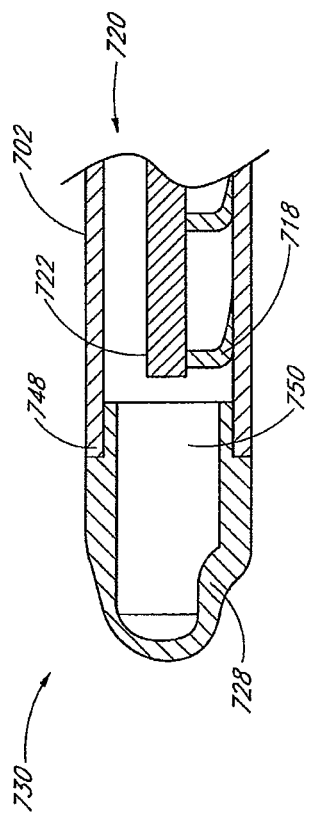
FIG. 14
FIG. 15

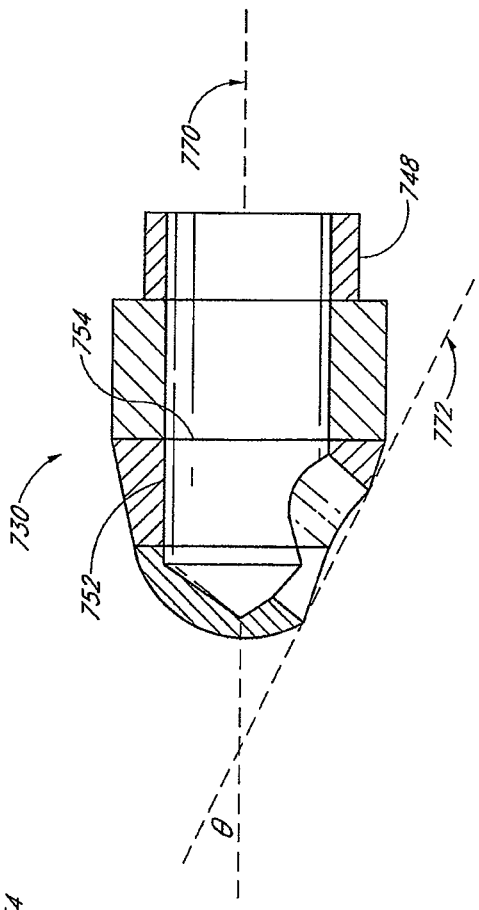
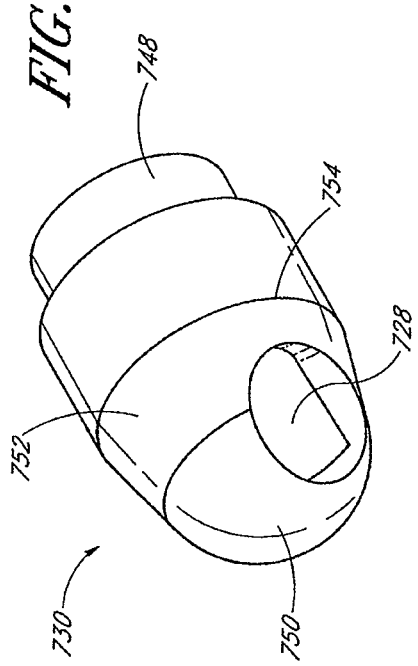
FIG. 15A
FIG. 15B

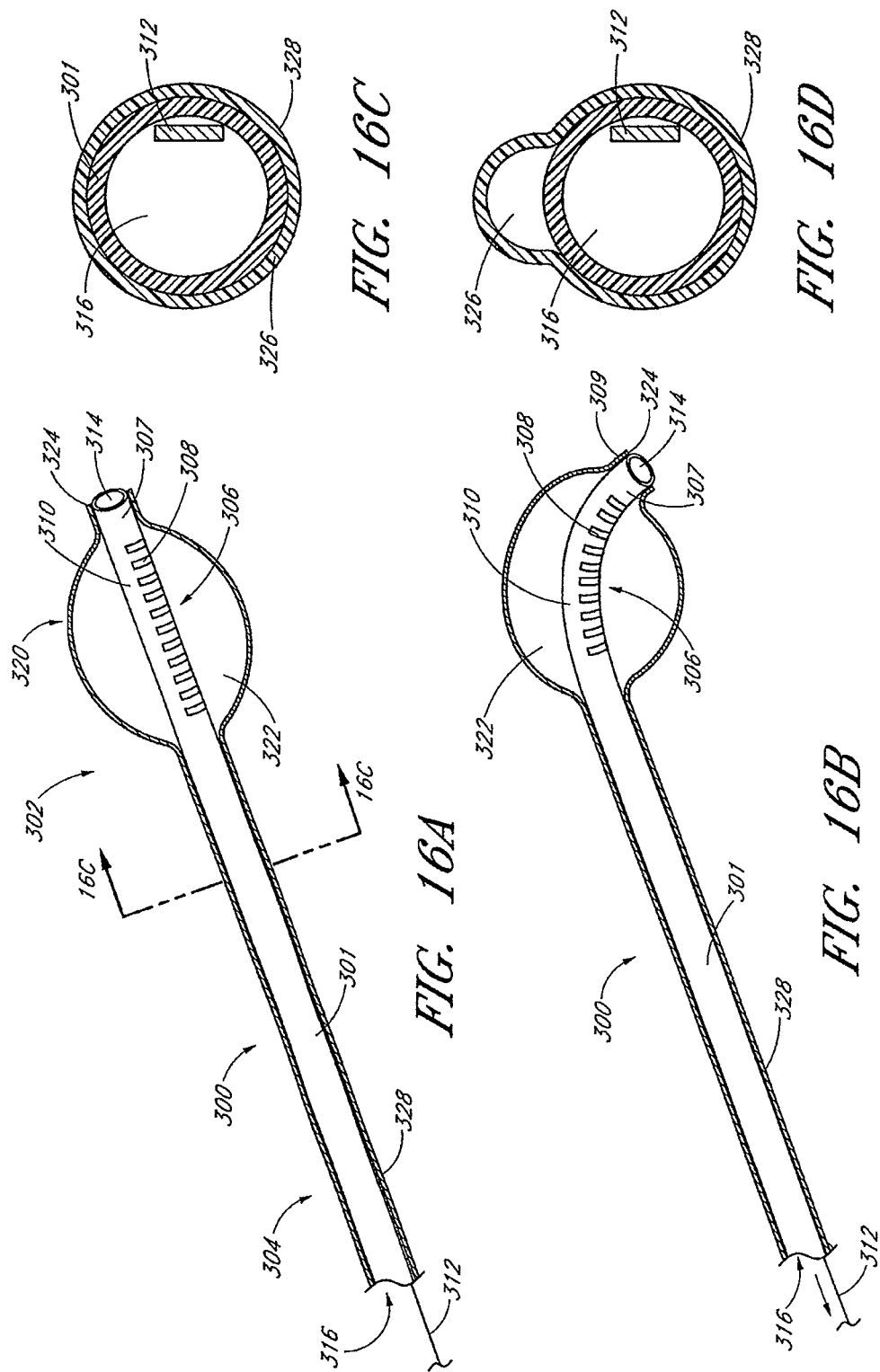

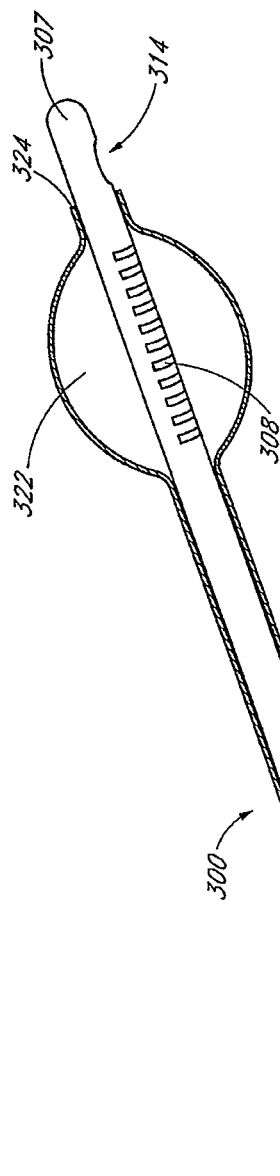
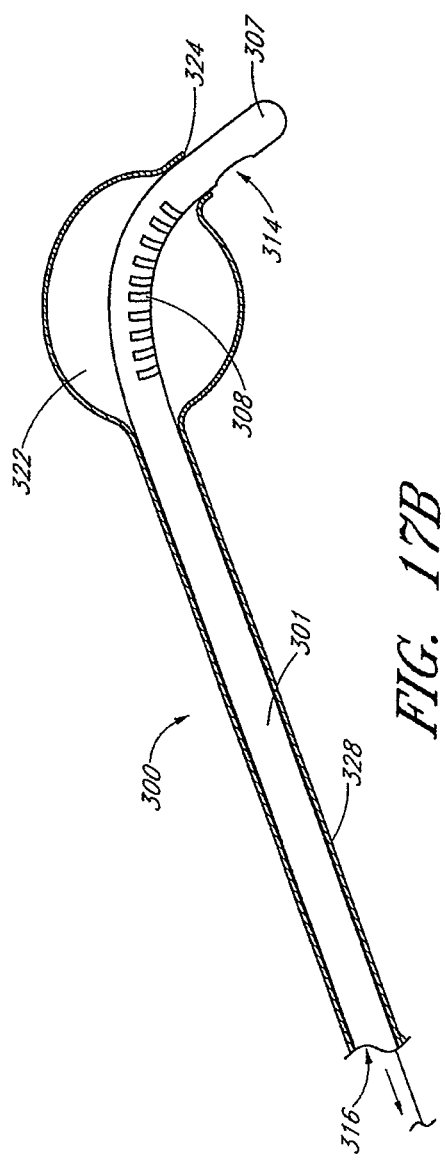
FIG. 17A
FIG. 17B

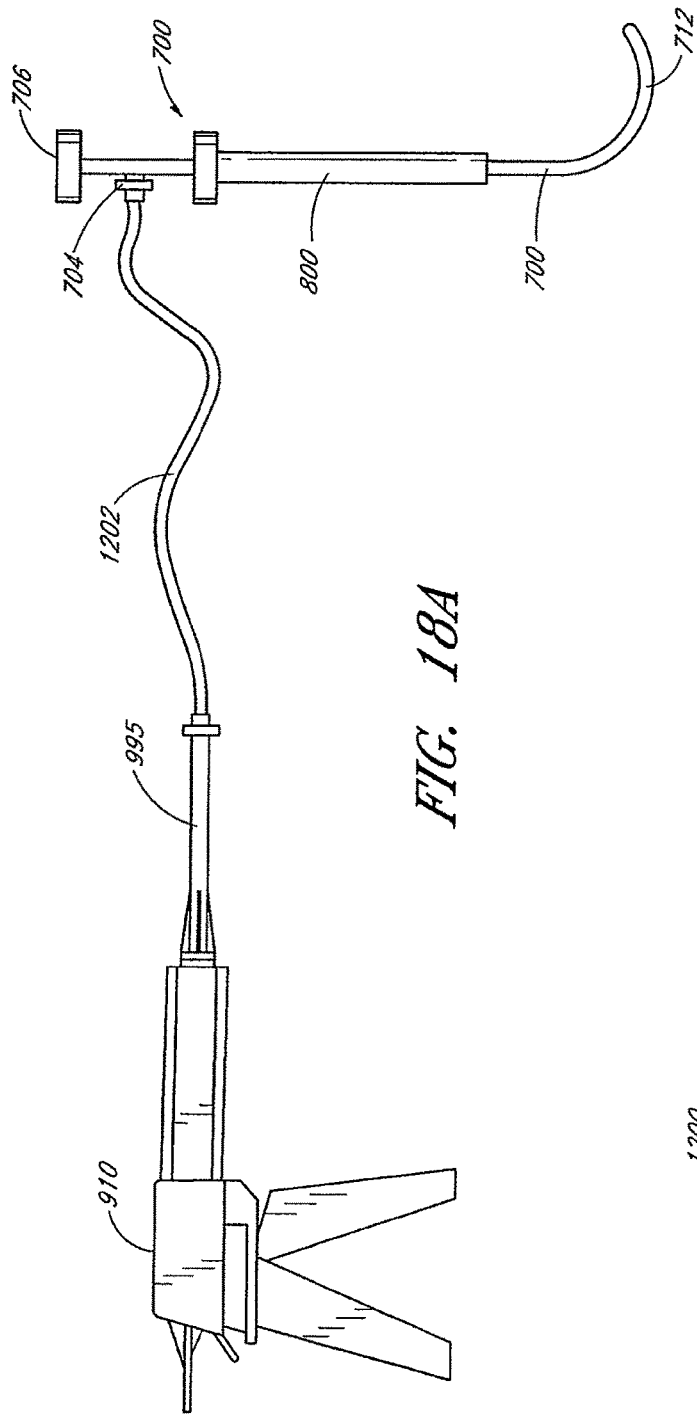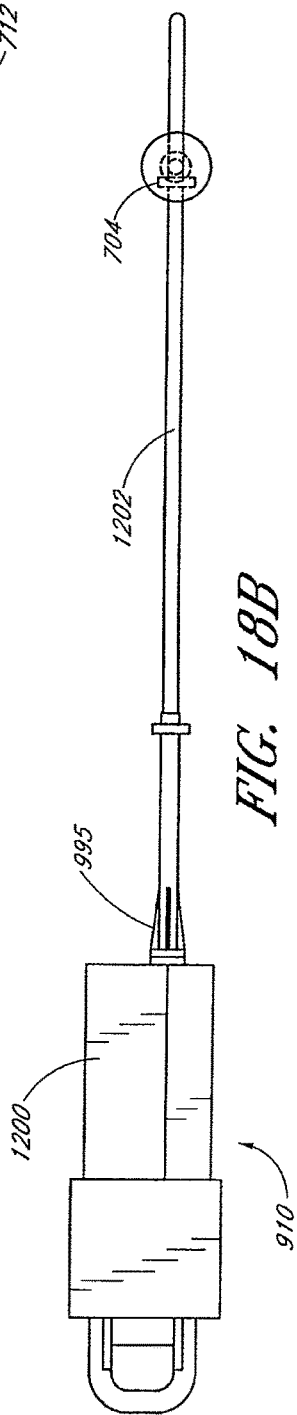
FIG. 18A
FIG. 18B

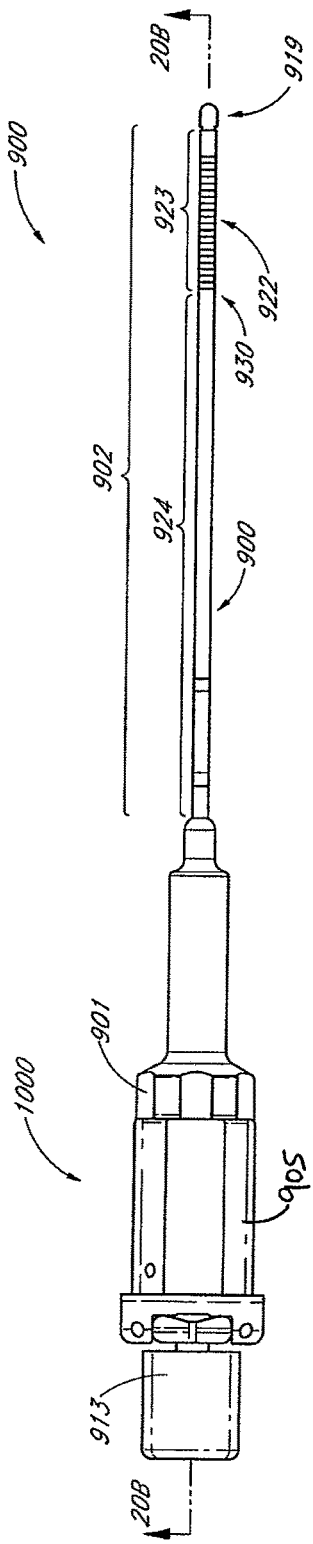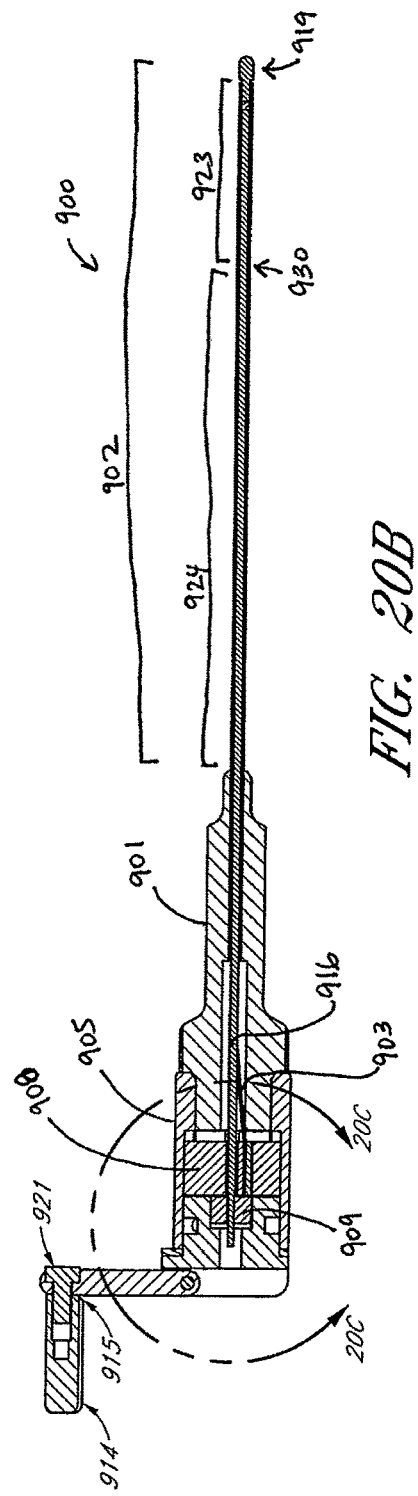
FIG. 20A
FIG. 20B

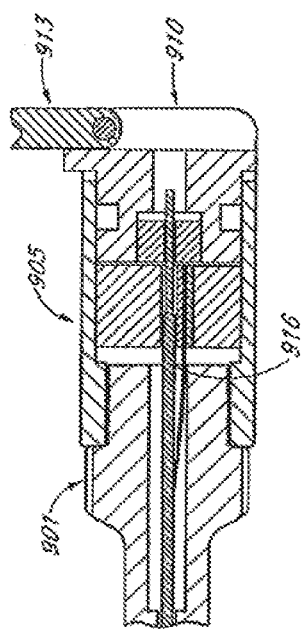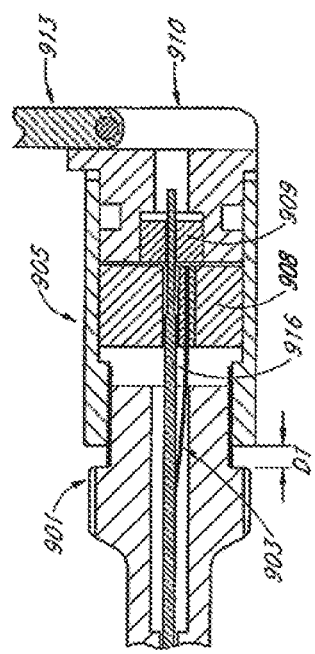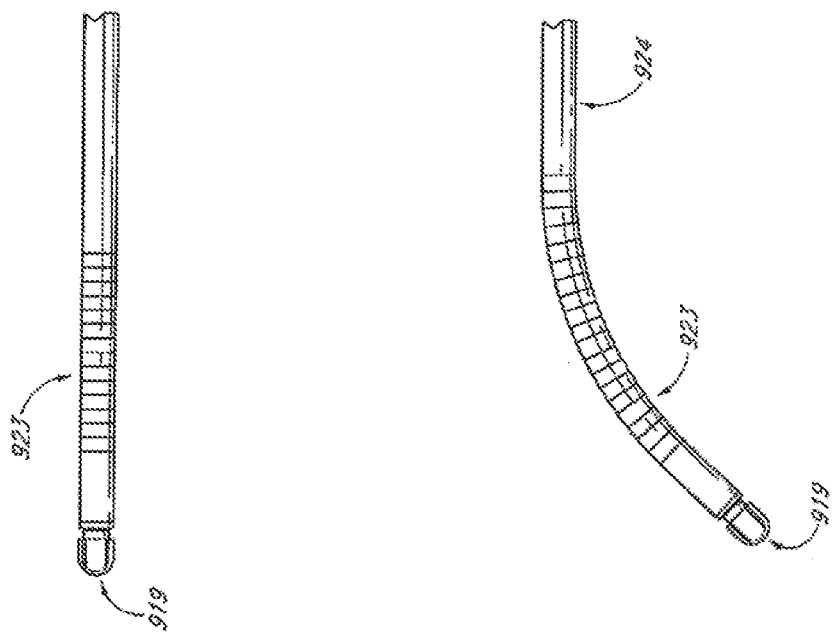

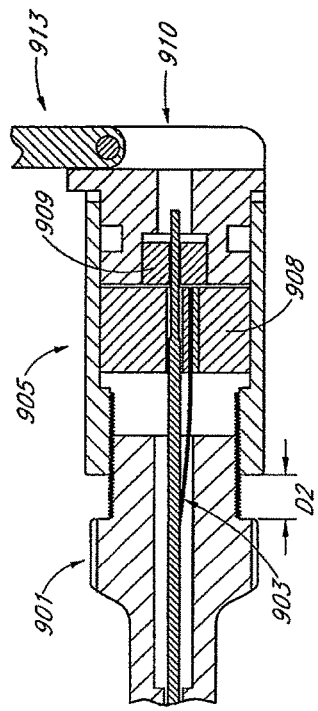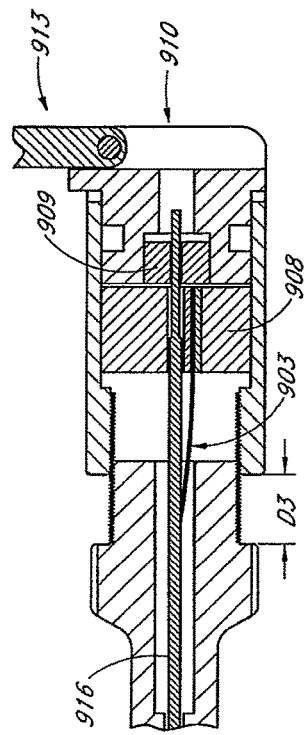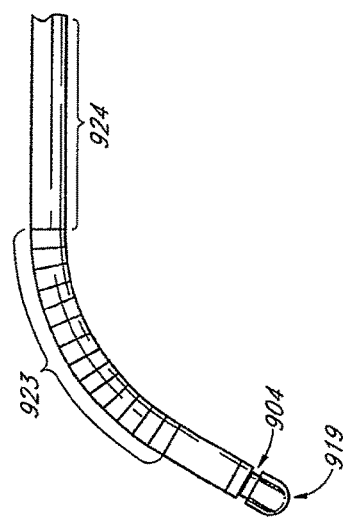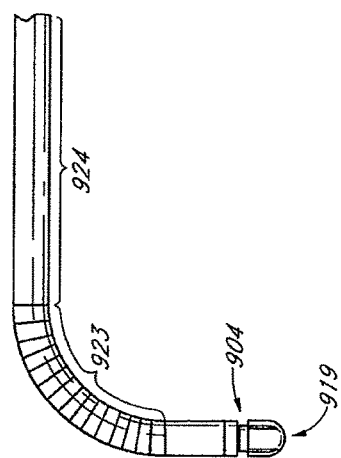
FIG. 21C
FIG. 21D

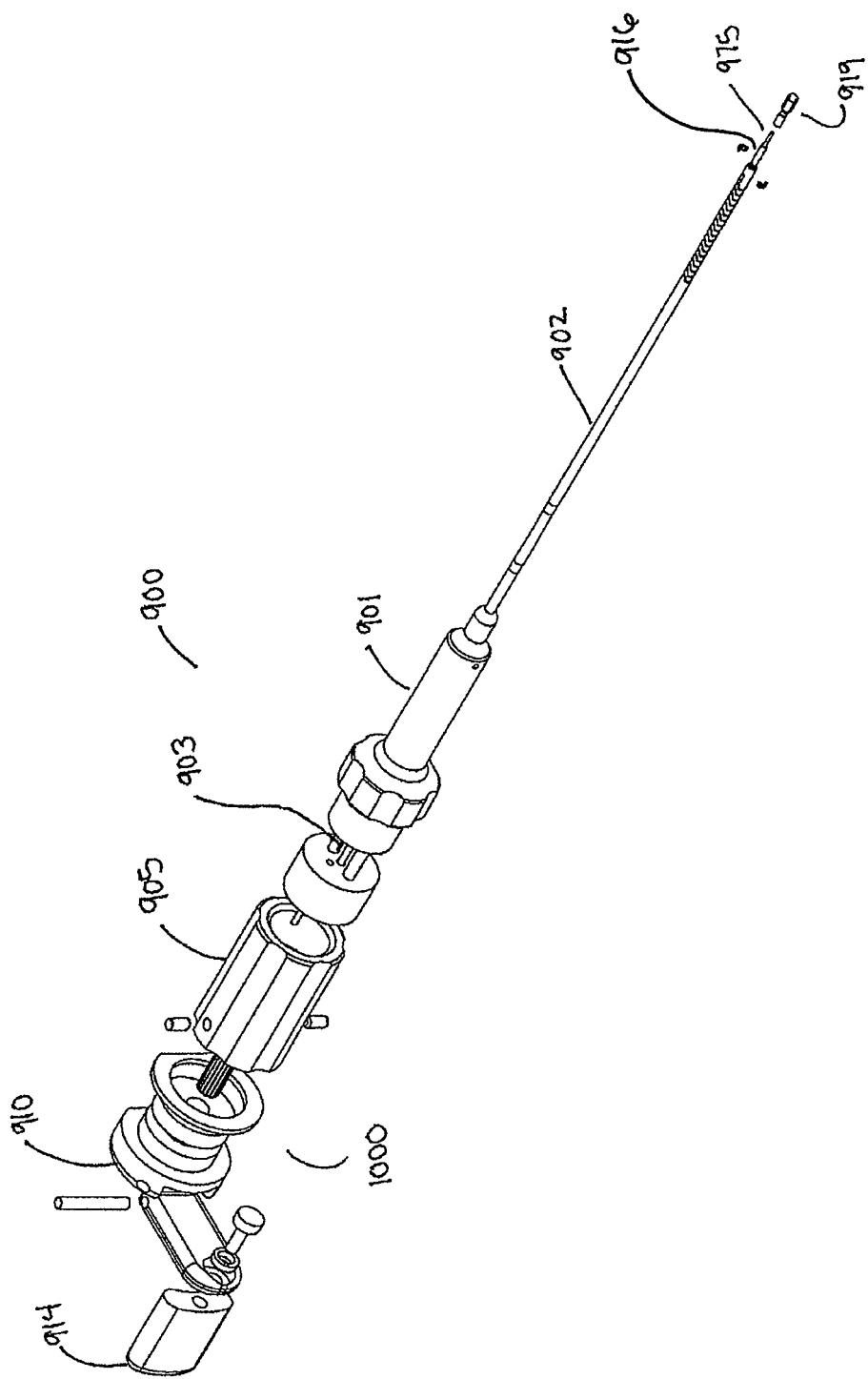

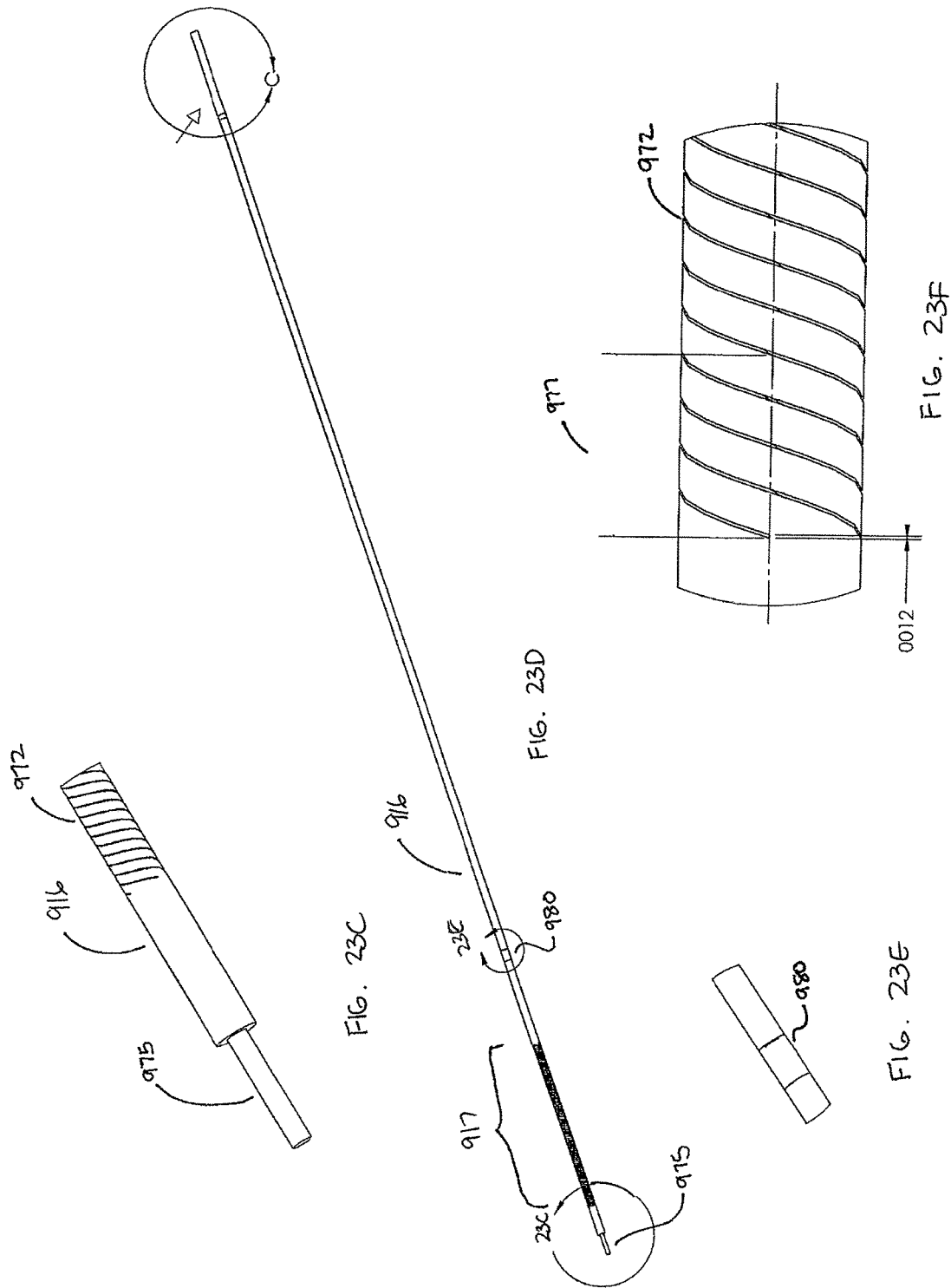

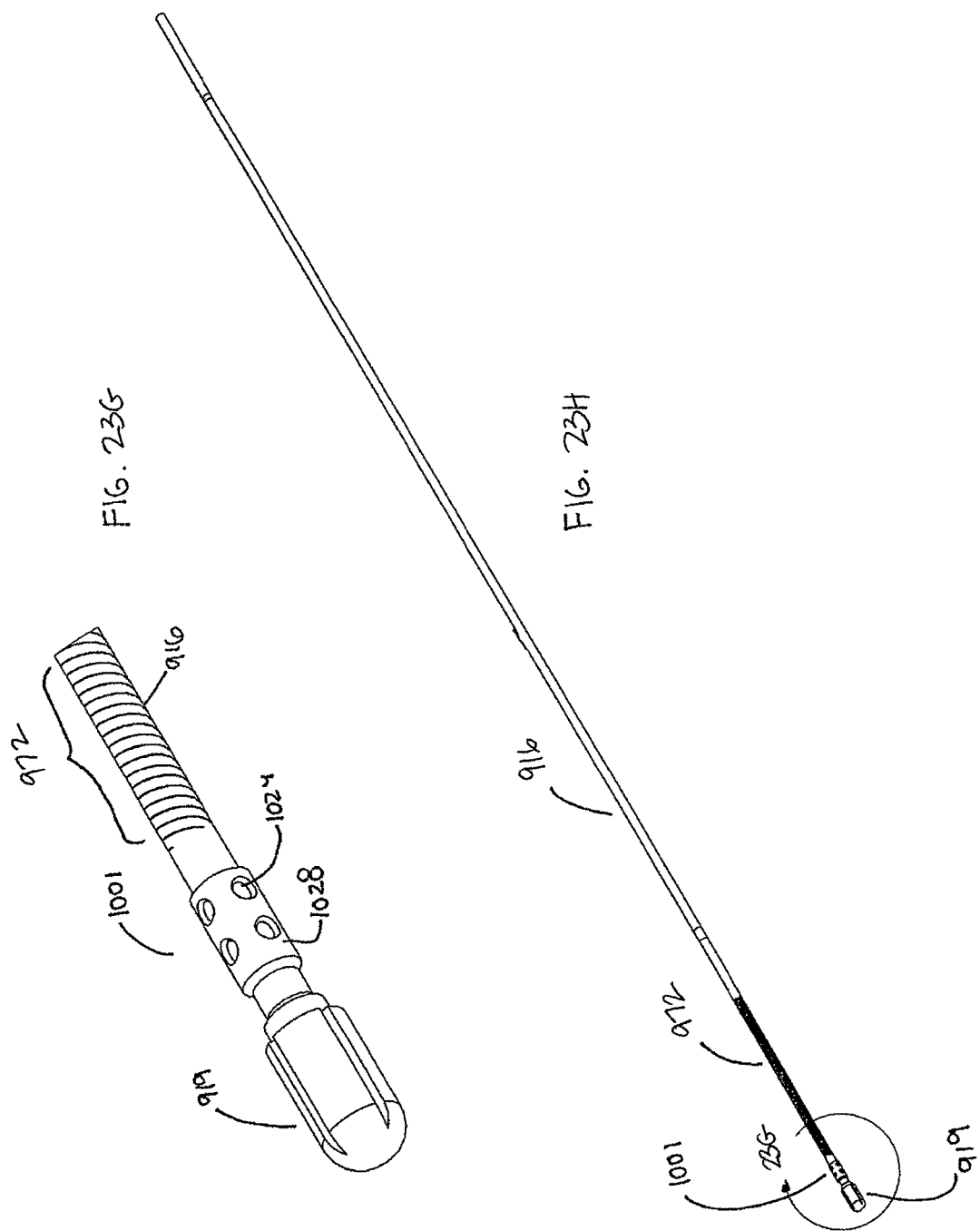

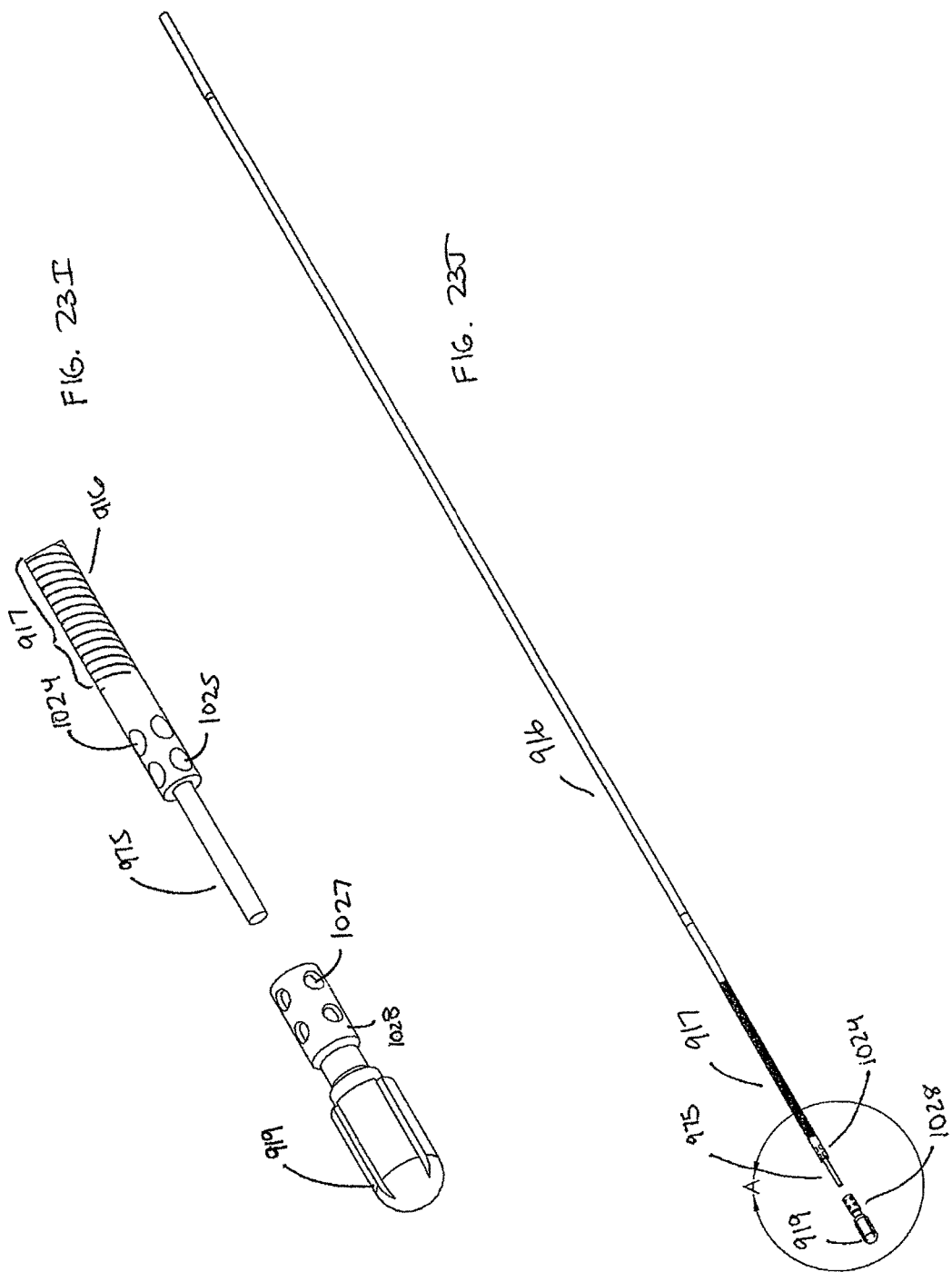

STEERABLE CURVABLE VERTEBROPLASTY DRILL

PRIORITY CLAIM

This application claims priority under 35 U.S.C. § 120 as a continuation application of U.S. application Ser. No. 13/215,098 filed Aug. 22, 2011, which is a continuation application of U.S. patent application Ser. No. 12/983,771 filed on Jan. 3, 2011, which is in turn a continuation application of U.S. patent application Ser. No. 12/784,422 filed on May 20, 2010, which is a continuation-in-part of U.S. patent application Ser. No. 12/469,611 filed on May 20, 2009. All of the aforementioned priority applications are hereby incorporated by reference in their entireties.

BACKGROUND OF THE INVENTION

According to the National Osteoporosis Foundation ten million Americans have osteoporosis, and an estimated 34 million with low bone mass are at risk of developing osteoporosis (http://www.nof.org/osteoporosis/diseasefacts.htm). Called the "silent disease," OSP develops slowly over a number of years without symptoms. Eighty percent of those affected are women, particularly petite Caucasian and Asian women, although older men and women of all races and ethnicities are at significant risk.

In the United States, 700,000 people are diagnosed with vertebral compression fractures as a result of OSP each year. Morbidity associated with vertebral fractures includes severe back pain, loss of height and deformity, all of which negatively affect quality of life.

Once microfracture of the vertebra begins, there is little the clinician can do except palliative medical treatment using analgesics, bed rest and/or restriction of activity. With time, the microfractures widen at one level and without surgical intervention, the fractures cascade downward with increasing kyphosis or "hunching" of the back. Once a mechanical lesion develops, surgery is the only option. Vertebroplasty or kyphoplasty are the primary minimally-invasive surgical procedures performed for the treatment of compression-wedge fractures due to OSP.

Vertebroplasty stabilizes the collapsed vertebra by injecting polymethylmethacrylate (PMMA) or a substantially equivalent bone cement into cancellous bone space of the vertebrae. Besides providing structural support to the vertebra, the exothermic reaction of PMMA polymerization is said to kill off the nociceptors or pain receptors in the bone, although no proof of this hypothesis has been provided in the literature. This procedure is typically performed as an out-patient procedure and requires only a short-acting local or general anesthetic. Once the surgical area of the spine is anesthetized, the physician inserts one or two needles through small skin incisions into either the pedicle (uni-transpedicular) or the pedicles of the vertebral body i.e., bi-transpedicular. PMMA is injected through the needle and into the cancellous-bone space of the vertebra.

Kyphoplasty mirrors the vertebroplasty procedure but has the additional step of inserting and expanding a nylon balloon in the interior of the vertebral body. Expansion of the balloon under pressure reduces the compression fracture and creates a cavity. After withdrawal of the balloon, PMMA is injected into the cavity to stabilize the reduction. The kyphoplasty procedure may restore the vertebral body height. Kyphoplasty is an in-patient surgery that requires hospitalization and a general anesthetic. Kyphon Inc. claims over 275,000 spinal fractures have been treated using their PMMA derivative and their "balloon" kyphoplasty procedure worldwide (Sunnyvale, Calif., Sep. 5, 2006, (PR NEWSWIRE) Kyphon study 2006).

Bone cement for both vertebroplasty and kyphoplasty procedures currently employ variations of standard PMMA in a powder and a methyl methacrylate monomer liquid. When the powder and liquid monomer are mixed, an exothermic polymerization takes place resulting in the formation of a "dough-like" material, which is then inserted into the cancellous bone space. The dough, when hardened, becomes either the reinforcing structure or the grout between the bone and prosthesis.

The average clinical in vivo life of the PMMA grout is approximately 10 years due to corrosion fatigue of either the bone-cement/prosthesis and/or the bone cement/bone interfaces. Jasty et al. (1991) showed that in cemented total hip replacements: "Fractures in the cement mantle itself were found on cut sections around all prostheses which had been in use for over three years." Jasty et al. also noted: "In general, specimens less than 10 years in situ showed small incomplete fractures while the specimens in place more than 10 years all showed large complete cement mantle fractures."

When an implant fails, a revision becomes mandatory. After removal of the cement and hardware, a cemented arthroplasty can be repeated if enough cancellous bone matrix exists to grip the new PMMA. Alternatively, cement-less prosthesis can be installed. Such a revision, however, can only be applied to total joint replacement failures. For vertebroplasty and/or kyphoplasty, a classical screw and plate internal fixation with autograft fusion is necessary.

Despite advances in the foregoing procedures, there remains a need for improved bone cement delivery systems which enable rapid and controllable deployment of bone cement for the treatment of conditions such as vertebral compression fractures.

SUMMARY OF THE INVENTION

Some embodiments of the present invention relate to a steerable and curvable vertebroplasty drill comprising a proximal handle and a distal elongate body. This distal elongate body is divided into a relatively rigid proximal portion that is coaxial with the handle, and a flexible distal portion capable of being deflected to an angle relative to the proximal portion. At the distal end of the device there is a boring element that can penetrate bone or other tissue. This boring element is turned by a drive shaft that is operably coupled to a knob, crank, or other device turned by the operator. Motorized steerable and curvable vertebroplasty drills are also within the scope of the invention.

In some embodiments, the operator can control the angle of deflection of the boring element, the distal end of the elongate body, and the portion of the drive shaft therein, relative to that of the proximal end of the elongate body and handle. The deflection of the distal end can be controlled by turning a portion of the handle that is threadably engaged with a second portion of the handle. The rotation of these two parts of the handle separates these components, thereby increasing the overall length of the handle as well as the overall length of the device itself. This increase in the length of the device increases the tension exerted by a pull wire that is proximally affixed near the proximal portion of the handle, and distally affixed near the distal end of the elongate body. As the tension exerted by this pull wire on the flexible distal end of the elongate body increases, the distal end can be deflected, and the angle of actuation of the boring element adjusted. In some embodiments, the distal end of the elongate body can passively return to a coaxial configuration relative to the proximal end of the elongate body when the tension on the pull wire is reduced by rotating the handle in the other direction and thereby reducing the overall length of the handle.

In some embodiments, the drive shaft is capable of a degree of axial motion so as to keep the drive shaft operably coupled with the crank, handle, motor or other source of power despite the changes in the length of the handle.

Within the scope of the present invention is a method of treating bone using the steerable and curvable vertebroplasty drill. In some embodiments, this method comprises the creation of a cavity in a vertebral body by creating an access channel, inserting an introducer cannula, inserting the steerable and curvable vertebroplasty drill through the cannula, and drilling through cancellous bone in the interior of the vertebral body. By changing the deflection angle of the distal end of the device, multiple cavities can be drilled at different angles from a single insertion site and angle of approach. The cavity thereby created can then be filled with bone cement or other compounds following the withdrawal of the device.

In some embodiments, the steerable and curvable vertebroplasty drill can be part of a vertebroplasty kit that further comprises devices to mix various bone cement compounds, devices to inject the bone cement into the bone cavity, devices to facilitate the insertion of the steerable and curvable vertebroplasty drill into the patient's body, and various other devices to facilitate the performance of surgical procedures involving the device herein disclosed.

In some embodiments, a steerable and curvable vertebroplasty drill is provided. The drill comprises an elongate tubular body having a proximal end, a distal end, and a central lumen extending therethrough; a handle on the proximal end of the tubular body, the handle comprising a deflection control for deflecting a deflectable zone on a distal end of the tubular body; and a drive shaft housed in the central lumen of the tubular body, the drive shaft including a distal portion comprising one or more slit apertures on the surface of the drive shaft. The slit apertures can be helical, or can comprise chevrons. An angular distance between the slit apertures can be 90 degrees. A pitch of the slit apertures can be between 0.055" and 0.075". The drill can further comprise an insertable wire insertable through a lumen of the drive shaft and configured to provide radial support to the distal portion of the drive shaft comprising one or more slits. The insertable wire can comprise Nitinol. The drive shaft can be configured to flex via the slit apertures upon flexing of the deflectable zone of the tubular body.

In some embodiments, a steerable and curvable vertebroplasty drill is provided. The drill comprises an elongate tubular body having a proximal end, a distal end and a central lumen extending therethrough; a first crimp member on the distal end of the tubular body; a boring member; and a second crimp member on the boring member, wherein the second crimp member is configured to be interlocking with the first crimp member to form a single continuous body between the tubular body and boring member. The elongate tubular body can comprise a drive shaft. The first crimp member can comprise a plurality of raised surfaces. The second crimp member can comprise a plurality of apertures for receiving the raised surfaces.

In some embodiments, a method of treating a bone is provided. The method comprises creating an access channel to access the interior of a vertebral body; inserting an introducer cannula into the access channel; inserting a steerable and curvable drill through the introducer cannula into the interior of the vertebral body, the steerable and curvable drill comprising an elongate body having a proximal end and a distal end, the distal end comprising a deflectable zone; rotating a control to deflect the deflectable zone of the steerable and curvable drill in the vertebral body; removing the steerable and curvable drill from the interior of the vertebral body; and flowing bone cement through an injection needle into the interior of the vertebral body.

BRIEF DESCRIPTION OF THE DRAWINGS

FIG. 1 is a perspective view of a steerable and curvable injection needle in accordance with one aspect of the present invention.

FIG. 2 is a perspective view of an introducer in accordance with one aspect of the present invention.

FIG. 3 is a perspective view of a stylet in accordance with one aspect of the present invention.

FIG. 7A is a schematic view of a distal portion of the steerable and curvable needle of FIG. 6, shown in a linear configuration.

FIG. 7B is a schematic view as in FIG. 7A, following proximal retraction of a pull wire to laterally deflect the distal end.

FIGS. 11A through 11C illustrate various aspects of a further deflectable needle design in accordance with the present invention.

FIGS. 12 and 13 illustrate a further variation of the deflectable needle design in accordance with the present invention.

FIG. 14 is a side elevational cross section through the proximal handle of the deflectable needle illustrated in FIG. 13.

FIG. 15 is a cross sectional detail view of the distal tip of the steerable and curvable needle illustrated in FIG. 13.

FIGS. 15A through 15H illustrate various views of alternative distal tip designs.

FIGS. 16A and 16B are schematic illustrations of the distal end of a steerable and curvable injection device in accordance with the present invention, having a cavity creating element thereon.

FIGS. 16C and 16D are alternative cross sectional views taken along the line 16C-16C in FIG. 16A, showing different inflation lumen configurations.

FIGS. 17A and 17B illustrate an alternative steerable and curvable injection device having a cavity creation element thereon.

FIGS. 18A and 18B are schematic views of a bone cement delivery system in accordance with the present invention.

FIGS. 20A through 20D illustrate various components of a steerable and curvable drill, according to one embodiment of the invention.

FIGS. 21A through 21D illustrate cross-sections of a steerable and curvable drill with an axially floating drive shaft to compensate for catheter deflection, according to one embodiment of the invention.

FIGS. 23A through 23H schematically illustrate various views of an embodiment of a steerable and curvable drill with slit apertures extending along a portion of the distal drive shaft, according to one embodiment of the invention.

FIGS. 23I and 23J illustrate a coupling feature between the distal end of the drive shaft and the boring element, according to one embodiment of the invention.

DETAILED DESCRIPTION OF THE PREFERRED EMBODIMENT

Figure 4:
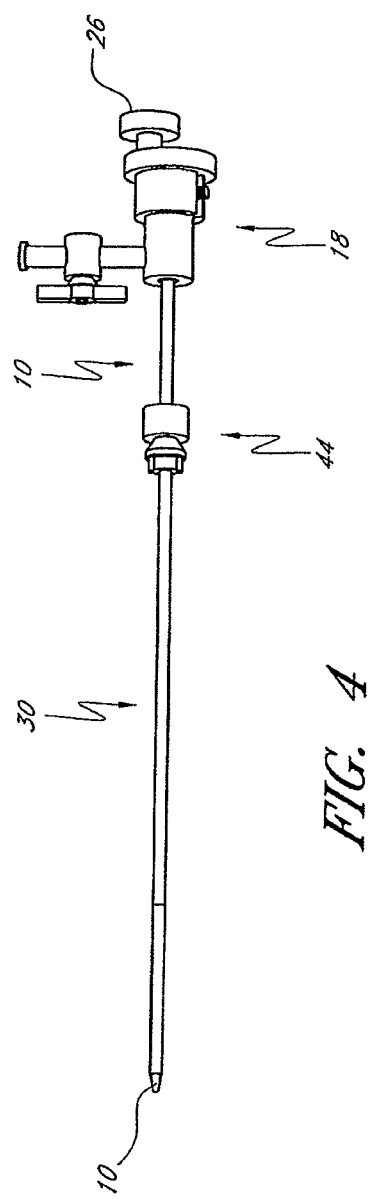
FIG. 4 is a side elevational view of the steerable and curvable injection needle moveably coaxially disposed within the introducer, in a substantially linear configuration.

The present invention provides improved delivery systems for delivery of a bone cement or bone cement composite for the treatment of vertebral compression fractures due to osteoporosis (OSP), osteo-trauma, and benign or malignant lesions such as metastatic cancers and myeloma, and associated access and deployment tools and procedures.

The primary materials in the preferred bone cement composite are methyl methacrylate and inorganic cancellous and/or cortical bone chips or particles. Suitable inorganic bone chips or particles are sold by Allosource, Osteotech and LifeNet (K053098); all have been cleared for marketing by FDA The preferred bone cement also may contain the additives: barium sulfate for radio-opacity, benzoyl peroxide as an initiator, N,N-dimethyl-p-toluidine as a promoter and hydroquinone as a stabilizer. Other details of bone cements and systems are disclosed in U.S. patent application Ser. No. 11/626,336, filed Jan. 23, 2007, the disclosure of which is hereby incorporated in its entirety herein by reference.

One preferred bone cement implant procedure involves a two-step injection process with two different concentrations of the bone particle impregnated cement. To facilitate the implant procedure the bone cement materials are packaged in separate cartridges containing specific bone cement and inorganic bone particle concentrations for each step. Tables 1 and 2, infra, list one example of the respective contents and concentrations in Cartridges 1A and 1B for the first injection step, and Cartridges 2A and 2B for the second injection step.

The bone cement delivery system generally includes at least three main components: 1) stylet; 2) introducer cannula; and 3) steerable and curvable injection needle. See FIGS. 1-3. Packaged with the system or packaged separately is a cement dispensing pump. The complete system also preferably includes at least one cement cartridge having at least two chambers therein, and a spiral mixing nozzle.

The stylet is used to perforate a hole into the pedicle of the vertebra to gain access to the interior of the vertebral body.

The introducer cannula is used for bone access and as a guide for the steerable and curvable injection needle. The introducer cannula is sized to allow physicians to perform vertebroplasty or kyphoplasty on vertebrae with small pedicles such as the thoracic vertebra T5 as well as larger vertebrae. In addition, this system is designed for uni-transpedicular access and/or bi-pedicular access.

Once bone access has been achieved, the steerable and curvable injection needle can be inserted through the introducer cannula into the vertebra. The entire interior vertebral body may be accessed using the steerable and curvable injection needle. The distal end of the needle can be manually shaped to any desired radius within the product specifications. The radius is adjusted by means of a knob on the proximal end of the device.

The hand-held cement dispensing pump may be attached to the steerable and curvable injection needle by a slip-ring luer fitting. The pre-filled 2-chambered cartridges (1A and 1B, and 2A and 2B) are loaded into the dispensing pump. As the handle of the dispensing pump is squeezed, each piston pushes the cartridge material into the spiral mixing tube. The materials are mixed in the spiral mixing nozzle prior to entering the steerable and curvable injection needle. The ratio of diameters of the cartridge chambers determines the mixing ratio for achieving the desired viscosity.

The bone cement implant procedures described herein use established vertebroplasty and kyphoplasty surgical procedures to stabilize the collapsed vertebra by injecting bone cement into cancellous bone.

The preferred procedure is designed for uni-transpedicular access and may be accomplished under either a local anesthetic or short-duration general anesthetic. Once the area of the spine is anesthetized, an incision is made and the stylet is used to perforate the vertebral pedicle and gain access to the interior of the vertebral body. The introducer cannula is then inserted and acts as a guide for the steerable and curvable injection needle.

Injection of the preferred bone cement involves a two-step procedure. The pre-filled Cartridges 1A and 1B are loaded into the dispensing pump. As the dispensing pump handle is squeezed, each piston pushes material into the spiral mixing tube. The diameter of each chamber may be utilized to determine the mixing ratio for achieving the desired viscosity.

The first step involves injecting a small quantity of PMMA with more than about 35%, e.g., 60% inorganic bone particles, onto the outer periphery of the cancellous bone matrix, i.e., next to the inner wall of the cortical bone of the vertebral body. The cement composite is designed to harden relatively quickly, forming a firm but still pliable shell. This shell is intended to prevent bone marrow/PMMA content from being ejected through any venules or micro-fractures in the vertebral body wall. The second step of the procedure involves a second injection of PMMA with an approximately 30% inorganic bone particles to stabilize the remainder of the weakened, compressed cancellous bone.

Alternatively, the steerable and curvable needle disclosed herein and discussed in greater detail below, can be used in conventional vertebroplasty procedures, using a single step bone cement injection.

Injection control for the first and second steps is provided by a 2 mm ID flexible injection needle, which is coupled to the hand operated bone cement injection pump. The 60% (>35%) and 30% ratio of inorganic bone particle to PMMA concentrations may be controlled by the pre-filled cartridge sets 1A and 1B, and 2A and 2B. At all times, the amount of the injectate is under the direct control of the surgeon or intervention radiologist and visualized by fluoroscopy. The introducer cannula is slowly withdrawn from the cancellous space as the second injection of bone cement begins to harden, thus preventing bone marrow/PMMA content from exiting the vertebral body. The procedure concludes with closure of the surgical incision with bone filler. In vitro and in vivo studies have shown that the 60% (>35%) bone-particle impregnated bone cement hardens in 2-3 minutes and 30% bone-particle impregnated bone cement hardens between 4 to 10 minutes.

Details of the system components will be discussed below.

There is provided in accordance with the present invention a steerable and curvable injection device that can be used to introduce any of a variety of materials or devices for diagnostic or therapeutic purposes. In one embodiment, the system is used to inject bone cement, e.g., PMMA or any of the bone cement compositions disclosed elsewhere herein. The injection system most preferably includes a tubular body with a steerable and curvable (i.e., deflectable) distal portion for introducing bone cement into various locations displaced laterally from the longitudinal axis of the device within a vertebral body during a vertebroplasty procedure.

Referring to FIG. 1, there is illustrated a side perspective view of a steerable and curvable injection needle 10 in accordance with one aspect of the present invention. The steerable and curvable injection needle 10 comprises an elongate tubular body 12 having a proximal end 14 and a distal end 16. The proximal end 14 is provided with a handle or manifold 18, adapted to remain outside of the patient and enable introduction and/or aspiration of bone cement or other media, and control of the distal end as will be described herein. In general, manifold 18 is provided with at least one injection port 20, which is in fluid communication with a central lumen (not illustrated) extending through tubular body 12 to at least one distal exit port 22.

The manifold 18 is additionally provided with a control 26 such as a rotatable knob, slider, or other moveable control, for controllably deflecting a deflection zone 24 on the distal end 16 of the tubular body 12. As is described elsewhere herein, the deflection zone 24 may be advanced from a relatively linear configuration as illustrated in FIG. 1 to a deflected configuration throughout an angular range of motion.

Referring to FIG. 2, there is illustrated an elongate tubular introducer 30, having a proximal end 32, a distal end 34 and an elongate tubular body 36 extending therebetween. A central lumen 38 (not shown) extends between a proximal access port 40 and a distal access port 42.

The central lumen 38 has an inside diameter which is adapted to slideably axially receive the steerable and curvable injection needle 10 therethrough. This enables placement of the distal end 34 adjacent a treatment site within the body, to establish an access pathway from outside of the body to the treatment site. As will be appreciated by those of skill in the art, the introducer 30 enables procedures deep within the body such as within the spine, through a minimally invasive and/or percutaneous access. The steerable and curvable injection needle 10 and/or other procedure tools may be introduced into port 40, through lumen 38 and out of port 42 to reach the treatment site.

The proximal end 32 of introducer 30 may be provided with a handle 44 for manipulation during the procedure. Handle 44 may be configured in any of a variety of ways, such as having a frame 46 with at least a first aperture 48 and a second aperture 50 to facilitate grasping by the clinician.

Referring to FIG. 3, there is illustrated a perspective view of stylet 60. Stylet 60 comprises a proximal end 62, a distal end 64 and an elongate body 66 extending therebetween. The proximal end 62 may be provided with a stop 68 such as a grasping block, manifold or other structure, to facilitate manipulation by the clinician. In the illustrated embodiment, the block 68 is configured to nest within a recess 70 on the proximal end of the introducer 30.

As will be appreciated by those of skill in the art, the stylet 60 has an outside diameter which is adapted to coaxially slide within the central lumen on introducer 30. When block 68 is nested within recess 70, a distal end 64 of stylet 60 is exposed beyond the distal end 34 of introducer 30. The distal end 64 of stylet 60 may be provided with a pointed tip 72, such as for anchoring into the surface of a bone.

Referring to FIG. 4, there is illustrated a side elevational view of an assembly in accordance with the present invention in which a steerable and curvable injection needle 10 is coaxially positioned within an introducer 30. The introducer 30 is axially moveably carried on the steerable and curvable injection needle 10. In the illustration of FIG. 4, the introducer 30 is illustrated in a distal position such that it covers at least a portion of the deflection zone 24 on injection needle 10.

Figure 5:
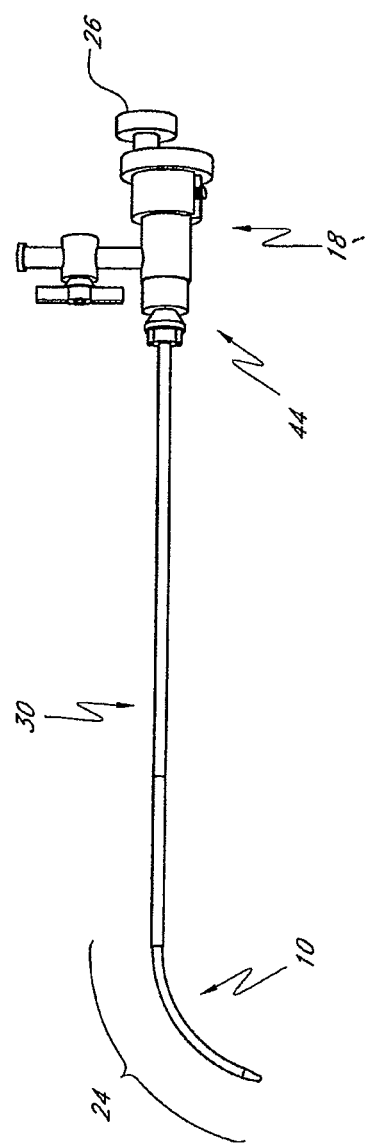
FIG. 5 is a side elevational view of the assembly of FIG. 4, showing the steerable and curvable injection needle in a curved configuration.

FIG. 5 illustrates an assembly as in FIG. 4, in which the introducer 30 has been proximally retracted along the injection needle 10 to fully expose the deflection zone 24 on injection needle 10. In addition, the control 26 has been manipulated to deflect the deflection zone 24 through an angle of approximately 90°. Additional details of the steerable and curvable needle will be discussed below.

Figure 6:
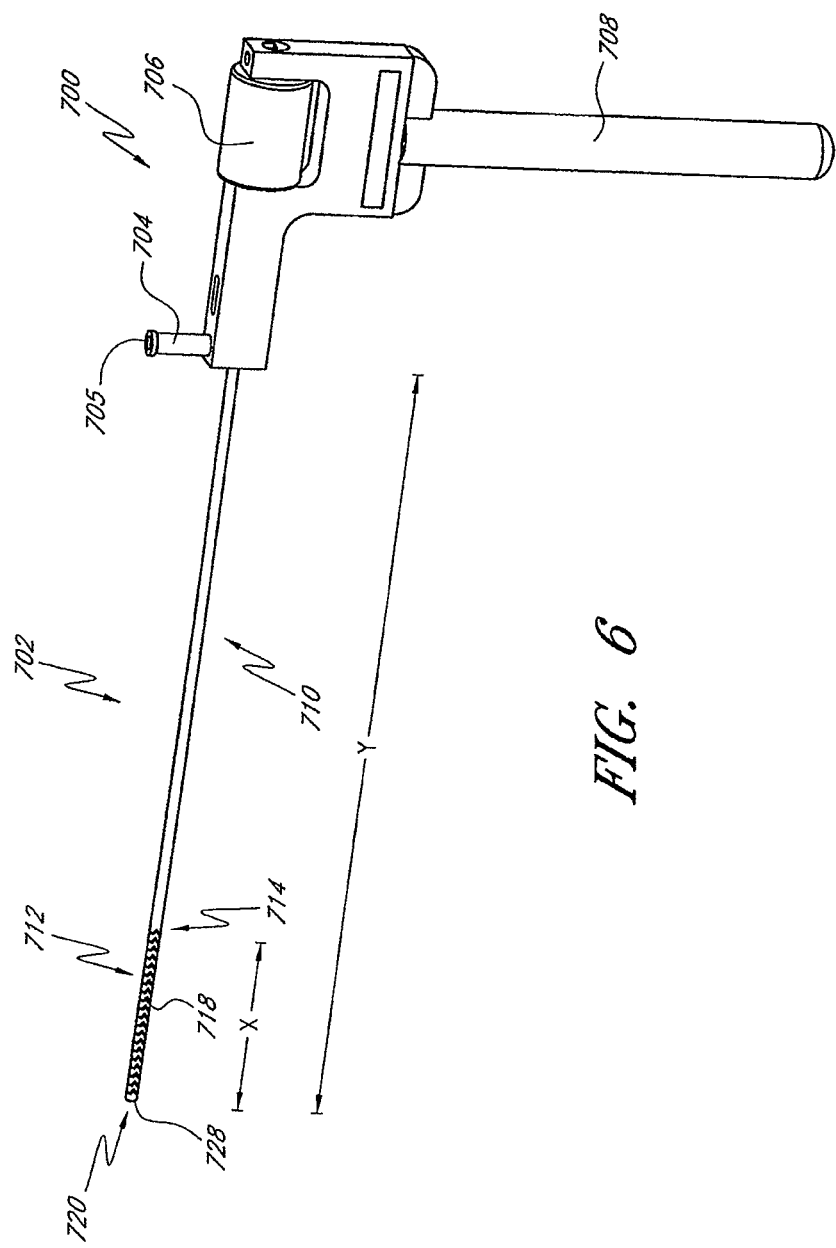
FIG. 6 is a side elevational schematic view of another steerable and curvable injection needle in accordance with the present invention.

FIG. 6 illustrates a schematic perspective view of an alternate steerable and curvable vertebroplasty injector, according to one embodiment of the invention. The steerable and curvable injector 700 includes a body or shaft portion 702 that is preferably elongate and tubular, input port 704, adjustment control 706, and handle portion 708. The elongate shaft 702 preferably has a first proximal portion 710 and a second distal portion 712 which merge at a transition point 714. Shaft 702 may be made of stainless steel, such as 304 stainless steel, Nitinol, Elgiloy, or other appropriate material. Alternatively, the tubular body 702 may be extruded from any of a variety of polymers well known in the catheter arts, such as PEEK, PEBAX, nylon and various polyethylenes. Extruded tubular bodies 702 may be reinforced using metal or polymeric spiral wrapping or braided wall patterns, as is known in the art.

The shaft 702 defines at least one lumen therethrough that is preferably configured to carry a flowable bone cement prior to hardening. Proximal portion 710 of shaft 702 is preferably relatively rigid, having sufficient column strength to push through cancellous bone. Distal portion 712 of shaft 702 is preferably flexible and/or deflectable and reversibly actuatable between a relatively straight configuration and one or more deflected configurations or curved configurations as illustrated, for example, in FIG. 5, as will be described in greater detail below. The distal portion 712 of shaft 702 may include a plurality of transverse slots 718 that extend partially circumferentially around the distal portion 712 of the shaft 702 to provide a plurality of flexion joints to facilitate bending.

Input port 704 may be provided with a Luer lock connector although a wide variety of other connector configurations, e.g., hose barb or slip fit connectors can also be used. Lumen 705 of input port 704 is fluidly connected to central lumen 720 of shaft 702 such that material can flow from a source, through input port 704 into central lumen 720 of the shaft 702 and out the open distal end or out of a side opening on distal portion 712. Input port 704 is preferably at least about 20 gauge and may be at least about 18, 16, 14, or 12 gauge or larger in diameter.

Input port 704 advantageously allows for releasable connection of the steerable and curvable injection device 700 to a source of hardenable media, such as a bone cement mixing device described herein. In some embodiments, a plurality of input ports 704, such as 2, 3, 4, or more ports are present, for example, for irrigation, aspiration, introduction of medication, hardenable media precursors, hardenable media components, catalysts or as a port for other tools, such as a light source, cautery, cutting tool, visualization devices, or the like. A first and second input port may be provided, for simultaneous introduction of first and second bone cement components such as from a dual chamber syringe or other dispenser. A mixing chamber may be provided within the injection device 700, such as within the proximal handle, or within the tubular shaft 702

A variety of adjustment controls 706 may be used with the steerable and curvable injection system, for actuating the curvature of the distal portion 712 of the shaft 702. Preferably, the adjustment control 706 advantageously allows for one-handed operation by a physician. In one embodiment, the adjustment control 706 is a rotatable member, such as a thumb wheel or dial. The dial can be operably connected to a proximal end of an axially movable actuator such as pull wire 724. See FIG. 7A. When the dial is rotated in a first direction, a proximally directed tension force is exerted on the pull wire 724, actively changing the curvature of the distal portion 712 of the shaft 702 as desired. The degree of deflection can be observed fluoroscopically, and/or by printed or other indicium associated with the control 706. Alternative controls include rotatable knobs, slider switches, compression grips, triggers such as on a gun grip handle, or other depending upon the desired functionality.

In some embodiments, the adjustment control 706 allows for continuous adjustment of the curvature of the distal portion 712 of shaft 702 throughout a working range. In other embodiments, the adjustment control is configured for discontinuous (i.e., stepwise) adjustment, e.g., via a ratcheting mechanism, preset slots, deflecting stops, a rack and pinion system with stops, ratcheting band (adjustable ziptie), adjustable cam, or a rotating dial of spring loaded stops. In still other embodiments, the adjustment control 706 may include an automated mechanism, such as a motor or hydraulic system to facilitate adjustment.

The adjustment control may be configured to allow deflection of the distal portion 712 through a range of angular deviations from 0 degrees (i.e., linear) to at least about 15°, and often at least about 25°, 35°, 60°, 90°, 120°, 150°, or more degrees from linear.

In some embodiments, the length X of the flexible distal portion 712 of shaft 702 is at least about 10%, in some embodiments at least about 15%, 25%, 35%, 45%, or more of the length Y of the entire shaft 702 for optimal delivery of bone cement into a vertebral body. One of ordinary skill in the art will recognize that the ratio of lengths X:Y can vary depending on desired clinical application. In some embodiments, the maximum working length of needle 702 is no more than about 15", 10", 8", 7", 6", or less depending upon the target and access pathway. In one embodiment, when the working length of needle 702 is no more than about 8", the adjustable distal portion 712 of shaft has a length of at least about 1" and preferably at least about 1.5" or 2".

FIGS. 7A-B are schematic perspective views of a distal portion of shaft 702 of a steerable and curvable vertebroplasty injector, according to one embodiment of the invention. Shown is the preferably rigid proximal portion 710 and deflectable distal portion 712. The distal portion 712 of shaft 702 includes a plurality of transverse slots 718 that extend partially circumferentially around the distal portion 712 of the shaft 702, leaving a relatively axially non-compressible spine 719 in the form of the unslotted portion of the tubular wall.

In some embodiments, the slots 718 can be machined or laser cut out of the tube stock that becomes shaft 702, and each slot may have a linear, chevron or other shape. In other embodiments, the distal portion 712 of shaft 702 may be created from an elongate coil rather than a continuous tube.

Slots 718 provide small compression hinge joints to assist in the reversible deflection of distal portion 712 of shaft 702 between a relatively straightened configuration and one or more curved configurations. One of ordinary skill in the art will appreciate that adjusting the size, shape, and/or spacing of the slots 718 can impart various constraints on the radius of curvature and/or limits of deflection for a selected portion of the distal portion 712 of shaft 702. For example, the distal portion 712 of shaft 702 may be configured to assume a second, fully deflected shape with a relatively constant radius of curvature throughout its length. In other embodiments, the distal portion 712 may assume a progressive curve shape with a variable radius of curvature which may, for example, have a decreasing radius distally. In some embodiments, the distal portion may be laterally displaced through an arc having a radius of at least about 0.5", 0.75", 1.0", 1.25", or 1.5" minimum radius (fully deflected) to ∞ (straight) to optimize delivery of bone cement within a vertebral body. Wall patterns and deflection systems for bendable slotted tubes are disclosed, for example, in U.S. Patent Publication No. 2005/0060030 A1 to Lashinski et al., the disclosure of which is incorporated in its entirety by reference herein.

Still referring to FIGS. 7A-B, a pull wire 724 resides within the lumen 720 of shaft 702. The distal end 722 of the pull wire 724 is preferably operably attached, such as by adhesive, welding, soldering, crimping or the like, to an inner side wall of the distal portion 712 of the shaft 702. Preferably, the attachment point will be approximately 180° offset from the center of the axially extending spine 719. Proximal portion of pull wire 724 is preferably operably attached to adjustment control 706. The adjustment control 706 may be configured to provide an axial pulling force in the proximal direction toward the proximal end of pull wire 724. This in turn exerts a proximal traction on the distal portion 712 of shaft 702 operably attached to distal end 722 of pull wire 724. The slotted side of the tubular body shortens under compression, while the spine side 719 retains its axial length causing the distal portion 712 of shaft 702 to assume a relatively curved or deflected configuration. In some embodiments, a plurality of pull wires, such as two, three, four, or more pull wires 724 may be present within the lumen 720 with distal points of attachment spaced axially apart to allow the distal portion 712 of shaft 702 to move through compound bending curves depending on the desired bending characteristic. Distal axial advance of the actuator will cause a deflection in an opposite direction, by increasing the width of the slots 718.

Figure 8:
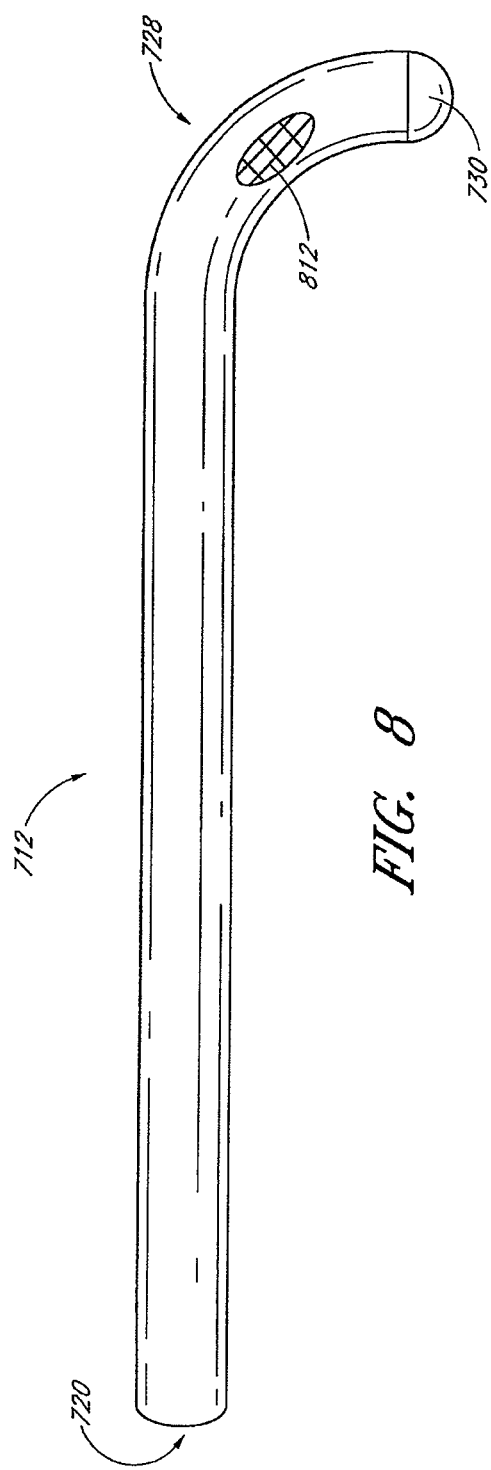
FIG. 8 is a schematic view of a distal portion of a steerable and curvable needle, having a side port.

A distal opening 728 is provided on shaft 702 in communication with central lumen 720 to permit expression of material, such as bone cement, from the injector 700. Some embodiments may include a filter such as mesh 812. Mesh structure 812 can advantageously control cement output by controlling bubbles and/or preventing undesired large or unwieldy aggregations of bone cement from being released at one location and thus promote a more even distribution of bone cement within the vertebral body. The mesh 812 may be created by a laser-cut cris-crossing pattern within distal end as shown, or can alternatively be separately formed and adhered, welded, or soldered on to the distal opening 728. Referring to FIG. 8, the distal shaft portion 712 may also include an end cap 730 or other structure for occluding central lumen 720, and a distal opening 728 on the sidewall of shaft 702.

In some embodiments, the distal shaft 712 can generate a lateral force of at least about 0.125 pounds, 0.25 pounds, 0.5 pounds, 1 pound, 1.5 pounds, 2 pounds, 3 pounds, 4 pounds, 5 pounds, 6 pounds, 7 pounds, 8 pounds, 9 pounds, 10 pounds, or more by activating control 706. This can be advantageous to ensure that the distal portion 712 is sufficiently navigable laterally through cancellous bone to distribute cement to the desired locations. In some embodiments, the distal shaft 712 can generate a lateral force of at least about 0.125 pounds but no more than about 10 pounds; at least about 0.25 pounds but no more than about 7 pounds; or at least about 0.5 pounds but no more than about 5 pounds.

In some embodiments, the distal portion 712 of shaft 702 (or end cap 730) has visible indicia, such as, for example, a marker visible via one or more imaging techniques such as fluoroscopy, ultrasound, CT, or MRI.

Figure 9A:
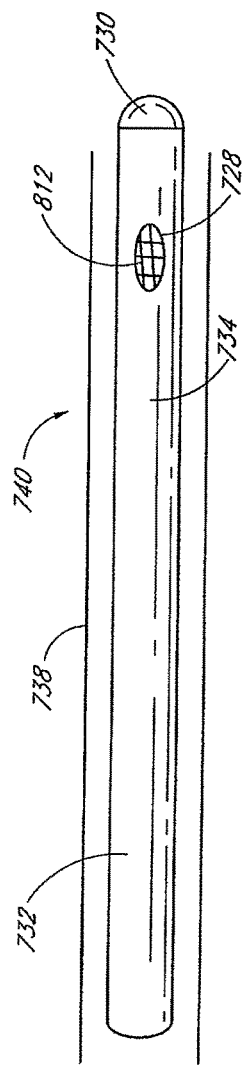
FIG. 9A is a schematic view of a distal portion of a steerable and curvable needle, positioned within an outer sheath.
Figure 9B:
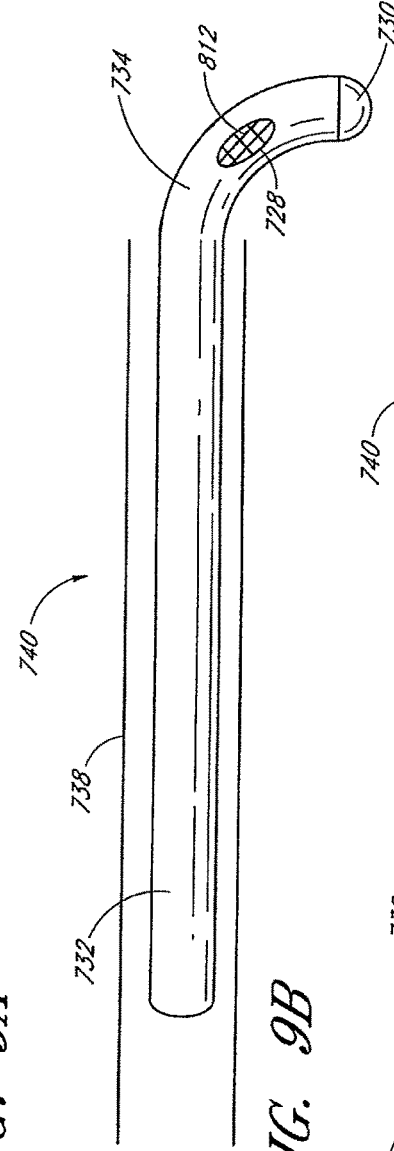
FIG. 9B is an illustration as in FIG. 9A, with the distal sheath partially proximally retracted.
Figure 9C:
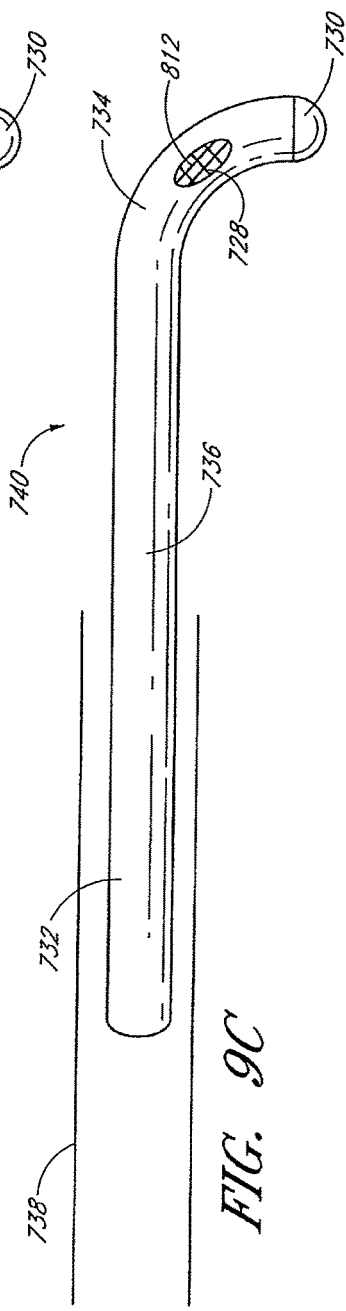
FIG. 9C is an illustration as in FIG. 9B, with the outer sheath proximally retracted a sufficient distance to fully expose the deflection zone.

FIGS. 9A-C illustrate in schematic cross-section another embodiment of a distal portion 734 of a steerable and curvable injection device 740. The tubular shaft 736 can include a distal portion 734 made of or containing, for example, a shape memory material that is biased into an arc when in an unconstrained configuration. Some materials that can be used for the distal curved portion 734 include Nitinol, Elgiloy, stainless steel, or a shape memory polymer. A proximal portion 732 of the shaft 736 is preferably relatively straight as shown. Also shown is end cap 730, distal lateral opening 728 and mesh 812.

The distal curved portion 734 may be configured to be axially movably received within an outer tubular sheath 738. The sheath 738 is preferably configured to have sufficient rigidity and radial strength to maintain the curved distal portion 734 of shaft 732 in a relatively straightened configuration while the outer tubular sheath 738 coaxially covers the curved distal portion 734. Sheath 738 can be made of, for example, a metal such as stainless steel or various polymers known in the catheter arts. Axial proximal withdrawal of the sheath 738 with respect to tubular shaft 736 will expose an unconstrained portion of the shape memory distal end 734 which will revert to its unstressed arcuate configuration. Retraction of the sheath 738 may be accomplished by manual retraction by an operator at the proximal end, retraction of a pull wire attached to a distal portion of the sheath 738, or other ways as known in the art. The straightening function of the outer sheath 738 may alternatively be accomplished using an internal stiffening wire, which is axially movably positionable within a lumen extending through the tubular shaft 736. The length, specific curvature, and other details of the distal end may be as described elsewhere herein.

Figure 10A:
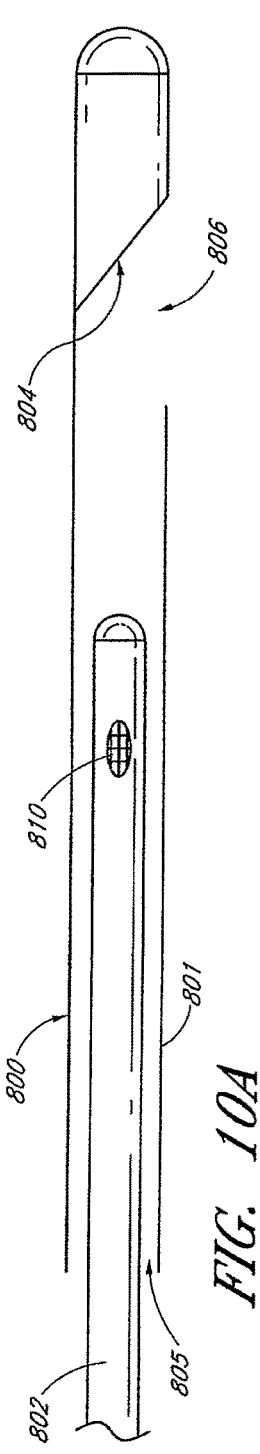
FIGS. 10A-10C illustrate various aspects of an alternative deflectable needle in accordance with the present invention.
Figure 10B:
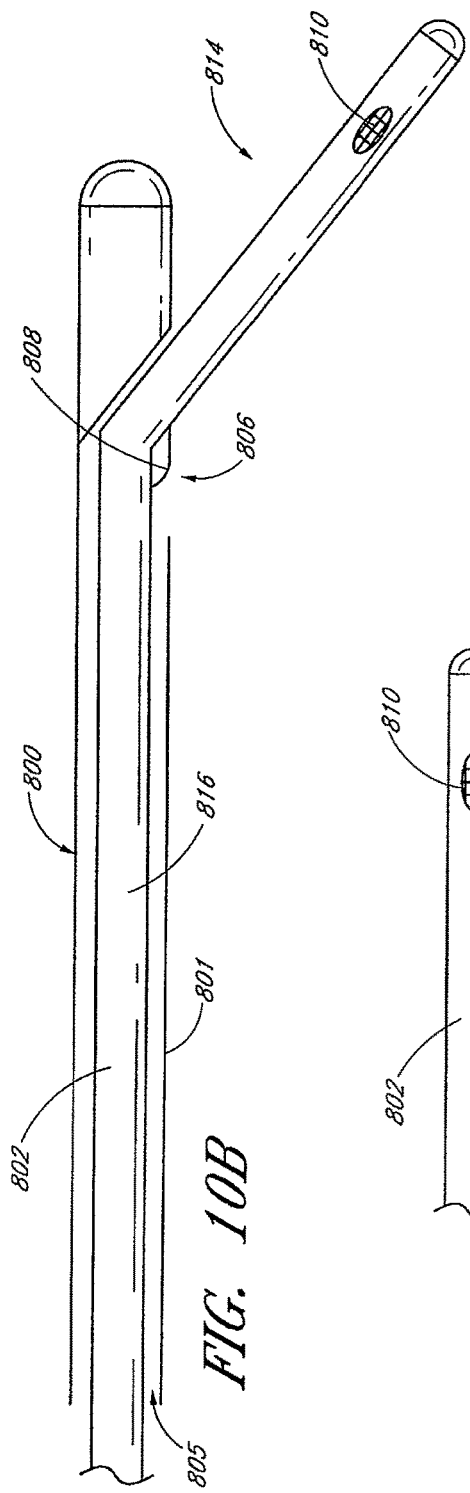
Figure 10C:
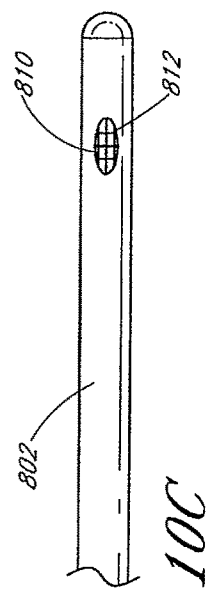

In another embodiment, as shown in FIGS. 10A-C, tubular shaft 802 of a steerable and curvable vertebroplasty injector may be generally substantially straight throughout its length in its unstressed state, or have a laterally biased distal end. A distally facing or side facing opening 810 is provided for the release of a material, such as bone cement. In this embodiment, introducer 800 includes an elongate tubular body 801 with a lumen 805 therethrough configured to receive the tubular shaft (also referred to as a needle) 802. Introducer 800 can be made of any appropriate material, such as, stainless steel and others disclosed elsewhere herein. Needle 802 may be made of a shape memory material, such as nitinol, with superelastic properties, and has an outside diameter within the range of between about 1 to about 3 mm, about 1.5-2.5 mm, or about 2.1 mm in some embodiments.

Introducer 800 includes a needle-redirecting element 804 such as an inclined surface near its distal end. Needle-redirecting element 804 can be, for example, a laser-cut tang or a plug having a proximal surface configured such that when needle 802 is advanced distally into introducer 800 and comes in contact with the needle-redirecting element 804, a distal portion 814 of needle 802 is redirected out an exit port 806 of introducer 800 at an angle 808, while proximal portion 816 of needle 802 remains in a relatively straightened configuration, as shown in FIG. 10B. Bone cement can then be ejected from distal opening 810 on the end or side of needle 802 within bone. Distal opening 810 may be present at the distal tip of the needle 802 (coaxial with the long axis of the needle 802) or alternatively located on a distal radial wall of needle 802 as shown in FIG. 10C. In some embodiments, the angle 808 is at least about 15 degrees and may be at least about 30, 45, 60, 90, 105 degrees or more with respect to the long axis of the introducer 800.

The illustrated embodiment of FIGS. 10A-C and other embodiments disclosed herein are steerable and curvable through multiple degrees of freedom to distribute bone cement to any area within a vertebral body. For example, the introducer 800 and needle 802 can both rotate about their longitudinal axes with respect to each other, and needle 802 can move coaxially with respect to the introducer 800, allowing an operator to actuate the injection system three dimensionally. The distal portion 814 of needle 802 can be deflected to a position that is angularly displaced from the long axis of proximal portion 816 of needle without requiring a discrete curved distal needle portion as shown in other embodiments herein.

FIGS. 11A-C illustrate another embodiment of a steerable and curvable vertebroplasty injector. FIG. 11A schematically shows handle portion 708, adjustment control 706, and elongate needle shaft 702, including proximal portion 710, distal portion 712, and transition point 714. FIG. 11B is a vertical cross-section through line A-A of FIG. 11A, and shows adjustment control 706 operably connected to pull wire 724 such as through a threaded engagement. Also shown is input port 704, and proximal portion 710 and distal portion 712 of needle shaft 702. FIG. 11C illustrates a cross-sectional view of distal portion 712 of shaft 702. The distal end 722 of pull wire 724 is attached at an attachment point 723 to the distal portion 712 of shaft 702. Proximal retraction on pullwire 724 will collapse transverse slots 718 and deflect the injector as has been discussed. Also shown is an inner tubular sleeve 709, which can be advantageous to facilitate negotiation of objects or media such as bone cement, through the central lumen of the needle shaft 702.

The interior sleeve 709 is preferably in the form of a continuous, tubular flexible material, such as nylon or polyethylene. In an embodiment in which the needle 702 has an outside diameter of 0.095 inches (0.093 inch coil with a 0.001 inch thick outer sleeve) and an inside diameter of 0.077 inches, the interior tubular sleeve 709 may have an exterior diameter in the area of about 0.074 inches and an interior diameter in the area of about 0.069 inches. The use of this thin walled tube 705 on the inside of the needle shaft 702 is particularly useful for guiding a fiber through the needle shaft 702. The interior tube 705 described above is additionally preferably fluid-tight, and can be used to either protect the implements transmitted therethrough from moisture, or can be used to transmit bone cement through the steerable and curvable needle.

In some embodiments, an outer tubular coating or sleeve (not shown) is provided for surrounding the steerable and curvable needle shaft at least partially throughout the distal end of the needle. The outer tubular sleeve may be provided in accordance with techniques known in the art and, in one embodiment, is a thin wall polyester (e.g., ABS) heat shrink tubing such as that available from Advanced Polymers, Inc. in Salem, N.H. Such heat shrink tubings have a wall thickness of as little as about 0.0002 inches and tube diameter as little as about 0.010 inches. The outer tubular sleeve enhances the structural integrity of the needle, and also provides a fluid seal and improved lubricity at the distal end over embodiments with distal joints 718. Furthermore, the outer tubular sleeve tends to prevent the device from collapsing under a proximal force on a pull wire. The sleeve also improves pushability of the tubular members, and improves torque transmission.

In other embodiments, instead of a slotted tube, the needle shaft of a vertebroplasty injection system may include a metal or polymeric coil. Steerable and curvable helical coil-type devices are described, for example, in U.S. Pat. No. 5,378,234 or 5,480,382 to Hammerslag et al., which are both incorporated by reference herein in their entirety.

An interior tubular sleeve (not illustrated) may be provided to facilitate flow of media through the central lumen as described elsewhere in the application. In some embodiments, a heat-shrink outer tubular sleeve as described elsewhere in the application is also provided to enhance the structural integrity of the sheath, provide a fluid seal across the chevrons or slots, as well as improve lubricity.

The steerable and curvable injection needle (also referred to as the injection shaft) may have an outside diameter of between about 8 to 24 gauge, more preferably between about 10 to 18 gauge, e.g., 12 gauge, 13 gauge (0.095" or 2.41 mm), 14 gauge, 15 gauge, or 16 gauge. In some embodiments, the inside diameter (luminal diameter) of the injection needle is between about 9 to 26 gauge, more preferably between about 11 to 19 gauge, e.g., 13 gauge, 14 gauge, 15 gauge, 16 gauge, or 17 gauge. In some embodiments, the inside diameter of the injection needle is no more than about 4 gauge, 3 gauge, 2 gauge, or 1 gauge smaller than the outside diameter of the injection needle.

The inside luminal diameter of all of the embodiments disclosed herein is preferably optimized to allow a minimal exterior delivery profile while maximizing the amount of bone cement that can be carried by the needle. In one embodiment, the outside diameter of the injection needle is 13 gauge (0.095" or 2.41 mm) with a 0.077" (1.96 mm) lumen. In some embodiments, the percentage of the inside diameter with respect to the outside diameter of the injection needle is at least about 60%, 65%, 70%, 75%, 80%, 85%, or more.

Referring to FIGS. 12 and 13, there is illustrated a modification of the steerable and curvable injection needle 10, in accordance with the present invention. The injection needle 10 comprises an elongate tubular shaft 702, extending between a proximal portion 710 and a distal portion 712. The proximal portion 710 is carried by a proximal handle 708, which includes a deflection control 706 such as a rotatable knob or wheel. Rotation of the control 706 causes a lateral deflection or curvature of the distal steering region 24 as has been discussed.

Input port 704 is in fluid communication with a distal opening 728 on a distal tip 730, by way of an elongate central lumen 720. Input port 704 may be provided with any of a variety of releasable connectors, such as a luer or other threaded or mechanically interlocking connector known in the art. Bone cement or other media advanced through lumen 720 under pressure may be prevented from escaping through the plurality of slots 718 in the steering region 24 by the provision of a thin flexible tubular membrane carried either by the outside of tubular shaft 702, or on the interior surface defining central lumen 720.

Referring to FIG. 14, the handle 708 is provided with an axially oriented central bore 732 having a first, female thread 733 thereon. A slider 734 having a second complementary male thread 735, is threadably engaged with the central bore 732. Rotation of the knob 706 relatively to the slider 734 thus causes the slider 734 to distally advance or proximally retract in an axial direction with respect to the handle 708. The slider 734 is mechanically linked to the pull wire 724, such as by the use of one or more set screws or other fastener 740.

Slider 734 is provided with at least one axially extending keyway or spline 742 for slideably engaging a slide dowel pin 744 linked to the handle 708. This allows rotation of the rotatable control 706, yet prevents rotation of the slider 734 while permitting axial reciprocal movement of the slider 734 as will be apparent to those of skill in the art. One or more actuating knob dowel pins 746 permits rotation of the rotatable control 706 with respect to the handle 708 but prevents axial movement of the rotatable control 706 with respect to the handle 708.

Referring to FIG. 15, the distal end of the shaft 702 may be provided with any of a variety of distal opening 728 orientations or distal tip 730 designs, depending upon the desired functionality. In the illustrated embodiment, the distal tip 730 is provided with an annular flange 748 which may be slip fit into the distal end of the tubular body 702, to facilitate attachment. The attachment of the distal tip 730 may be further secured by welding, crimping, adhesives, or other bonding technique.

In general, the distal tip 730 includes a proximal opening 750 for receiving media from the central lumen 720, and advancing media through distal opening 728. Distal opening 728 may be provided on a distally facing surface, on a laterally facing surface, or on an inclined surface of the distal tip 730.

Referring to FIGS. 15A and 15B, there is illustrated a distal tip 30 having a single inclined opening 728 thereon. In any of the designs disclosed herein, one or two or three or four or more distal ports 728 may be provided, depending upon the desired clinical performance. In the illustrated embodiment, the distal tip includes a rounded distal end 750 which transitions either smoothly or through an angular interface with an inclined portion 752. The distal opening 728 is positioned distally of a transition 754 at the proximal limit of the inclined surface 752. This configuration enables the distal opening 728 to have a distal axially facing component, as compared to an embodiment having a side wall opening. See, for example, FIG. 8.

Referring to FIG. 15B, the tip 730 can be considered to have a central longitudinal axis 770. The aperture 728 may be considered as residing on an aperture plane 772, which intersects the distal most limit and the proximal most limit of the aperture 728. Aperture plane 772 intersects the longitudinal axis at an angle θ. In an embodiment having a side wall aperture, the aperture plane 772 and longitudinal axis 770 would be parallel. In an embodiment having a completely distally facing aperture, the aperture plane 772 would intersect the longitudinal axis 770 at an angle of 90°.

In the illustrated embodiment, the inclined aperture 728 is defined by an aperture plane 772 intersecting the longitudinal axis 770 at an angle θ which is at least about 5°, often at least about 15°, and in many embodiments, at least about 25° or more. Intersection angles within the range of from about 15° to about 45° may often be used, depending upon the desired clinical performance.

Figure 15D:
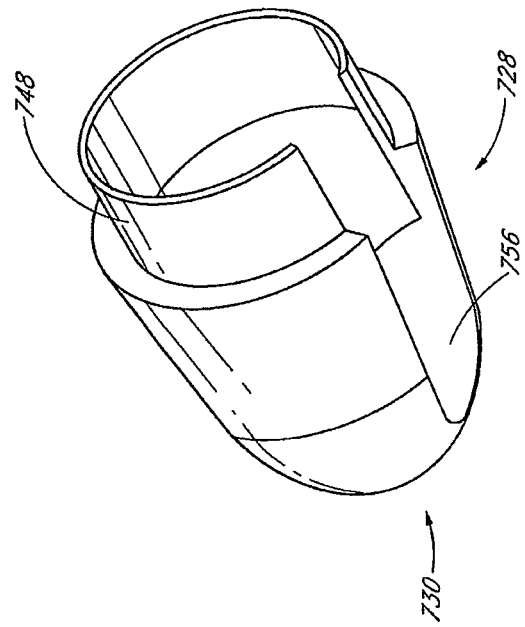
Figure 15C:
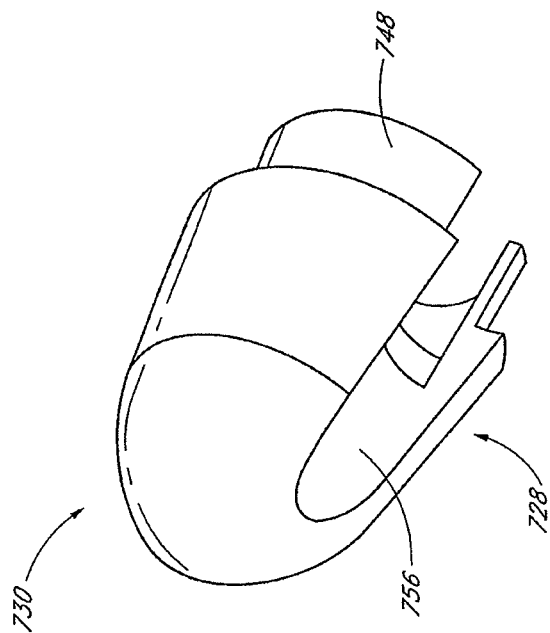

Referring to FIGS. 15C and 15D, an alternate distal tip 730 is illustrated. In this configuration, the distal opening 728 is in the form of a sculpted recess 756 extending axially in alignment with at least a portion of the central lumen 720. Sculpted recess 756 may be formed in any of a variety of ways, such as by molding, or by drilling an axial bore in an axial direction with respect to the tip 730. The sculpted recess 756 cooperates with the tubular body 702, as mounted, to provide a distal opening 728 having an inclined aspect as well as an axially distally facing aspect with respect to the longitudinal axis of the steerable and curvable needle.

Figure 15F:
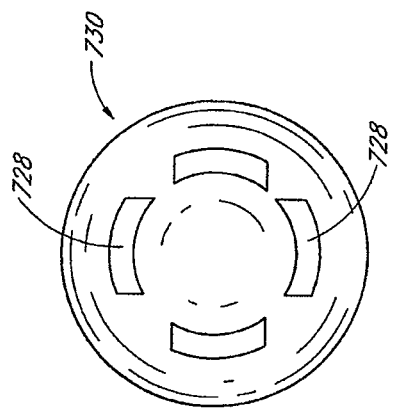
Figure 15E:
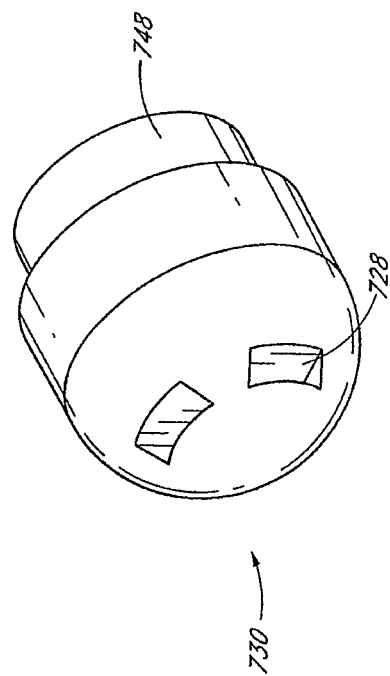

Referring to FIGS. 15E and 15F, there is illustrated a distal tip 730 having a plurality of distally facing apertures 728. In the illustrated embodiment, four distal apertures are provided. The distal apertures 728 may be provided on the rounded distal end 750, or on an inclined surface 752 as has been discussed.

Figure 15H:
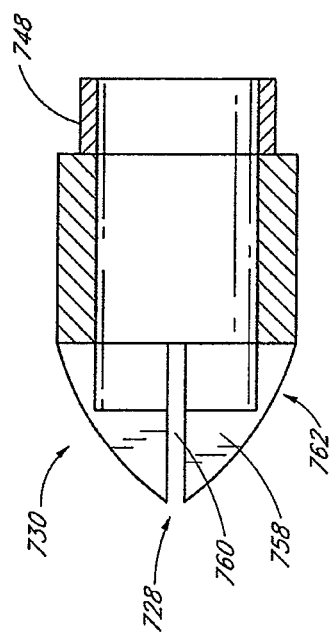
Figure 15G:
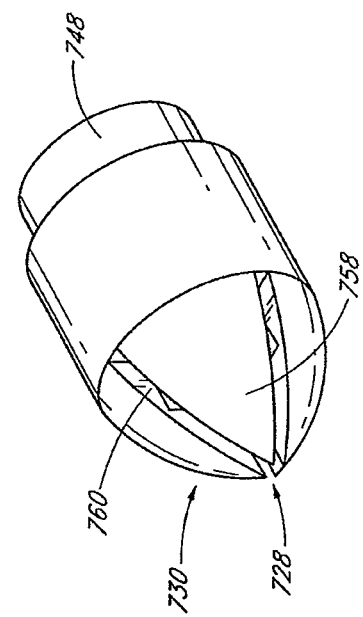

Referring to FIGS. 15G and 15H, there is illustrated an alternative distal tip 730. In this configuration, an opening 728 is oriented in a distally facing direction with respect to the longitudinal axis of the needle. The distal opening of the central lumen is covered by at least one, preferably two, and, as illustrated, four leaflets 758 to provide a collet like configuration. Each of the adjacent leaflets 758 is separated by a slot 760 and is provided with a living hinge or other flexible zone 762.

In use, the distal tip 730 may be distally advanced through soft tissue, cortical or cancellous bone, with the distal opening 728 being maintained in a closed orientation. Following appropriate positioning of the distal tip 30, the introduction of bone cement or other media under pressure through the central lumen 720 forces the distal opening 728 open by radially outwardly inclining each leaflet 758 about its flection point 762. This configuration enables introduction of the needle without "coring" or occluding with bone or other tissue, while still permitting injection of bone cement or other media in a distal direction.

Any of the forgoing or other tip configurations may be separately formed and secured to the distal end of the tubular body 702, or may be machined, molded or otherwise formed integrally with the tube 702. Other examples of tip configurations that can be used with injectors as described herein are illustrated and described in connection with FIGS. 15I to 15Y of U.S. Provisional Application No. 61/300,401 filed on Feb. 1, 2010, which is hereby incorporated by reference in its entirety.

Alternatively, a distal opening aperture may be occluded by a blunt plug or cap, which prevents coring during distal advance of the device. Once positioned as desired, the distal cap may be pushed off of the distal end of the injector such as under the pressure of injected bone cement. The deployable cap may take any of a variety of forms depending upon the injector design. For example, it may be configured as illustrated in FIG. 15A, only without the aperture 728. The flange 748 is slip fit within the distal end of the injector body, and retained only by friction, or by a mild bond which is sufficient to retain the cap 730 during manipulation of the injector, but insufficient to resist the force of injected bone cement. The deployable cap 730 may be made from any of a variety of materials, such as stainless steel, Nitinol, or other implantable metals; any of a wide variety of implantable polymers such as PEEK, nylon, PTFE; or of bone cement such as PMMA. Alternatively, any of a variety of bioabsorbable polymers may be utilized to form the deployable cap 730, including blends and polymers in the PLA-PGLA absorbable polymer families.

As a further alternative, coring during insertion of an injector having a distal opening may be prevented by positioning a removable obturator in the distal opening. The obturator comprises an elongate body, extending from a proximal end throughout the length of the injector to a blunt distal tip. The obturator is advanced axially in a distal direction through the central lumen, until the distal tip of the obturator extends slightly distally of the distal opening in the injector. This provides a blunt atraumatic tip for distal advance of the injector through tissue. Following positioning of the injector, the obturator may be proximally withdrawn from the central lumen, and discarded. The obturator may be provided with any of a variety of structures for securing the obturator within the central lumen during the insertion step, such as a proximal cap for threadably engaging a complementary leer connector on the proximal opening of the central lumen.

In accordance with another aspect of the present invention, there is provided a combination device in which a steerable and curvable injector is additionally provided with a cavity formation element. Thus, the single device may be advanced into a treatment site within a bone, expanded to form a cavity, and used to infuse bone cement or other media into the cavity. Either or both of the expansion step and the infusion step may be accomplished following or with deflection of the distal portion of the injector.

Referring to FIGS. 16A and 16B, the distal portion 302 of a steerable and curvable injector 300 having a cavity formation element 320 thereon is schematically illustrated. The steerable and curvable injector 300 includes a relatively rigid proximal section 304 and a deflectable section 306 as has been discussed elsewhere herein. The lateral flexibility of distal section 306 may be accomplished in any of a variety of ways, such as by the provision of a plurality of transverse chevrons or slots 308. Slots 308 may be machined or laser cut into appropriate tube stock, such as stainless steel or any of a variety of rigid polymers.

The slots 308 oppose a column strength element such as an axially extending spine 310, for resisting axial elongation or compression of the device. A pull wire 312 axially moveably extends throughout the length of the tubular body, and is secured with respect to the tubular body distally of the transverse slots 308. The proximal end of the pull wire is operatively connected to a control on a proximal handpiece or manifold. The control may be any of a variety of structures, such as a lever, trigger, slider switch or rotatable thumb wheel or control knob. Axial proximal traction (or distal advance) of the pull wire 312 with respect to the tubular body causes a lateral deflection of the distal steering section 306, by axial compression or expansion of the transverse slots 308 relative to the spine 310.

A distal aperture 314 is in communication via a central lumen 316 with the proximal end of the steerable and curvable injector 300. Any of a variety of tip configurations may be used such as those disclosed elsewhere herein. The proximal end of the central lumen 316 may be provided with a luer connector, or other connection port to enable connection to a source of media such as bone cement to be infused. In the illustrated embodiment, the aperture 314 faces distally from the steerable and curvable injector 302, although other exit angles may be used as will be discussed below.

The steerable and curvable injector 300 is optionally provided with a cavity forming element 320, such as an inflatable balloon 322. In the illustrated embodiment, the inflatable balloon 322 is positioned in the vicinity of the steerable and curvable distal section 306. Preferably, the axial length of a distal leading segment 307 is minimized, so that the balloon 322 is relatively close to the distal end of the steerable and curvable injector 300. In this embodiment, the plurality of transverse slots 308 are preferably occluded, to prevent inflation media from escaping into the central lumen 316 or bone cement or other injectable media from escaping into the balloon 322. Occlusion of the transverse slots 308 may be accomplished in any of variety of ways, such as by positioning a thin tubular membrane coaxially about the exterior surface of the tubular body and heat shrinking or otherwise securing the membrane across the openings. Any of a variety of heat shrinkable polymeric sleeves, comprising high density polyethylene or other materials, are well known in the catheter arts. Alternatively, a tubular liner may be provided within the central lumen 316, to isolate the central lumen from the transverse slots 308.

The balloon 322 is secured at a distal neck 309 to the leading segment 307 as is understood in the balloon catheter arts. The distal neck 309 may extend distally from the balloon, as illustrated, or may invert and extend proximally along the tubular body. In either event, the distal neck 309 of the balloon 322 is preferably provided with an annular seal 324 either directly to the tubular body 301 or to a polymeric liner positioned concentrically about the tubular body, depending upon the particular device design. This will provide an isolated chamber within balloon 322, which is in fluid communication with a proximal source of inflation media by way of an inflation lumen 326.

In the illustrated embodiment, the balloon 322 is provided with an elongate tubular proximal neck which extends throughout the length of the steerable and curvable injector 300, to a proximal port or other site for connection to a source of inflation media. This part can be blow molded within a capture tube as is well understood in the balloon catheter arts, to produce a one piece configuration. Alternatively, the balloon can be separately formed and bonded to a tubular sleeve. During assembly, the proximal neck or outer sleeve 328 may conveniently be proximally slipped over the tubular body 301, and secured thereto, as will be appreciated by those of skill in the catheter manufacturing arts.

Referring to FIG. 16C, the inflation lumen 326 may occupy an annular space between the outer sleeve 328 and the tubular body 301. This may be accomplished by sizing the inside dimension of the outer sleeve 328 slightly larger than the outside dimension of the tubular body 301, by an amount sufficient to enable the desired inflation flow rate as will be understood in the art. Alternatively, referring to FIG. 16D, a discrete inflation lumen 326 may be provided while the remainder of the outer sleeve 328 is bonded or snuggly fit against the tubular body 301. This may be accomplished by positioning an elongate mandrel (not illustrated) between the outer sleeve 328 and the tubular body 301, and heat shrinking or otherwise reducing the outer sleeve 328, thereafter removing the mandrel to leave the discrete inflation lumen 326 in place. Alternatively, any of a variety of internal inflation lumen may be devised, within the central lumen 316 of tubular body 301. Other cavity forming elements are illustrated and described, for example, in connection with FIGS. 16E-17J of U.S. Pat. Pub. No. 2009/0299282 A1 to Lau et al., which is hereby incorporated by reference in its entirety.

Referring to FIGS. 17A and 17B, there is illustrated an alternative embodiment in which the distal aperture 314 is provided on a side wall of the tubular body. One or two or three or more distal apertures 314 may be provided in any of the embodiments disclosed herein, depending upon the desired clinical performance. In the illustrated embodiment, the distal aperture 314 is provided on the inside radius of curvature of the steerable and curvable section 306, as illustrated in FIG. 17B. The aperture 314 may alternatively be provided on the opposite, outside radius of curvature, depending upon the desired clinical performance.

As a further alternative, the distal aperture or apertures 314 may be provided in any of a variety of configurations on a distal cap or tip, adapted to be secured to the tubular body.

The steerable and curvable injection systems described above are preferably used in conjunction with a mixing and dispensing pump for use with a multi-component cement. In some embodiments, a cement dispensing pump is a hand-held device having an interface such as a tray or chamber for receiving one or more cartridges. In one embodiment, the pump is configured to removably receive a double-barreled cartridge for simultaneously dispensing first and second bone cement components. The system additionally includes a mixing chamber, for mixing the components sufficiently and reproducibly to fully automate the mixing and dispensing process within a closed system.

Bone cement components have conventionally been mixed, such as by hand, e.g., in mixing bowls in the operating room, which can be a time-consuming and unelegant process. The devices disclosed herein may be used with conventional bone cement formulations, such as manually mixed liquid-powder PMMA formulations. Alternatively, the use of a closed mixing device such as a double-barreled dispensing pump as disclosed herein is highly advantageous in reducing bone cement preparation time, preventing escape of fumes or ingredients, ensuring that premature cement curing does not occur (i.e., the components are mixed immediately prior to delivery into the body), and ensuring adequate mixing of components.

Two separate chambers contain respective materials to be mixed in a specific ratio. Manual dispensing (e.g., rotating a knob or squeezing a handle) forces both materials into a mixing nozzle, which may be a spiral mixing chamber within or in communication with a nozzle. In the spiral mixing nozzle, all or substantially all mixing preferably occurs prior to the bone cement entering the steerable and curvable injection needle and, subsequently, into the vertebra. The cement dispensing hand pump may be attached to the steerable and curvable injection needle permanently, or removably via a connector, such as slip-ring Luer fittings. A wide range of dispensing pumps can be modified for use with the present invention, including dispensing pumps described in, for example, U.S. Pat. Nos. 5,184,757, 5,535,922, 6,484,904, and Patent Publication No. 2007/0114248, all of which are incorporated by reference in their entirety.

Currently favored bone cement compositions are normally stored as two separate components or precursors, for mixing at the clinical site shortly prior to implantation. As has been described above, mixing of the bone cement components has traditionally been accomplished manually, such as by expressing the components into a mixing bowl in or near the operating room. In accordance with the present invention, the bone cement components may be transmitted from their storage and/or shipping containers, into a mixing chamber, and into the patient, all within a closed system. For this purpose, the system of the present invention includes at least one mixing chamber positioned in the flow path between the bone cement component container and the distal opening on the bone cement injection needle. This permits uniform and automated or semi-automated mixing of the bone cement precursors, within a closed system, and thus not exposing any of the components or the mixing process at the clinical site.

Thus, the mixing chamber may be formed as a part of the cartridge, may be positioned downstream from the cartridge, such as in-between the cartridge and the proximal manifold on the injection needle, or within the proximal manifold on the injection needle or the injection needle itself, depending upon the desired performance of the device. The mixing chamber may be a discrete component which may be removably or permanently coupled in series flow communication with the other components of the invention, or may be integrally formed within any of the foregoing components.

In general, the mixing chamber includes an influent flow path for accommodating at least two bone cement components. The first and second incoming flow path are combined, and mixing structures for facilitating mixing of the components are provided. This may include any of a variety of structures, such as a helical flow path, baffles and or additional turbulence inducing structures.

Tables 1-2 below depict the contents and concentrations of one exemplary embodiment of bone cement precursors. Chambers 1A and 1B contain precursors for a first cement composition for distribution around the periphery of the formed in place vertebral body implant with a higher particle concentration to promote osteoinduction, as discussed previously in the application. Chambers 2A and 2B contain precursors for a second cement composition for expression more centrally within the implanted mass within the vertebral body, for stability and crack arresting, as discussed previously in the application.

One of ordinary skill in the art will recognize that a wide variety of chamber or cartridge configurations, and bone cements, can be used with the present injection system. For example, in one embodiment, a first cartridge includes pre-polymerized PMMA and a polymerization catalyst, while a second cartridge includes a liquid monomer of MMA as is common with some conventional bone cement formulations.

In some embodiments, the contents of two cartridges can be combined into a single cartridge having multiple (e.g., four) chambers. Chambers may be separated by a frangible membrane (e.g., 1A and 2A in a first cartridge and 1B and 2B in a second cartridge, each component separated by the frangible membrane or other pierceable or removable barrier). In other embodiments, contents of the below cartridges can be manually pre-mixed and loaded into the input port of the injection system without the use of a cement mixing dispenser.

TABLE 1

| Chamber 1A | |
|---|---|
| Methyl methacrylate (balance) | Hydroquinone (~75 ppm) (stabilizer) |
| N,N-dimethyl-p-toluidine (~0.9%) (catalyst for polymerization) | Sterile bone particles (≥35 wt. %) |
| Barium sulfate (~20 wt. %) (radio-opacifier) | |
| Chamber 1B | |
| Benzoyl peroxide (~2%) (activator for polymerization) | Physiological saline or poppy seed oil (balance) |

TABLE 2

| Chamber 2A | |
|---|---|
| Methyl methacrylate (balance) | Hydroquinone (~75 ppm) (stabilizer) |
| N,N-dimethyl-p-toluidine (~0.9%) (catalyst for polymerization) | Sterile bone particles (~30 wt. %) |
| Barium sulfate (~20 wt. %) (radio-opacifier) | |
| Chamber 2B | |
| Benzoyl peroxide (~2%) (activator for polymerization) | Physiological saline or poppy seed oil (balance) |

As illustrated in FIGS. 18A and 18B, in one embodiment, a system or kit for implanting bone cement includes at least some of the following components: a stylet configured to perforate a hole into the pedicle of the vertebral body; an introducer cannula 800 for providing an access pathway to the treatment site, a steerable and curvable injection needle 700 to deliver bone cement to a desired location, and, a cement dispensing pump 811 preferably configured to accommodate one or two or more dual chamber cartridges 1200 as well as a mixing nozzle 995.

The stylet may have a diameter of between about 0.030" to 0.300", 0.050" to about 0.200" and preferably about 0.100" in some embodiments. The introducer cannula 800 is between about 8-14 gauge, preferably between about 10-12 gauge, more preferably 11 gauge in some embodiments. The introducer cannula 800, which may be made of any appropriate material, such as stainless steel (e.g., 304 stainless steel) may have a maximum working length of no more than about 12", 8", or 6" in some embodiments. One or two or more bone cement cartridges, each having one or two or more chambers, may also be provided. Various other details of the components have been described above in the application.

One embodiment of a method for delivering bone cement into a vertebral body is now described, and illustrated in FIGS. 19A-F. The method involves the general concept of vertebroplasty and kyphoplasty in which a collapsed or weakened vertebra is stabilized by injecting bone cement into cancellous bone.

Figure 19A:
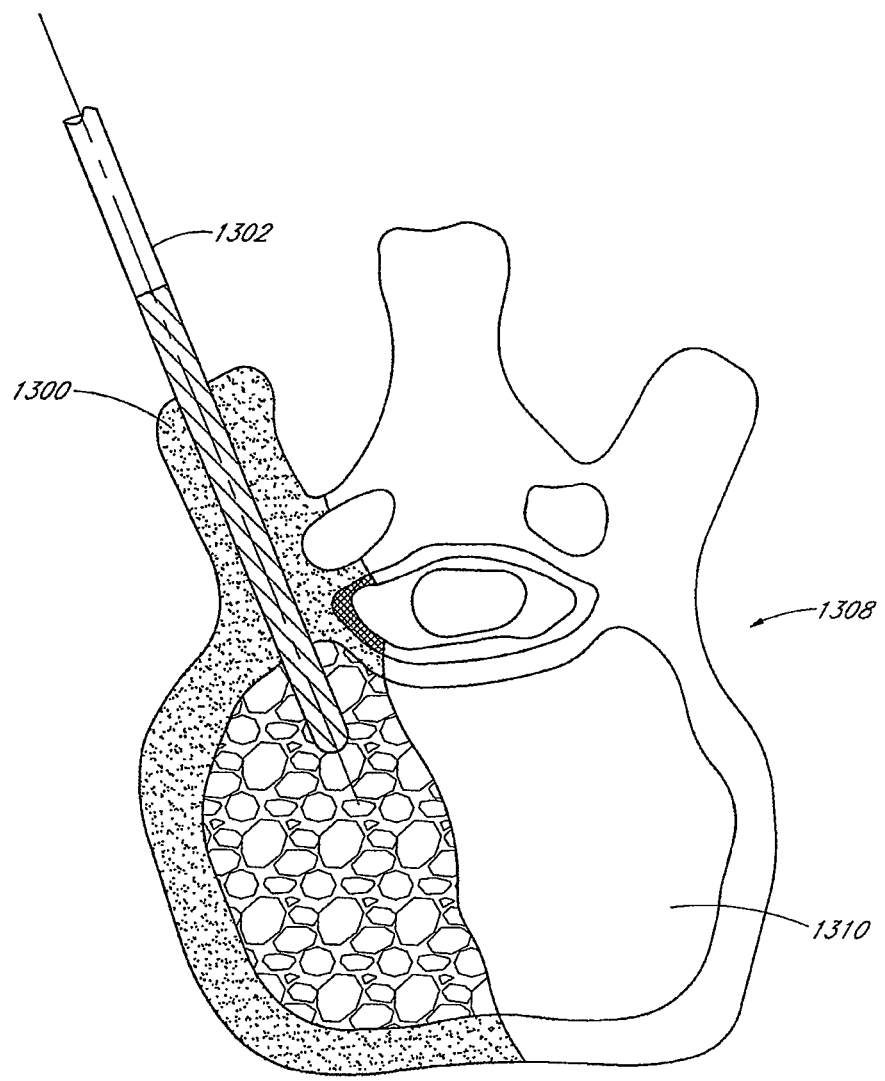
FIGS. 19A through 19F show stages in the method of accomplishing vertebroplasty in accordance with the present invention.
Figure 19B:
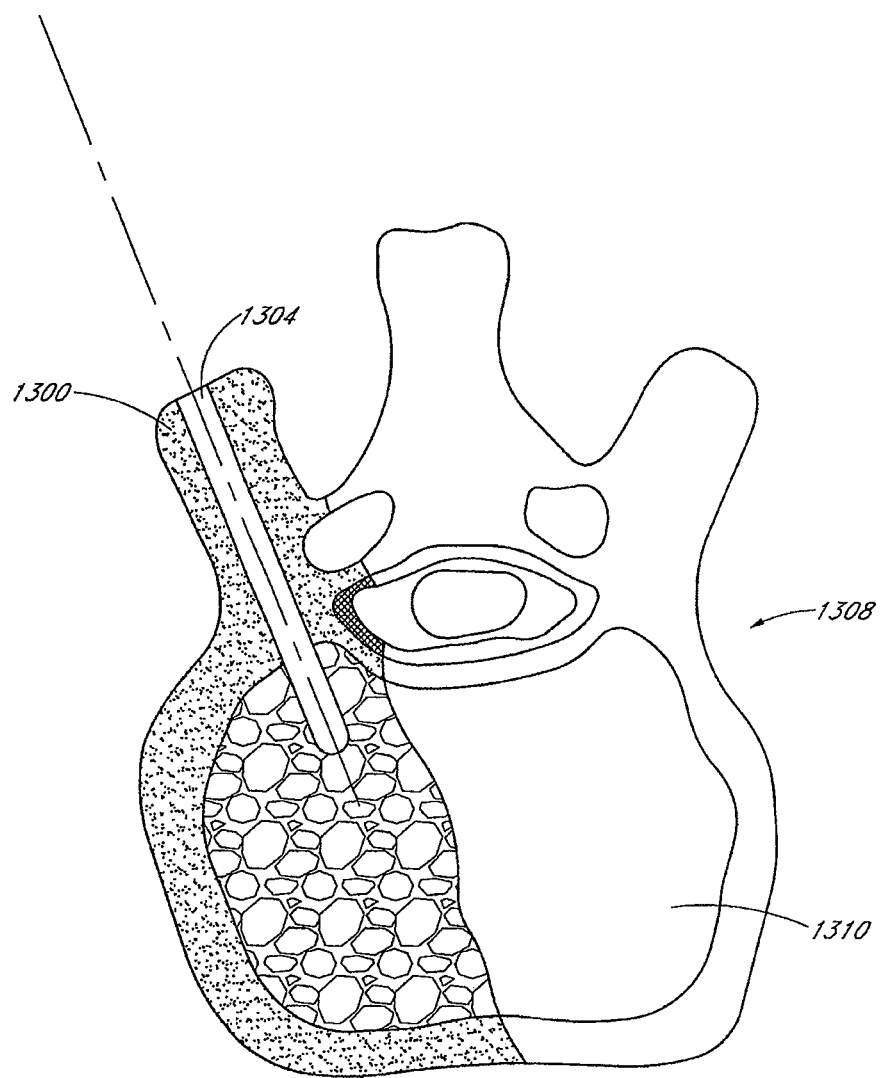
Figure 19C:
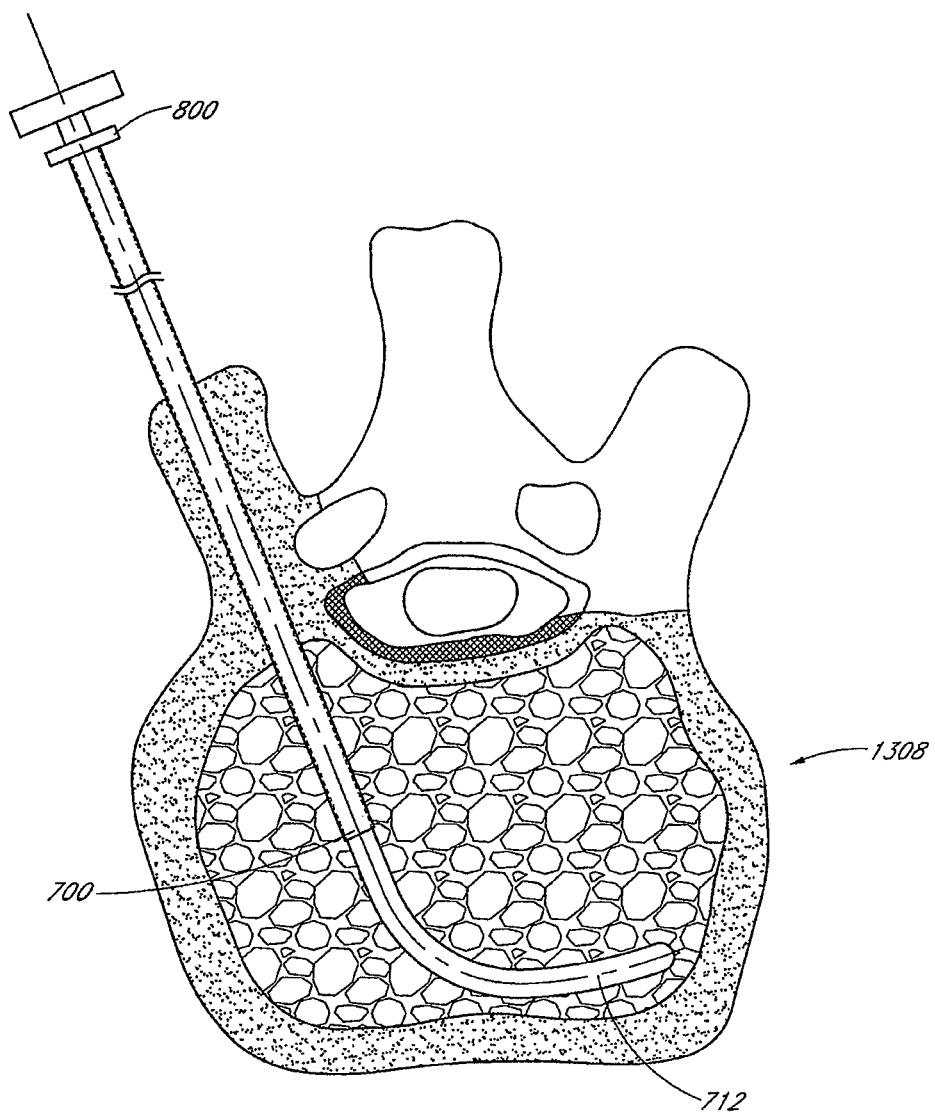

The cement implantation procedure is designed for uni-transpedicular access and generally requires either a local anesthetic or short-duration general anesthetic for minimally invasive surgery. Once the area of the spine is anesthetized, as shown in FIGS. 19A-B, the physician inserts a stylet 1302 to perforate a lumen 1304 into the pedicle wall 1300 of the vertebra 1308 to gain access to the interior of the vertebral body 1310. As illustrated in FIG. 19C, the introducer cannula 800 is then inserted through the lumen 1304 for bone access as well as acting as the guide for the steerable and curvable injection needle 700. The introducer cannula 800 is sized to allow physicians to perform vertebroplasty or kyphoplasty on vertebrae with small pedicles 1300 such as the thoracic vertebra (e.g., T5) as well as larger vertebrae. In addition, this system and method is advantageously designed to allow uni-transpedicular access as opposed to bi-pedicular access, resulting in a less invasive surgical procedure.

Once bone access has been achieved, as shown in FIG. 19C the steerable and curvable injection needle 700 such as any of the devices described above can be inserted through the introducer cannula 800 and into the vertebra 1308. The entire interior 1310 of the target vertebral body may be accessed using the steerable and curvable injection needle 800. The distal end 712 of the needle 700 can be laterally deflected, rotated, and/or proximally retracted or distally advanced to position the bone cement effluent port at any desired site as previously described in the application. The radius can be adjusted by means of an adjustment control, such as a knob on the proximal end of the device as previously described.

Figure 19D:
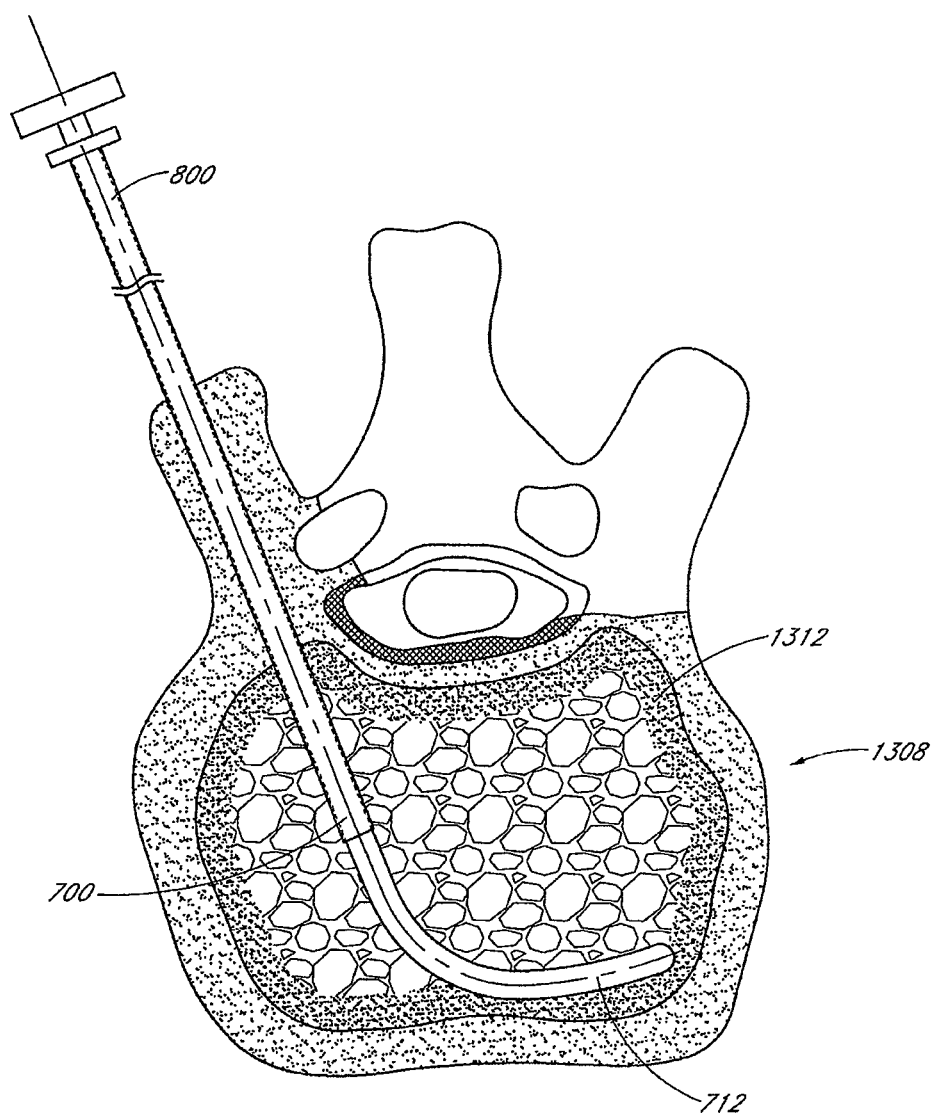
Figure 19E:
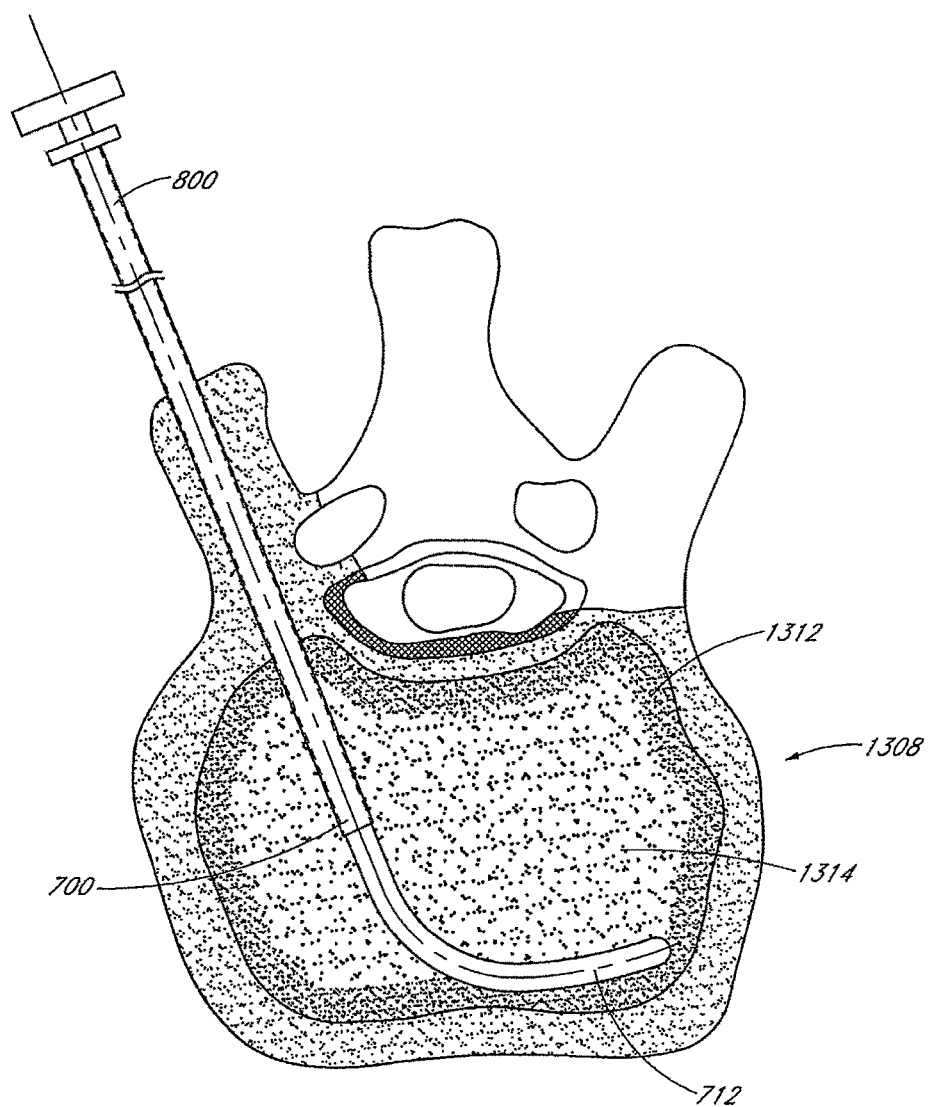

The actual injection procedure may utilize either one or two basic steps. In a one step procedure, a homogenous bone cement is introduced as is done in conventional vertebroplasty. The first step in the two step injection involves injection of a small quantity of PMMA with more than about 35%, e.g., 60% particles such as inorganic bone particles onto the periphery of the treatment site, i.e., next to the cortical bone of the vertebral body as shown in FIG. 19D. This first cement composite 1312 begins to harden rather quickly, forming a firm but still pliable shell, which is intended to minimize or prevent any bone marrow/PMMA content from being ejected through any venules or microfractures in the vertebral body wall. The second step in the procedure involves an injection of a bolus of a second formulation of PMMA with a smaller concentration such as approximately 30% inorganic bone particles (second cement composite 1314) to stabilize the remainder of the weakened, compressed cancellous bone, as illustrated in FIG. 19E.

Figure 19F:
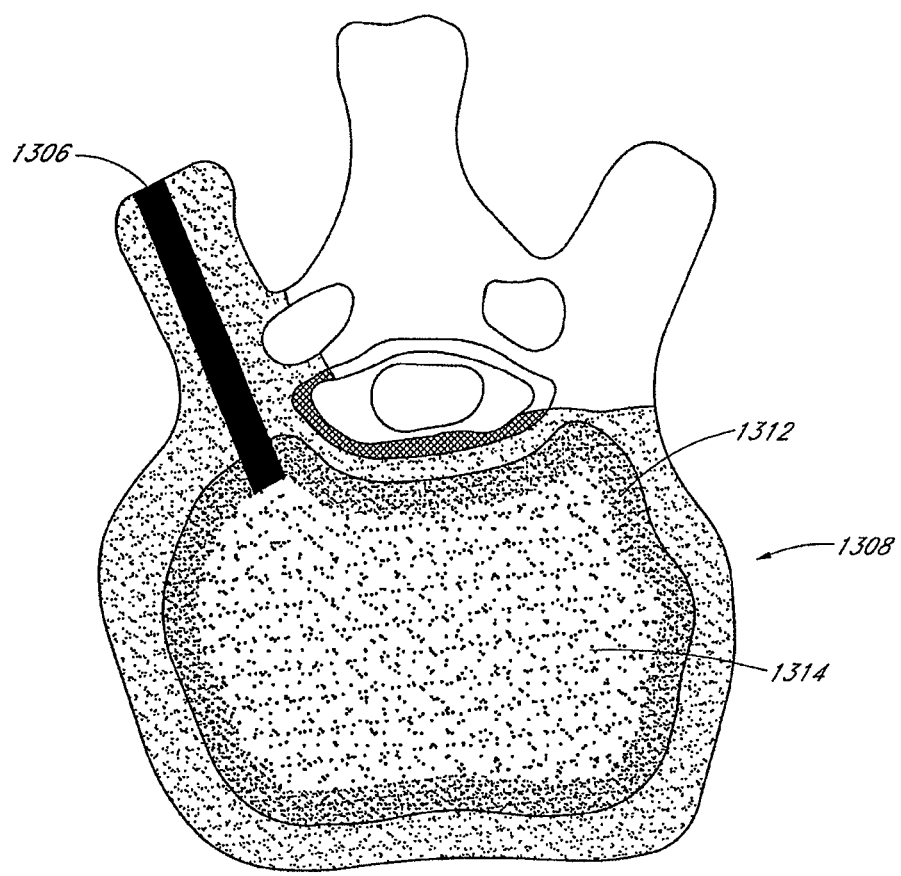

Injection control for the first and second steps is provided by an approximately 2 mm inside diameter flexible introducer cannula 800 coupled to a bone cement injection pump (not shown) that is preferably hand-operated. Two separate cartridges containing respective bone cement and inorganic bone particle concentrations that are mixed in the 60% and 30% ratios are utilized to control inorganic bone particle to PMMA concentrations. The amount of the injectate is under the direct control of the surgeon or interventional radiologist by fluoroscopic observation. The introducer cannula 800 is slowly withdrawn from the cancellous space as the bolus begins to harden, thus preventing bone marrow/PMMA content from exiting the vertebral body 1308. The procedure concludes with the surgical incision being closed, for example, with bone void filler 1306 as shown in FIG. 19F. Both the high and low bone cement particle concentration cement composites 1312, 1314 harden after several minutes. In vitro and in vivo studies have shown that the 60% bone-particle impregnated bone cement hardens in 2-3 minutes and 30% bone-particle impregnated bone cement hardens between 4 to 10 minutes.

The foregoing method can alternatively be accomplished utilizing the combination steerable and curvable needle of FIG. 16A, having a cavity formation structure 320 thereon. Once the steerable and curvable injector 300 has been positioned as desired, such as either with deflection as illustrated in FIG. 19C, or linearly, the cavity forming element 320 is enlarged, such as by introducing inflation media under pressure into the inflatable balloon 322. The cavity forming element 320 is thereafter reduced in cross sectional configuration, such as by aspirating inflation media from the inflatable balloon 322 to produce a cavity in the adjacent cancellous bone. The steerable and curvable injector 300 may thereafter by proximally withdrawn by a small distance, to position the distal opening 314 in communication with the newly formed cavity. Bone cement or other media may thereafter be infused into the cavity, as will be appreciated by those skill in the art.

At any time in the process, whether utilizing an injection needle having a cavity formation element or not, the steerable and curvable injector may be proximally withdrawn or distally advanced, rotated, and inclined to a greater degree or advanced into its linear configuration, and further distally advanced or proximally retracted, to position the distal opening 314 at any desired site for infusion of additional bone cement or other media. More than one cavity, such as two, or three or more, may be sequentially created using the cavity formation element, as will be appreciated by those of skill in the art.

The aforementioned bone cement implant procedure process eliminates the need for the external mixing of PMMA powder with MMA monomer. This mixing process sometimes entraps air in the dough, thus creating porosity in the hardened PMMA in the cancellous bone area. These pores weaken the PMMA. Direct mixing and hardening of the PMMA using an implant procedure such as the above eliminates this porosity since no air is entrapped in the injectate. This, too, eliminates further weakening, loosening, or migration of the PMMA.

Steerable, Curvable Vertebroplasty Drill

Also disclosed herein is a steerable and curvable drill that can be used to drill through tissue, such as bone, in a wide variety of applications including vertebroplasty or kyphoplasty. In some embodiments, prior to or concurrent with an orthopedic procedure such as vertebroplasty or kyphoplasty, it may be advantageous to remove bone, such as sclerotic cancellous bone, in order to facilitate adequate filling of the interior of a vertebral body with bone cement or to create or enhance cavity formation in a kyphoplasty procedure. Systems, devices, and methods to facilitate removal of such tissue such as sclerotic cancellous bone will now be described.

Referring to FIG. 20A, disclosed is a perspective view of a steerable and curvable drill 900 in accordance with one embodiment of the invention. Drill 900 has an elongate body including a proximal handle portion 1000 and an elongate member 902. One or more boring elements 919 such as a drill bit can be operably connected to the distal end of the elongate member 902 in order to drill through a tissue such as cortical or cancellous bone. The distal elongate member 902 includes, in some embodiments, a relatively rigid proximal end or segment 924 and a distal deflectable segment 923 separated by a transition point 930 defining where the distal end or portion 923 is configured to be deflectable. The proximal segment 924 can be relatively straight and coaxial with the long axis of the proximal handle portion 1000. The distal segment 923 can be configured to be steerable and curvable through a working range via actuation of a control on the handle 1000 that can be as described in detail supra in the application, such as, for example, at FIGS. 4-5, 9A-10C and the accompanying disclosure. As described elsewhere herein, the lateral flexibility of the distal section 923 may be accomplished in any of a variety of ways, such as by the provision of a plurality of transverse chevrons or slots. Slots may be machined or laser cut into appropriate tube stock, such as stainless steel or any of a variety of rigid polymers. Slots oppose a column strength element such as an axially extending spine, for resisting axial elongation or compression of the device. The proximal handle portion 1000 can include a manual or motor driven drill control 913 for actuating (e.g., rotating) the drill bit to cut through tissue and an adjustment control (e.g., rotation of 901) to adjust the curvature of the distal segment 923 of the elongate member 902 throughout a working range.

Figure 20C:
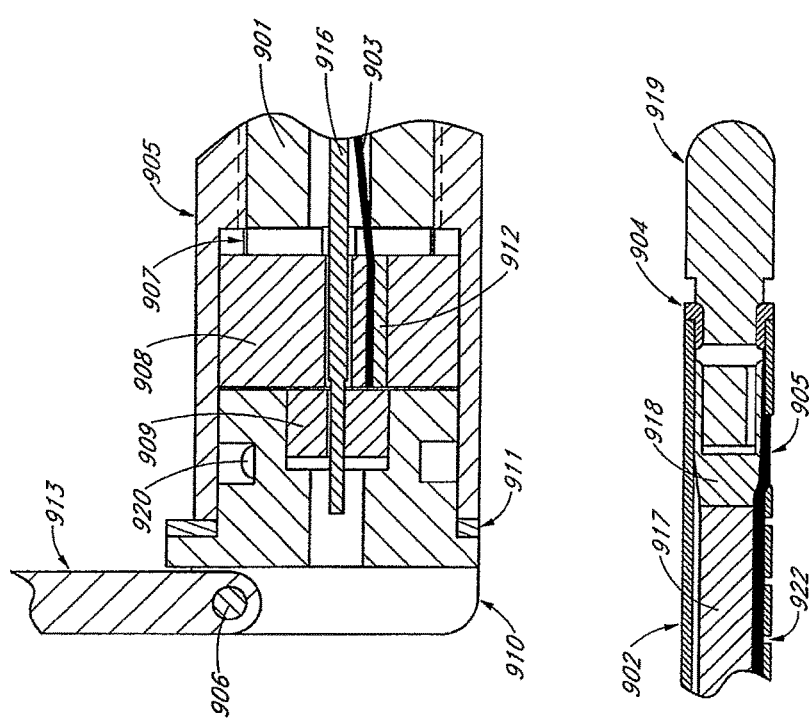
Figure 20D:
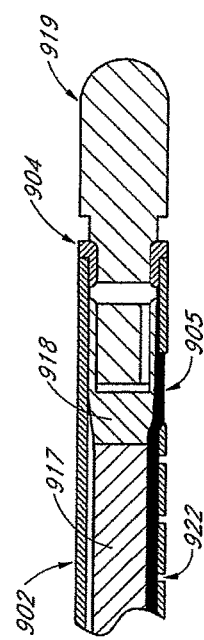

FIG. 20B is a cross-sectional view of the steerable and curvable drill of FIG. 20A. FIG. 20C is a cross-sectional close-up view of the proximal handle, and FIG. 20D is a cross-sectional close-up view of the distal end as shown in FIG. 20B. As illustrated, certain embodiments of the drill include a mid-handle 905 and front handle 901 attached to an elongate member 902, such as a laser cut tube with a curvable segment 923 projecting distally therefrom. Extending beyond the distal end 923 of the elongate member 902 is a drill element 919 that is operably coupled to a drill control 914 located at the proximal end of the device via a drive shaft 916. Actuation of the drill control 914, such as by rotating a handle rotates the drill tip 919 thereby facilitating drilling of the steerable and curvable drilling device into bone. The drill actuator 914 can be a handle lever as shown, or alternatively a variety of other types of control mechanisms, such as a rotatable member, such as a thumb wheel or dial. Alternative controls include, for example, rotatable knobs, slider switches, compression grips, triggers such as on a gun grip handle, or other depending upon the desired functionality.

In some embodiments, as illustrated, rotation of the front handle 901 relative to the mid-handle 905 increases the tension on one or more internal pull wires 903 that can exert a force on the distal end of the laser cut tube 923 and thereby adjust the curvature of the distal segment 923 thus defining an angle between the longitudinal axis of the proximal portion 924 of the elongate member 902 and the longitudinal axis of the distal segment 923 of the elongate member 902.

As illustrated in FIG. 20C, the proximal handle portion 1000 of the steerable and curvable drill can include a first handle portion 901 and a second handle portion 905, e.g., a front handle 901 and a mid-handle 905. In some embodiments, the front handle 901 and mid-handle 905 are separated by a washer 907. Said washer 907 has a central lumen through which the drill shaft 916 can pass therethrough. In addition, some embodiments of the washer 907 can have additional lumens through which the pull wire 903 can pass therethrough. In some embodiments, these components can be sized and configured to allow for simple and ergonomic manipulation and control by the operator. Non-limiting embodiments of dimension ranges for various components will now be disclosed. In some embodiments, the diameter of the front handle 901 could range from 0.5 inches to 2 inches and the length can be from 2 inches to 6 inches. In some embodiments, the diameter of the mid-handle 905 can generally range from 0.5 inches to 2 inches and the length can be approximately 6 inches. In some embodiments, the elongate member 902 has a lumen configured to house the drill bit and drive shaft and can generally have an external diameter between 0.06 inches to 0.3 inches. In some embodiments, the overall length of the elongate member 902 can generally range between 4 inches to 12 inches. In some embodiments, the proximal portion of the laser cut tube 924 will be relatively rigid; however the distal portion 923 is flexible and can be deflected to an angle relative to the proximal portion 924. In some embodiments, the distal flexible portion 923 of the elongate member 902 can comprises at least about 10, 15, 20, 25, 30 percent or more of the length of the distal elongate member 902.

In some embodiments, the elongate member 902 of the drill 900 may have an outside diameter of between about 8 to 24 gauge, more preferably between about 10 to 18 gauge, e.g., 12 gauge, 13 gauge (0.095" or 2.41 mm), 14 gauge, 15 gauge, or 16 gauge. In some embodiments, the inside diameter (luminal diameter) is between about 9 to 26 gauge, more preferably between about 11 to 19 gauge, e.g., 13 gauge, 14 gauge, 15 gauge, 16 gauge, or 17 gauge. In some embodiments, the inside diameter is no more than about 4 gauge, 3 gauge, 2 gauge, or 1 gauge smaller than the outside diameter of the elongate member 902.

The inside luminal diameter of all of the embodiments disclosed herein is preferably optimized to allow a minimal exterior delivery profile while maximizing the space for the drive shaft 916. In one embodiment, the outside diameter of the elongate member 902 is 13 gauge (0.095" or 2.41 mm) with a 0.077" (1.96 mm) lumen. In some embodiments, the percentage of the inside diameter of the lumen with respect to the outside diameter of the elongate member 902 is at least about 60%, 65%, 70%, 75%, 80%, 85%, or more.

In some embodiments, the maximum length of the drill 900 is no more than about 15", 10", 8", 7", 6", or less depending upon the target and access pathway. In one embodiment, when the length of drill 900 is no more than about 8", the adjustable distal portion 923 of the elongate member 902 has a length of at least about 1" and preferably at least about 1.5" or 2" or more.

To operate the drill, the operator actuates the drill control, such as by moving the handle lever 913 and attached crank knob 914 (similar to that of a fishing reel) in an appropriate direction thereby rotating the operably coupled actuation knob 910 operably connected to the drill bushing 908, which in turn rotates the drive shaft 916 and ultimately the drill tip 919. The crank knob 914 is attached to the handle lever 913 using a screw 921 or other method of attachment. In some embodiments, handle lever 913 and crank knob 914 can be integrally formed. In some embodiments, the presence of a friction-reducing element such as a Teflon washer 915 reduces friction between the crank knob 914 and handle lever 913 while these components are in motion. In some embodiments, the handle lever 913 with associated crank knob 914 is sized and positioned so that it may be easily manipulated and rotated with one hand while the operator can stabilize the proximal end of the steerable and curvable vertebroplasty drill 900 with the other hand. While the drill 900 is described herein as manually operable, motorized drills are also within the scope of the invention.

The actuating knob 910 is operably coupled to a drive bushing 909 which rotates a drive shaft 916 in the vicinity of the mid-handle 905. The actuating knob 910 can be secured to the mid-handle 905 with one or more dowel pins 920 that enable the actuating knob 910 to rotate freely around the axis of the mid-handle 905. Likewise, the operably coupled drive shaft 916 and drive bushing 909 can rotate axially relative to the mid-handle 905 when the operator turns the handle lever 913 attached to the crank knob 914. In some embodiments, a friction reducing element such as one or more Teflon washers 911 reduce friction between the actuating knob 910 and the mid-handle so as to facilitate the free rotation of the actuating knob 910 relative to the mid-handle 905.

As illustrated in FIGS. 20C and/or 20D, the drive shaft 916 passes through a lumen in drive bushing 909 near the center of the mid-handle 905 and front handle 901 and extends distally through the central lumen of the proximal portion of the tube 924. The drive shaft 916 can be operably coupled to a more distal flexible shaft 917 at a point near the beginning of the deflectable distal portion 923 of the elongate member 902 and configured to be sufficiently flexible to also bend when distal portion 923 of the drill is deflected without damaging the flexible shaft 917. In some embodiments, the proximal drive shaft 916 and distal drive shaft 917 (also referred to herein as the flex shaft 917) are integrally formed with the distal drive shaft 917 being thinner or made of a material to increase flexibility such that it is capable of bending along with the distal portion of the laser cut tube 923 and capable of transmitting torque while in a straight or curved configuration. The drive shaft including flex shaft 917 may be made of a polymer, PTFE, ePTFE, stainless steel, Nitinol, or other appropriate material. The drive shaft 916 and flex shaft 917 rotate in unison within the lumen of the elongate member 902.

As illustrated in FIG. 20D, the flex shaft 917 is, in turn, operably coupled to a distal shaft end 918. The distal shaft end 918 is operably coupled to the drill tip 919 and can transmit the torque of the rotating flex shaft 917 thereto. In some embodiments, the drill tip 919 may be operably coupled to the distal shaft end 918 by fitting a shaped projection of the drill tip 919 into a corresponding groove on the distal shaft end 918 so that the two components rotate together. Other complementary connectors such as a male-female attachment system, e.g., a threaded drill tip 919 configured to fit within a threaded shaft within distal shaft end 918 can be used as well In other embodiments, these two components are integrally formed.

The drill tip 919 is positioned so that, in use it extends at least partially beyond the distal end of the distal elongate member 902 of the drill. This enables the drill tip 919 to bore through the desired bone or other tissue. While described herein as a drill bit, burrs, augurs, abraders, cutters, or other elements configured to rotate at a suitable speed to bore through cancellous and/or cortical bone or other tissue can be used as well in the invention. For example, various cutters as described, for example in paragraphs [0039] to [0043] of U.S. Pat. Pub. No. 2006/0149268 A1 to Truckai et al., hereby incorporated by reference in its entirety, can be used with embodiments of the disclosed drill instead of a drill bit. While some embodiments of the steerable and curvable vertebroplasty drill 900 will have a permanently fixed drill tip 919 set at the point of manufacture, in other embodiments the drill tip 919 is detachable so that an alternate drill tip 919 may be substituted in the operating room depending on the desired clinical result.

The drill tip 919 can be secured, such as via a half bushing 904 at or near the distal end of the laser cut tube 923. The proximal portion of drill tip 919 is positioned within the distal portion 923 of the elongate member 902 and operably coupled with the distal shaft end 918 as noted above. In some embodiments, the drill tip 919 has a diameter greater than that of the lumen at the location of the half bushing 904. In such embodiments, there is a depression or groove around the circumference of the lateral surface of the drill tip 919 wherein the half bushing 904 can fit in a complementary manner. This configuration can limit any possible axial motion while not impeding the rotation of said drill tip 919.

In some embodiments, the distal portion 923 of the elongate member 902 may have a curved bias, and kept in a relatively straightened configuration by an outer tubular member having column strength sufficient to keep the distal segment in 923 in a relatively straightened position while the outer tubular member encompasses the distal end 923 of the elongate member 902, as described, for example, in connection with FIGS. 9A-10C above. Withdrawal of the outer tubular member will result in the distal portion 923 of the tube assuming its curved state. In some embodiments, this bias can be achieved by constructing the elongate member 902, or at least the distal part thereof 923, out of Nitinol, Elgiloy, stainless steel or a biocompatible, superelastic shape memory alloy or polymer.

In order to facilitate the deflection of the distal end of the laser cut tube 923, this portion of the device can include a plurality of transverse slots 922 cut into a portion of or the entire circumference of the laser cut tube 923. These slots 922 can be machined or laser cut out of the tube stock that becomes the elongate member 902. In some embodiments, these slots 922 can have a linear, chevron-shape or other configuration. In some embodiments, the distal end of the laser cut tube 923 may be created from an elongate coil rather than a continuous tube so as to facilitate flexibility. In other embodiments, the distal end of the laser cut tube may comprise a combination of a coil along with a slotted tubular structure.

FIGS. 21A-D illustrate additional features of the steerable and curvable drill 900 according to some embodiments on the invention. FIGS. 21A-D show a cross-section of the proximal handle 1000 as well as the distal portion 923 of the elongate member 902 of the device with the mid-portion of the drill omitted for clarity. As illustrated, the drill 900 has an axially "floating" drive shaft 916 that can advantageously keep the drill tip 919 and drive shaft 916 properly positioned and operably coupled with the actuating knob 910 when the overall length of the proximal handle 1000 is increased. FIG. 21A illustrates the device when the longitudinal axis of the distal elongate segment 923 is substantially coaxial with the longitudinal axis of the handle 1000 and proximal segment 924 of the elongate member 902. FIGS. 21B-D illustrate various elements of the drill 900 as the distal segment 923 of the elongate member 902 deflects throughout a progressively increasing angular range.

As shown, when the front handle 901 is rotated relative to the mid-handle 905, these two components will move apart axially from one another opening a progressively expanding gap D1 to D3 between these two components and thus increasing the overall length of the proximal handle 1000. In some embodiments, the front handle 901 and mid-handle 905 articulate by means of complementary, screw-like, threaded surfaces so that rotation in one direction moves the two components apart while rotation in the opposite direction moves them closer together thereby decreasing the axial gap distance (e.g., from D3 until front handle 901 and mid-handle 905 abut each other). In alternative embodiments, instead of rotation of the mid handle 905 and/or front handle 901, a ratcheting system with stops or other mechanism could be used to separate the components. In some embodiments, the maximal distance D3 that the mid-handle 905 is configured to move axially proximally relative to front handle 901 is at least about 1 cm, 2 cm, 3 cm, 4 cm, 5 cm, or more. In some embodiments, the maximal distance D3 is at least about 2%, 3%, 5%, 8%, 10%, 15%, 20%, 25%, 30%, or more of the total axial length of the drill.

In many embodiments, the deflection of the distal end 923 of the elongate member 902 is controlled by adjusting the tension exerted by the pull wire 903. The distal end of the pull wire 903 is attached to the half bushing 904 located near the distal end of the elongate member 902. The proximal end of the pull wire 903 is attached to the drill bushing 908 and held secure by, for example, a tapered dowel pin 912. As the distance D1 to D3 between the front handle 901 and mid-handle 905 increases, the tension exerted by the proximally attached pull wire 903 on the distal half bushing 904 increases. The tension can deflect the flexible distal elongate segment 923 to an angle relative to the rigid, coaxial, proximal region of the tube 924. Continued rotation of the front handle 901 relative to the mid-handle 905 will progressively enlarge the distance between these components from D1 to D3, thereby increasing the tension exerted by the pull wire 903 on the half bushing 904, and ultimately increase and the angle of deflection of the distal elongate segment 923 of the elongate tube 902.

As shown in FIGS. 21A through 21D, when the overall length of the proximal handle 1000 is increased and the distal deflectable segment 923 of the elongate tube 902 deflects, it is advantageous to keep the drive shaft 916 operably coupled to the actuating knob 910 so that the operator is able to operate the drill. In many embodiments, the continued articulation of these two components is possible by allowing the drive shaft 916 to move axially as the length of the handle 1000 increases. Specifically, as the distance (e.g., D1 to D3) between the front handle 901 and mid-handle 905 increases, the drive shaft 916 is able to move axially toward the distal end of the unit by the same or a similar distance, such as, for example, at least about 1 cm, 2 cm, 3 cm, 4 cm, 5 cm, or more. The drive shaft 916 and the drive bushing 909 are configured so that when the operator rotates the actuating knob 910, the operably coupled drive bushing 909 and drive shaft 916 rotate together. However, while the drive shaft 916 is freely able to slide axially relative to the drive bushing 909, the relative positions of the drive bushing 909 and the actuating knob 910 remain fixed, thereby keeping these two components operably coupled. This axially "floating" arrangement of the drive shaft 906 enables the actuating knob 910 to remain operably coupled to the drive shaft 916 and ultimately the drill tip 919 to compensate for changes in the overall length of the handle 1000.

Figure 22A:
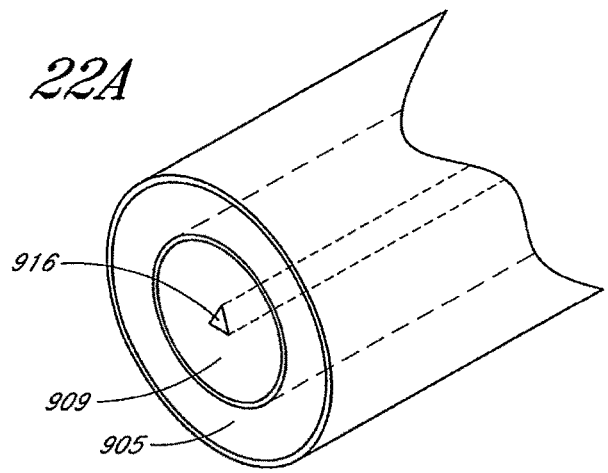
FIG. 22A through 22C schematically illustrate embodiments of the mid-handle and drive bushing with examples of triangular, square, and octagonal central lumens wherein complementary shaped drive shafts can be positioned.
Figure 22B:
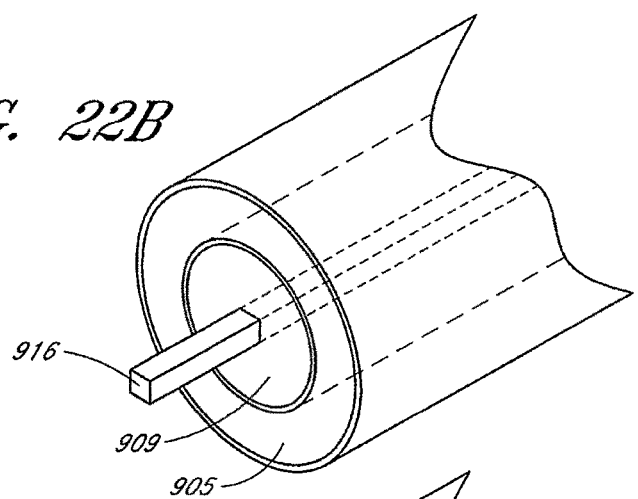
Figure 22C:
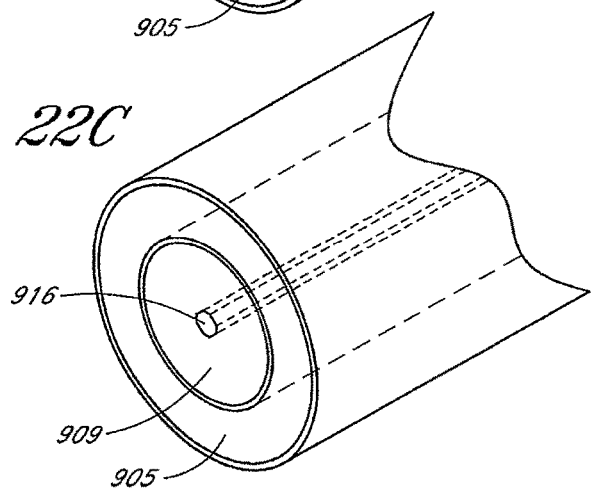

To facilitate the axially "floating" feature, in some embodiments, the drive shaft 916 (and/or the inside diameter lumen of the drive bushing 909) can have a cross-sectional shape other than circular. Such shapes can include, triangular, square, hexagonal, octagonal, star shaped, D shaped or a variety of other configurations. FIGS. 22A through 22C show examples of a drive bushing 909 with central lumens in a triangular, square and octagonal configuration. In such embodiments, the cross-sectional configuration of the drive shaft 916 and the lumen of the drive bushing 909 have complementary surface structures that provide rotational engagement. The interior lumen of the drive bushing 909 and the drive shaft 916 can be respectively configured such that rotation of the drive bushing 909 by the actuation knob 910 in an appropriate direction will rotate the drive shaft 916, while the drive shaft 916 can still move freely axially with respect to the drive bushing 909. As shown in FIG. 22A, the drive shaft 916 can have a triangular cross-sectional shape while the interior lumen of the drive bushing 909 has a complementary triangular cross-sectional shape. Alternatively, as shown in FIG. 22B, the drive bushing 909 can have a square interior cross-sectional lumen while the drive shaft 916 has a similar square cross section. In some embodiments, the entire drive shaft 916 may be the same cross-sectional shape, in other embodiments the cross-section of the more distal portion of the drive shaft 916 can round or a shape different than the proximal section. As shown in FIG. 22A, the drive shaft 916 can have a triangular cross-sectional shape while the interior lumen of the drive bushing 909 has a complementary triangular cross-sectional shape. As further illustrated in FIG. 22C, the drive shaft 916 can have an octagonal cross-sectional shape while the interior lumen of the drive bushing 909 has a similar octagonal cross-sectional shape. As noted above, a variety of other cross-sectional shape configurations are also possible so long as the drive shaft 916 rotates together with the drive bushing 909, but the drive shaft 916 can move freely axially with respect to the drive bushing 909.

In some embodiments, the steerable and curvable vertebroplasty drill 900 can be used to create a cavity in a vertebral body wherein various types of bone cements can be injected as described supra in the application as well as those disclosed in U.S. patent application Ser. No. 11/626,336, filed Jan. 23, 2007, the disclosure of which is hereby incorporated in its entirety herein by reference.

The steerable and curvable vertebroplasty drill 900 can be used to drill into or through bones and tissues other than vertebrae and can be used in a variety of minimally invasive or open surgical applications. In addition, the device can be used for the purpose of cavity creation for the purpose of introducing implants, drugs, chemotherapeutic or radiologic agents. The device can also be used for the purposes of mass reduction of various pathological tissues or bone biopsy. The disclosures herein should not be construed as limiting the possible medical uses of the steerable and curvable vertebroplasty drill 900.

Figure 23A:
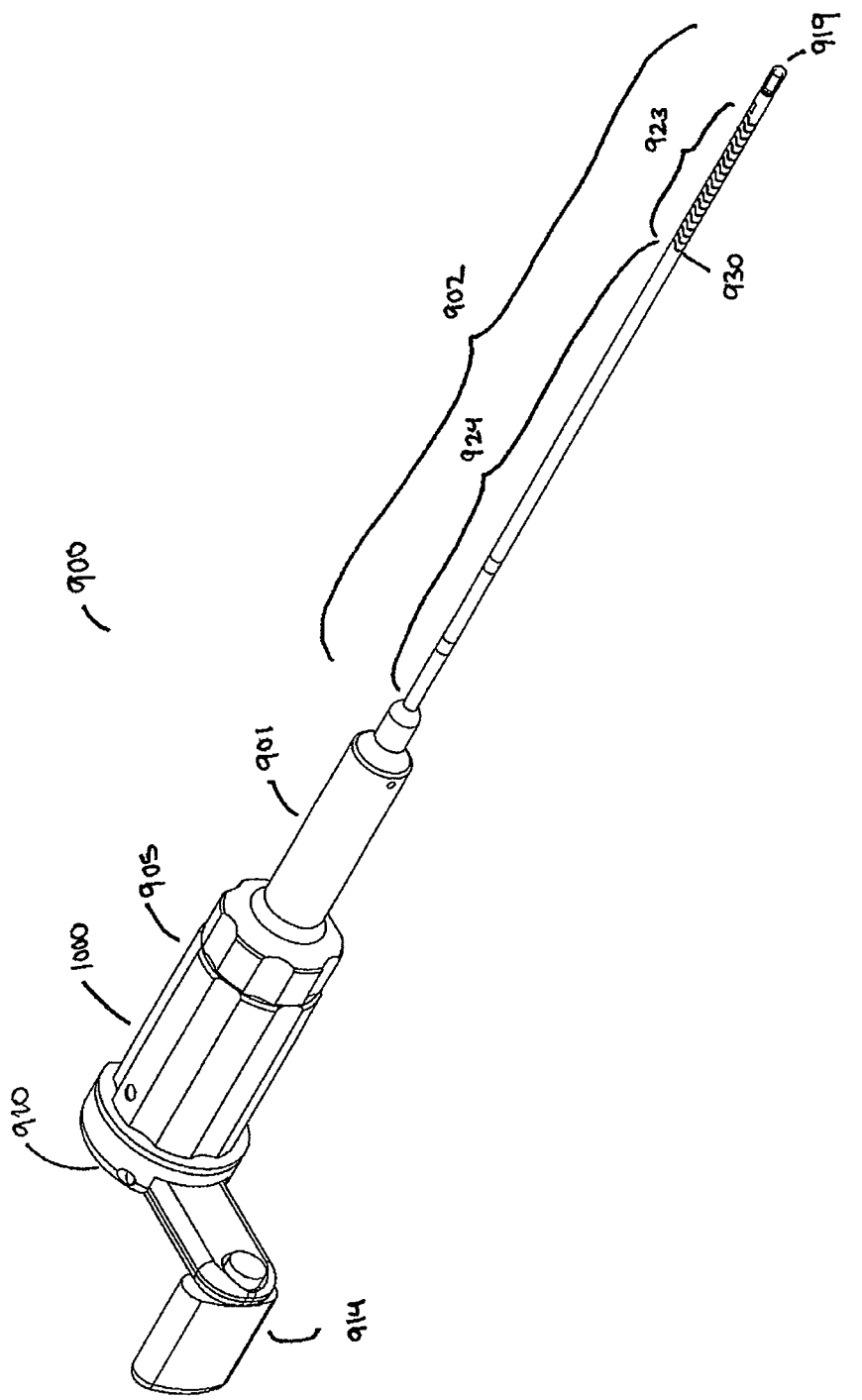

FIGS. 23A and 23B schematically illustrate a steerable and curvable drill 900 somewhat similar to that described and illustrated in connection with FIGS. 20A-20D above, according to one embodiment of the invention. FIG. 23A illustrates a perspective view of the steerable and curvable drill 900 fully assembled, while FIG. 23B illustrates an exploded view of the steerable and curvable drill 900.

The steerable and curvable drill 900 in FIGS. 23A and 23B includes a proximal handle portion 1000, an elongate tubular body member 902, and a boring element 919, such as a drill bit operably connected to the distal end of the elongate member 902. The elongate member 902 also includes a relatively rigid proximal segment 924 and a distal deflectable segment 923 separated by a transition point 930 defining the proximal limit of the deflectable distal segment 923. The handle portion 1000 includes a drill control or actuator 914 operably connected to an actuating knob 910 that rotates the boring element 919 at the drill tip. The handle portion 1000 further includes a deflection control, such as mid-handle 905 and front handle 901 portions, whereby rotation of the front handle 901 relative to the mid-handle 905 proximally retracts one or more internal pull wires to increase the curvature of the distal segment 923.

Additional components come into view in the exploded view of FIG. 23B, including internal pull wire 903, drive shaft 916 and drive shaft insert 975, which is discussed further below with respect to FIGS. 23C through 23F.

FIGS. 23C through 23F schematically illustrate individual components of a steerable and curvable drill having an elongate drive shaft 916 with a proximal end and a distal end. The distal flexible zone 917 is provided with a structural modification to facilitate lateral deflection. In the illustrated design, at least distal zone 917 comprises a tubular sidewall having a helical slit extending through the sidewall so that the sidewall takes on the form of a helically wrapped ribbon or wire. In one embodiment as shown, the slit apertures 972 could be laser-cut, machine cut, or otherwise formed into the drive shaft 916. FIG. 23C is a close-up view of the distal end of the drive shaft 916 illustrated in circled area 23C of FIG. 23D. The slit apertures 972, best illustrated in FIGS. 23C and 23F, could form a helical pattern as shown. A wire insert 975 is configured to be placed within a central lumen of the drive shaft 916 extending at least proximally through the laser cut distal flexible segment 917 of the drive shaft 916, as best shown in FIGS. 23C and 23D. The wire insert 975 advantageously helps to provide radial support for the laser cut distal segment 917 of the drive shaft 916, while allowing the laser cut distal segment 917 to retain its improved flexibility as a result of the helical laser cuts.

In some embodiments, the wire insert 975 is inserted within the central lumen of the drive shaft 916 and extends through a length of the drive shaft that can be at least as long as the length of the portion of the drive shaft 916 having slit apertures 972. While in some embodiments, the wire insert 975 can extend the entire length of the drive shaft 916, in other embodiments, the wire insert 975 extends only a portion of the length of the drive shaft 916. For example, the wire insert 975 can extend a length between about 10% and 70% of the length of the drive shaft 916, or between about 20% and 40% of the length of the drive shaft 916 in some embodiments. The insert 975 could be made of any appropriate material, such as various metals, including nickel, titanium, copper, aluminum, steel, or various alloys thereof. In some embodiments, the wire insert 975 is formed of a flexible biocompatible material, such as Nitinol, MP35N or Elgiloy. High strength, flexible polymeric materials such as polyamide can also be used. In some embodiments, the wire insert 975 can be coated with a material to improve biocompatibility, including phosphorylcholine or polyurethane. In some embodiments, the wire insert has a diameter of from about 0.010 in. to about 0.200 in.

The slit apertures 972 are formed along at least a distal portion of the drive shaft 916, such as between about 0.5 inches to 6 inches, or between about 1 inch to 3 inches of the length of the drive shaft 916. In some embodiments, the slit apertures 972 extend along a length that is at least about 5%, 10%, 15%, 20%, 25%, 30%, or more of the entire length of the drive shaft 916. The drive shaft, in some embodiments, has a sidewall thickness of from about 0.002 in. to about 0.050 in. and an inside diameter of a central lumen in which the wire insert 975 can be placed therethrough of from about 0.010 in. to about 0.200 in. The slit apertures 972 advantageously help to transfer torque along the drive shaft 916, while the drive shaft insert 975 assists in preventing radial collapse of the drive shaft 916 along the length of the slit apertures 972. The direction of the helical filament formed by cutting a slit or wrapping wire or ribbon around a mandrel is matched to the direction of rotation of the drill such that rotation under lead has a tendency to tighten rather than unwind the helical filament. In addition, the slit apertures 972 can help to increase the flexibility of the drive shaft 916 relative to certain drive shafts without the slit apertures. This is particularly useful since the drive shaft 916 can be configured in some embodiments to flex in conjunction with the deflectable distal portion 923 of the elongate member 902. While in some embodiments, the drive shaft 916 is configured to flex when the deflectable distal portion 923 of the elongate member 902 flexes, in other embodiments, the drive shaft 916 can be flexed independently (e.g., such as by its own independent pull wire).

As best shown in FIGS. 23C and 23F, at least one right-hand or left-hand helical laser cut 972 is spaced apart evenly along a length of a distal portion of the drive shaft 916. A single helix configuration is illustrated for clarity. In other embodiments, the helical laser cuts 972 need not be spaced evenly apart from one another. In some embodiments, the laser cut pattern 972 forms a plurality of helices, such as at least a double helix, triple helix, or even a quadruple helix, quintuple helix, or more. In some embodiments, the helix angle for each helix could be between about 15 degrees to about 45 degrees, such as between about 15 degrees to about 30 degrees with respect to a transverse plane which is perpendicular to the longitudinal axis. In some embodiments, the pitch of the crest from a first thread to the crest of a second thread following a complete 360 degree rotation of the screw member is between 0.04" and 0.09", between 0.055" and 0.075", or possibly about 0.065" as shown in FIG. 23F. In other embodiments, pitch values may be below 0.04" or above 0.09" depending on the shape of the laser cuts 972. Providing pitch values as described above advantageously maximize torque transfer.

While the embodiments in FIGS. 23C through 23F illustrate helical patterns, one skilled in the art will appreciate that other non-helical patterns may also be provided that they assist in providing flexibility and transferring torque along the drive shaft 916. Other patterns include a series of chevrons (distally or proximally facing), wavy cuts, or cross-hatch patterns. While these cuts can all be formed by using a laser, it is possible to use other cutting techniques, for example, electrical discharge machining, water cutting or milling. In addition, while the laser cuts 972 are illustrated as a spiral slot extending through the sidewall, in some embodiments, a filler material, such as a thin film polymeric layer can be provided within or over one or more laser cut apertures to provide resilience to the drive shaft 916 if desired.

In some embodiments and as illustrated in FIG. 23E, which is a close-up view of circled area 23E of FIG. 23D, a limit 980 can be provided that serves as a proximal stop for preventing the wire insert 975 from travelling proximally up the drive shaft 916 beyond the limit 980. The limit 980 can be a narrowing (e.g., crimp) or complete termination or localized occlusion of the central lumen of the drive shaft 916 that has a diameter if at all which is less than the diameter of the wire insert 975. By serving as a proximal stop, the limit 980 advantageously limits the wire insert 975 to be positioned around the distal flexible portion of the drive shaft 916 below the helical filaments, without migrating into other sections (e.g., the relatively rigid upper section) of the drive shaft 916.

FIGS. 23G through 23J schematically illustrate an embodiment of a steerable and curvable drill, in which the distal end of the drive shaft 916 is coupled to the boring element 919 via complementary interlocking elements, such as a crimp 1001. FIG. 23G is a close-up view of circled area 23G of FIG. 23H. While in other embodiments, the drill bit may be otherwise coupled to the drill bit via welding, bonding, threaded engagement, etc., use of a crimp interface can be advantageous in some embodiments, to reduce the failure rate of the coupling element, which may be susceptible to cracking if the drive shaft 916 and the boring element 919 are coupled together. Advantageously, the use of a crimp 1001 to secure the drive shaft 916 to the boring element 919 can also facilitate torque transfer from the drive shaft to the boring element, thereby providing an efficient drill. In some embodiments, the amount of torque transferable through the crimp is between about 0.1 lb-ft and 10.0 lb-ft.

In operation, the crimp 1001 is formed of two mateable members, a first crimp member 1024 located on the distal end of the drive shaft 916 and a second crimp member 1028 located on the shaft of the boring element 919. By using the crimp 1001, a secure coupling can be formed between the drive shaft 916 and the boring element 919.

The first and second crimp members are mateable members that secure the drive shaft 916 to the boring element 919. In one embodiment, the first crimp member 1024 and the second crimp member 1028 can include one, two, or more complementary interlocking surfaces. In some embodiments, the first crimp member 1024 includes one, two, or more raised surfaces 1025 or bumps formed on or attached on to the drive shaft 916. The second crimp member 1028 can comprise one or more complementary apertures 1027 formed on or attached on to the boring element 919. Placing the second crimp member 1028 over the first crimp member 1024 effectively creates an interference fit, interlocking the two members and reduces the risk of loosening, for example, by wedging the drive shaft to the boring element. While in the illustrated embodiments the first crimp member 1024 comprises one or more raised surfaces 1025 and the second crimp member 1028 comprises one or more receiving apertures 1027, in other embodiments, the raised surfaces 1025 could be on the second crimp member 1028 and the receiving apertures 1027 can be located on the first crimp member 1024. In some embodiments, the raised surfaces 1025 and apertures 1027 need not necessarily be circular as illustrated, and can be oval, square, rectangular, or other shapes.

In some embodiments, the first crimp member 1024 comprises between two and eight raised surfaces 1025, such as four raised surfaces 1025. The second crimp member 1028 comprises an equal number of complementary apertures 1027 to create a friction fit with the raised surfaces 1025 of the first crimp member 1024. In some embodiments, and as shown in FIG. 23G, the first crimp member 1024 comprises four raised surfaces 1025 arranged in a 2×2 configuration, while the second crimp member 1028 comprises an equal number of complementary apertures 1027 configured similarly to receive and secure the raised surfaces 1025. One skilled in the art will appreciate that the number and configuration of bumps in the first crimp member 1024 and corresponding apertures in the second crimp member 1028 are not limited to those numbers and configurations as described above. For example, it is possible to have ten bumps in a first crimp member 1024 in a 2×5 configuration, and a corresponding number of apertures in the second crimp member 1028, depending on the desired interference fit.

In addition, it is possible to have a crimp 1001 formed of two interlocking members that interlock by means other than a bump and corresponding aperture. For example, the crimp 1001 can comprise a first crimp member formed of a clasp, while the second crimp member is formed of a clasp receiver.

In some embodiments, this procedure for creating a cavity for inserting one or more of the bone cements described above is performed by making an incision in an appropriate location and advancing the distal portion of the steerable and curvable vertebroplasty drill 900 alone or through a lumen in an access cannula to the desired osteotomy site. A number of features of this device minimize the degree of invasiveness required to perform this procedure: While the relatively low-profile diameter of the laser cut tube 902 minimizes the size of the incision required to guide the device to this location, the ability to change the angle of actuation of the drill tip 919 gives the user significant flexibility in determining the surgical approach for the desired location for making the osteotomy. Once the operator has maneuvered the tip of the steerable and curvable vertebroplasty drill 900 to the desired osteotomy site, the operator is then able to drill into the bone and/or other tissue by rotating the drill tip 919 by manually turning the actuation knob 910. The operator can create a cavity therein by drilling multiple holes in the interior of the vertebral body thereby crushing and/or extracting the diseased bone. This can be facilitated through the use of the deflectable distal portion 923 of the tube 902 that enables the user to change the angle of deflection of the drill tip 919 without changing the angle of primary approach and without having to drill multiple holes through the surface of the bone. In this manner, a relatively large cavity can advantageously be created within the bone with only a minimally invasive approach and single entry site. This procedure is depicted in FIGS. 24A-C.

Once a cavity of sufficient size or desired number of bores have been created within the vertebral body or other bone, the operator can then straighten and withdraw the steerable and curvable vertebroplasty drill 900 and introduce a device capable of injecting the desired bone cement or other compound media or device into the cavity as described, for example, elsewhere in the application. In some embodiments, features of the steerable drill 900 can be incorporated with the bone cement delivery elements disclosed herein on a single catheter such that the drill need not be withdrawn prior to infusion of cement media. For example, the steerable and curvable drill as described herein could additionally include a closed cement delivery system with an input port such as a proximal Luer lock and one or more cement delivery lumens within the catheter body separated from the drive shaft and one or more distal exit ports for cement delivery as also described herein.

Figure 24A:
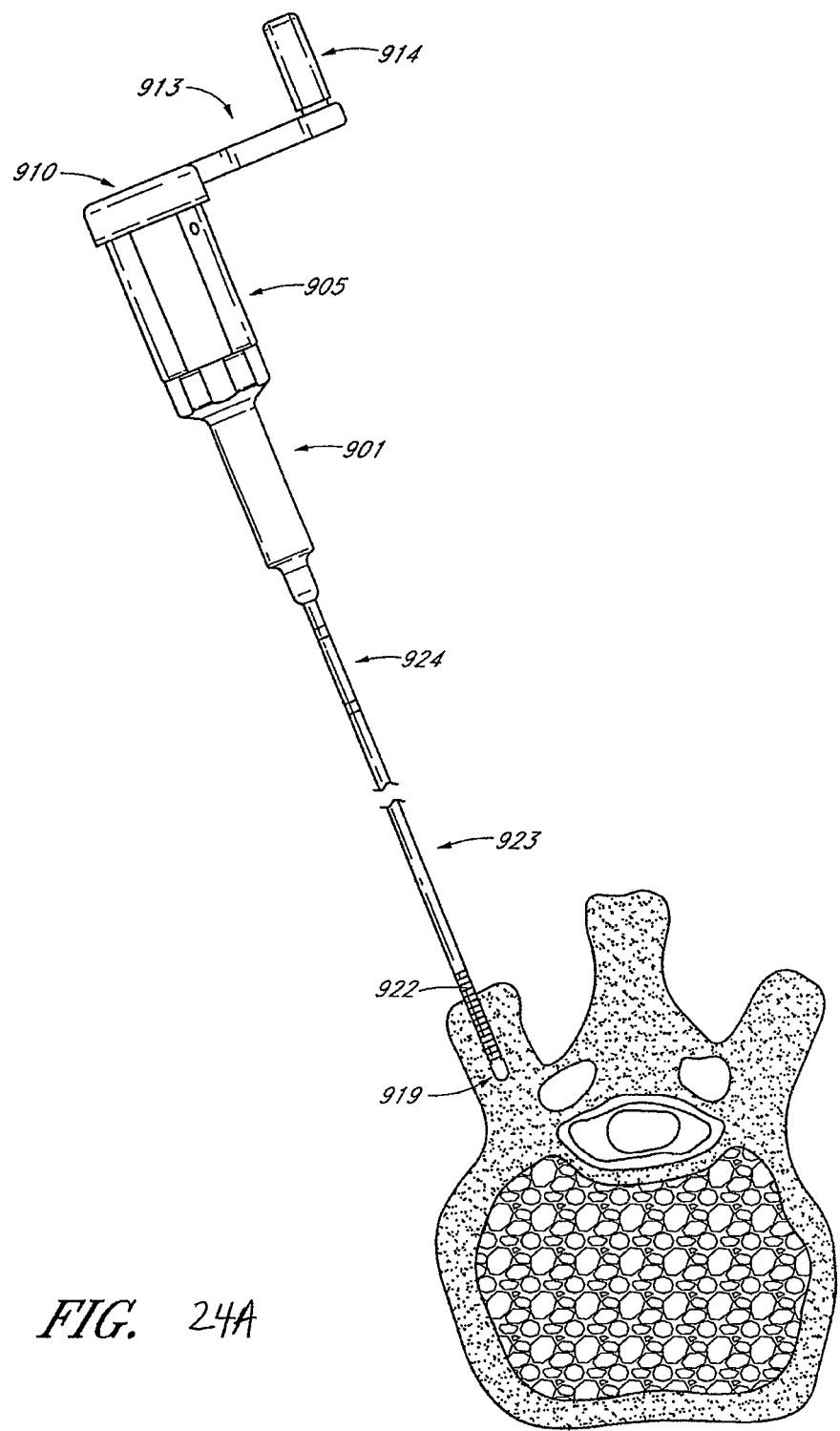
FIGS. 24A through 24C illustrate a method of creating a cavity using the steerable and curvable vertebroplasty drill, according to one embodiment of the invention.
Figure 24B:
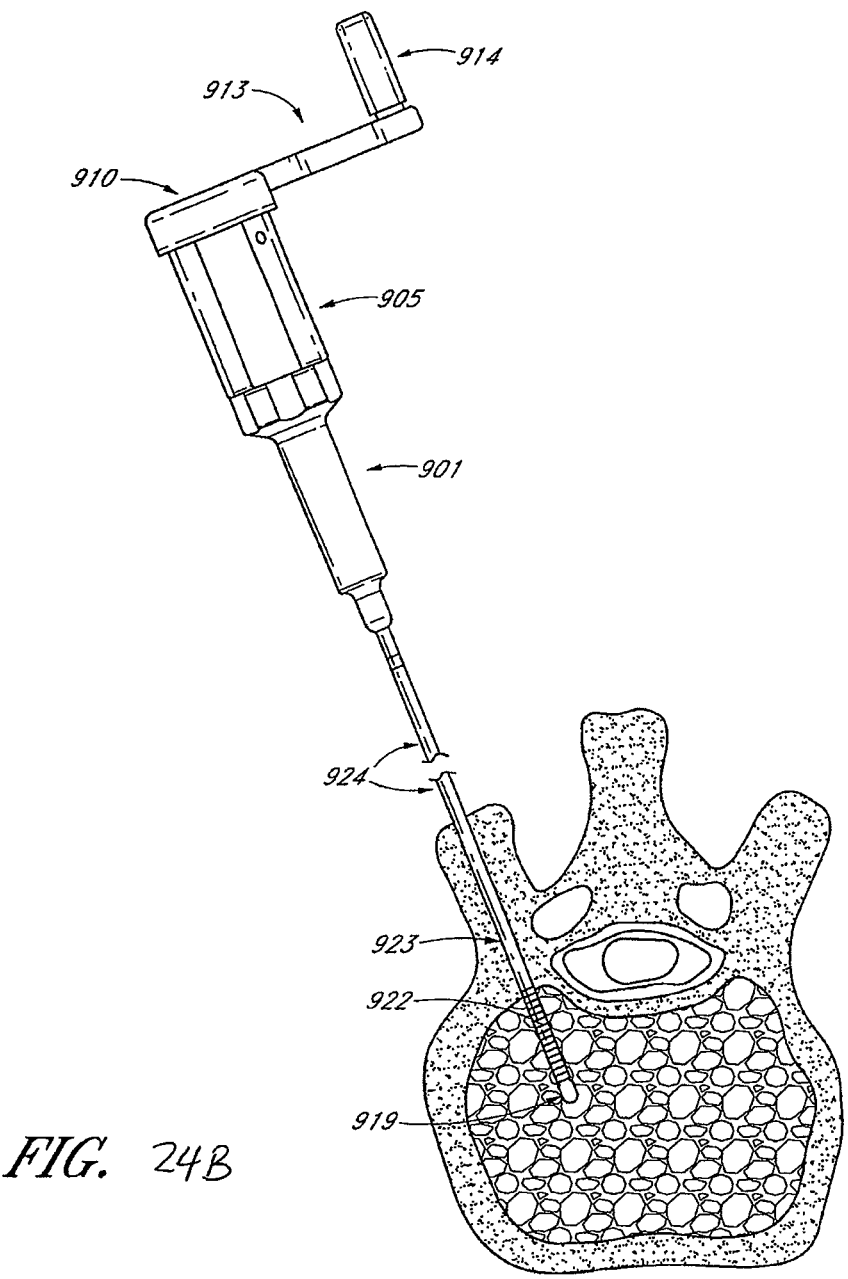
Figure 24C:
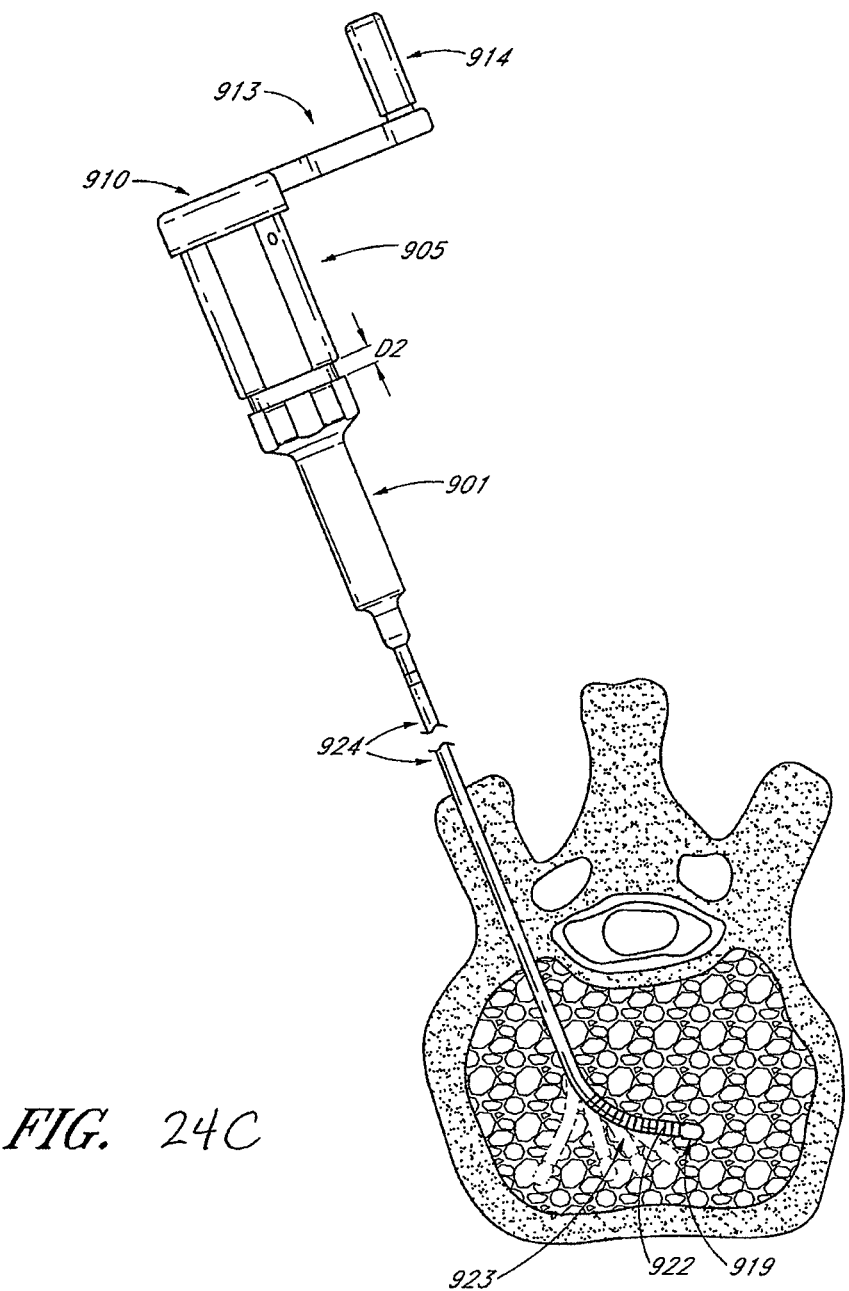
Figure 25A:
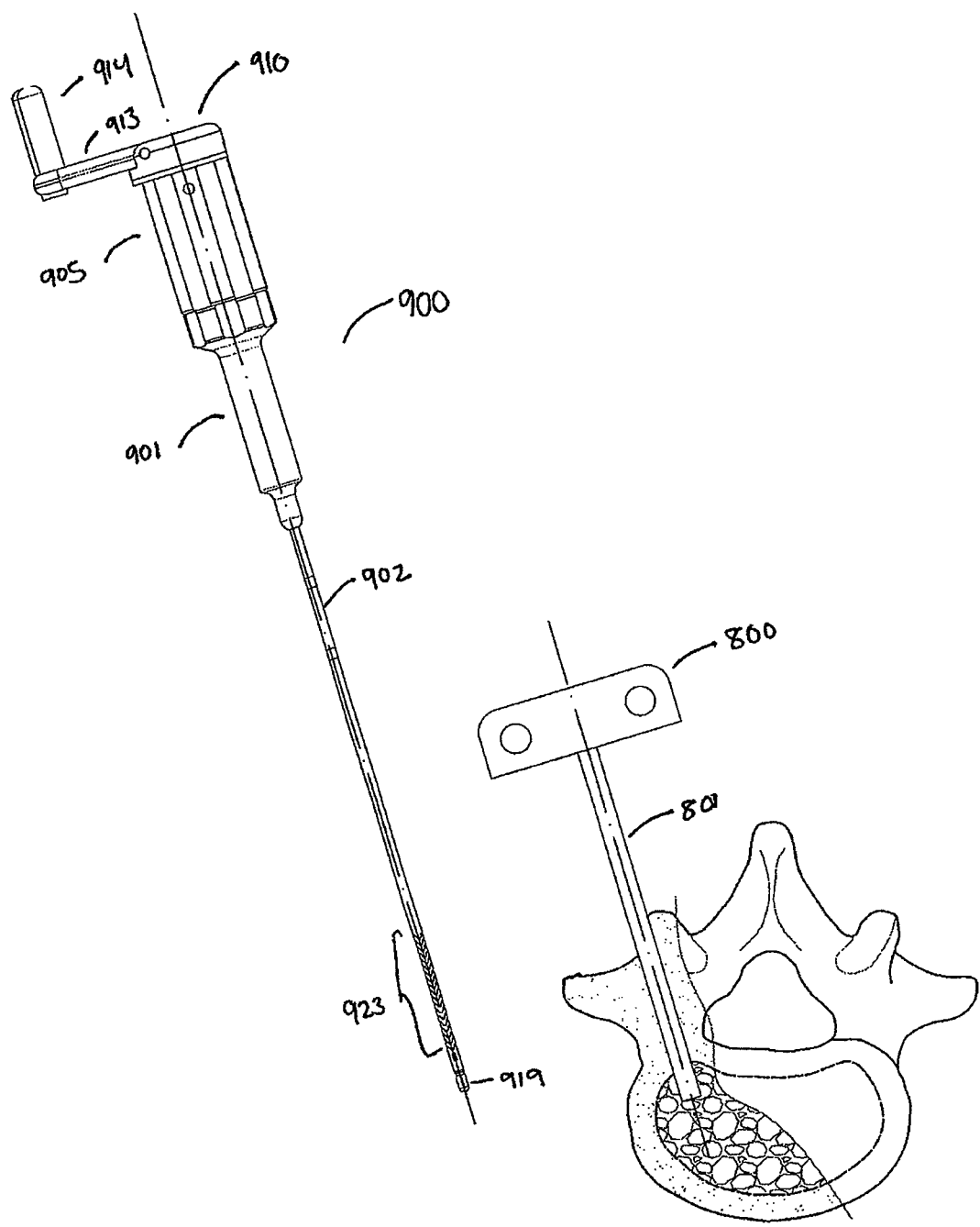
FIGS. 25A through 25C show stages in the method of accomplishing vertebroplasty using a steerable and curvable drill and introducer in accordance with the present invention.
Figure 25B:
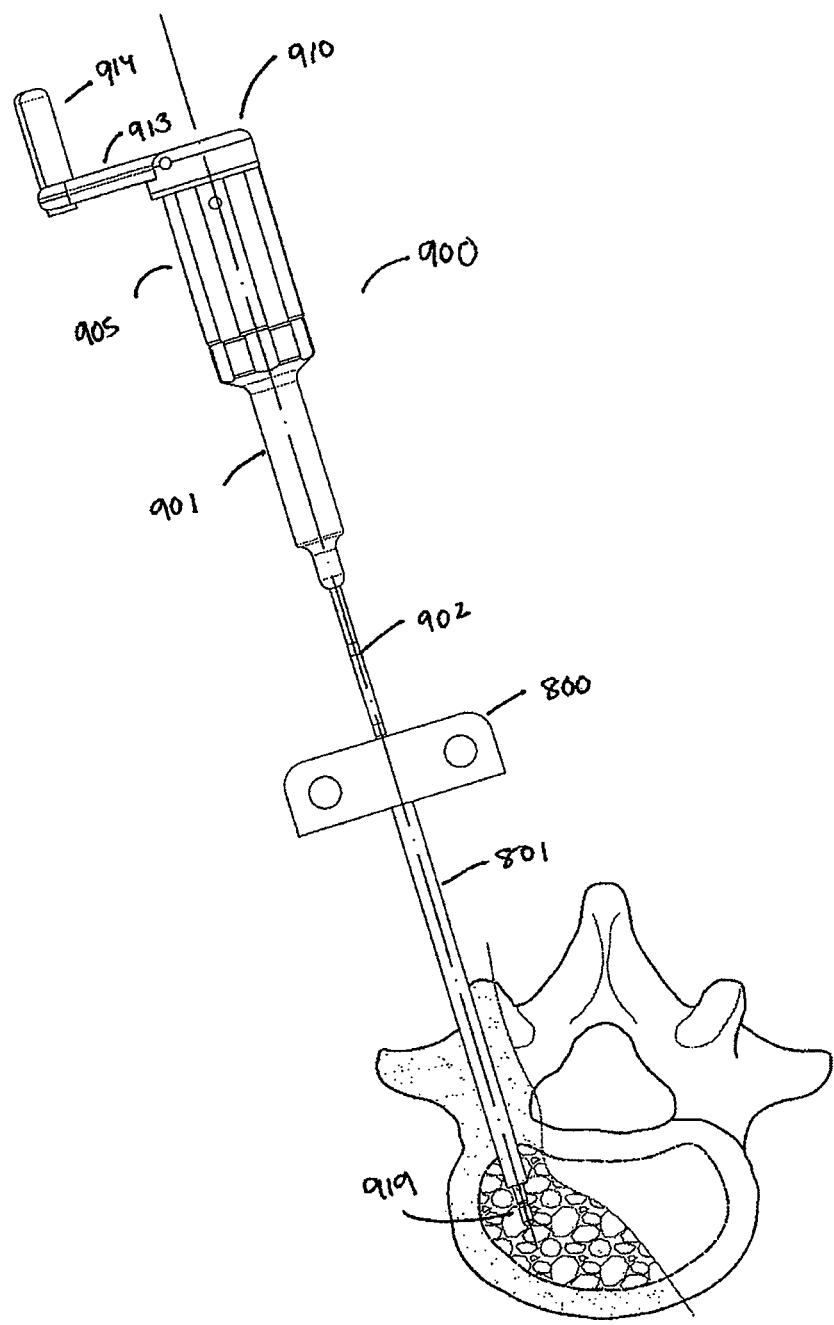
Figure 25C:
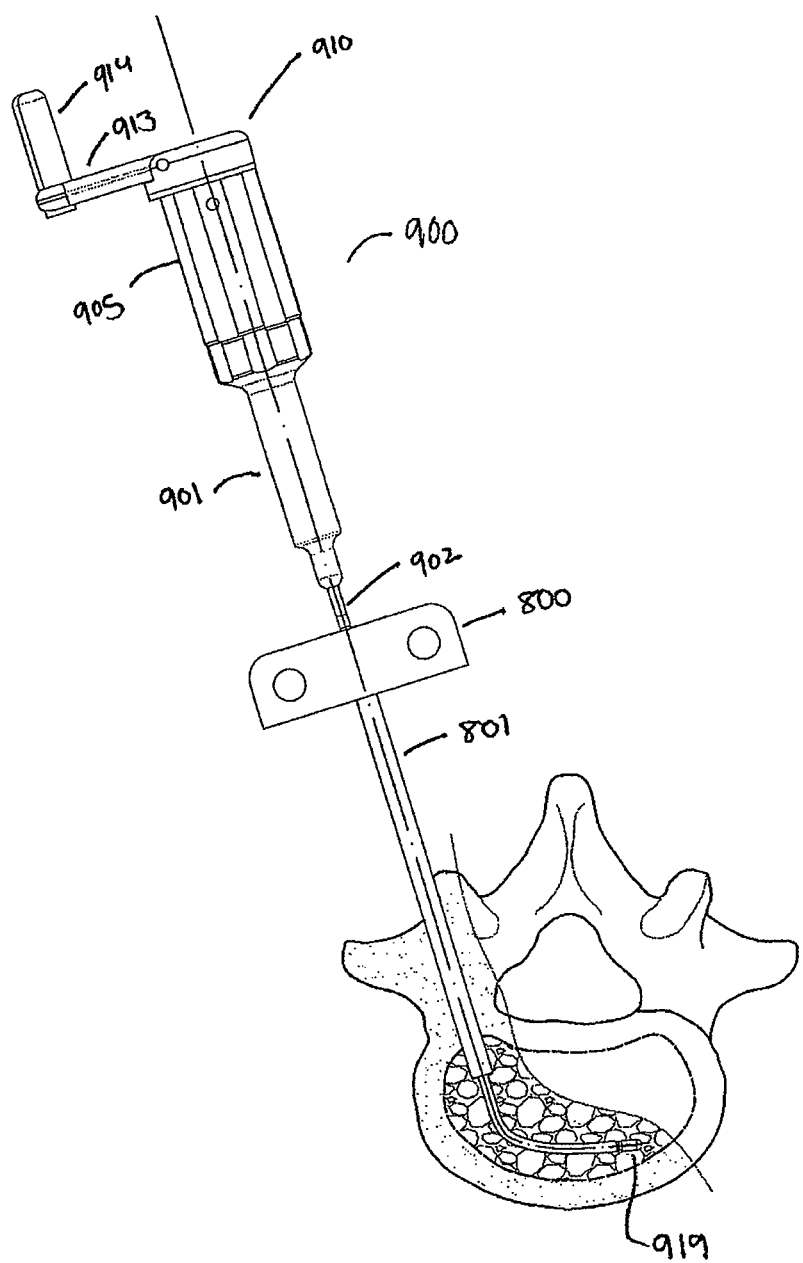

FIGS. 25A through 25C show stages in the method of accomplishing vertebroplasty in one embodiment of the invention, similar to that illustrated in FIGS. 24A through 24C but also illustrating an introducer 800 along with the steerable and curvable drill 900. The introducer 800 includes an elongate tubular body 801 having a lumen therethrough configured to receive the elongate member 902 of the steerable and curvable drill.

In accordance with FIG. 25A, the introducer 800 is first introduced with its distal end positioned to facilitate entry of the drill into the cancellous bone space. The distal end of the introducer 800 can be positioned against or within the cortical bone, or through the cortical bone, and into the cancellous bone space by providing a hole or opening through the cortical bone that surrounds the cancellous bone (e.g., by using a drill bit). In some embodiments, the hole or opening can be provided through a pedicle.

In accordance with FIG. 25B, after the introducer 800 is engaged with the cortical bone, the elongate member 902 of the steerable and curvable drill 900 can be introduced into the lumen of the introducer 800. As shown in FIG. 25B, the distal end of the elongate member 902 carries a boring element 919 (e.g., drill bit), which extends beyond the distal end of the elongate tubular body 801. The boring element 919 can be used to drill and displace portions of cancellous bone in the bone space to prepare the space for the injection of bone material.

In accordance with FIG. 25C, after the elongate member 902 of the steerable and curvable drill 900 has been introduced into the lumen of the introducer 800, the steerable and curvable drill 900 can be steered and directed within the cancellous bone. Actuation of the drill control 914 rotates the drill tip within the cancellous bone, while rotation of the front handle 901 relative to the mid-handle 905 adjusts the curvature of the distal section of the elongate member 902. In some embodiments, the curvature of the distal section of the elongate member 902 can be adjusted via compression or expansion of the helical laser cuts 972, which help to provide the steerable and curvable drill 900 with improved flexibility within the cancellous bone. The steerable and curvable drill 900 can be used to drill and displace cancellous bone in the bone space, thereby forming a cavity within the vertebral body. Once the steerable and curvable drill 900 has formed one or more cavities in the cancellous bone, the steerable and curvable drill 900 can be removed from the introducer 800 and an injection needle (e.g., steerable and curvable injection needle) can be advanced through the introducer 800 to introduce bone cement into the cavity.

Figure 26:
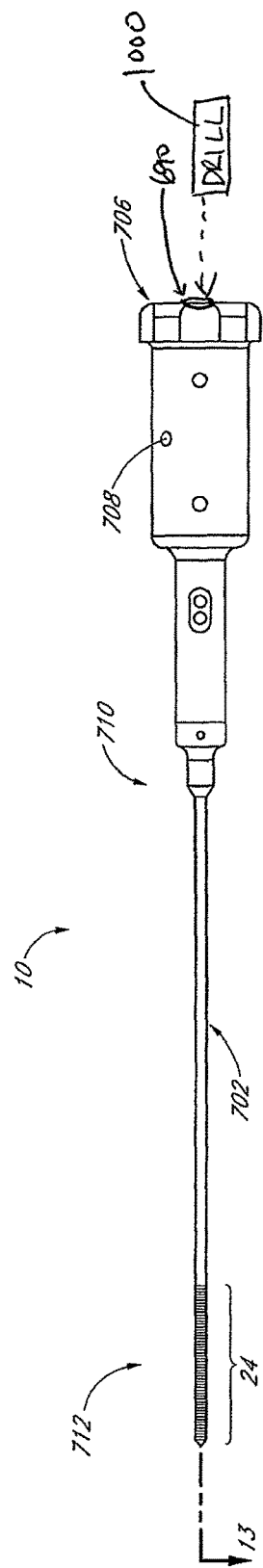
FIG. 26 illustrates a vertebroplasty system including a steerable and curvable injector and a steerable and curvable drill configured to be placed within a lumen of the steerable and curvable injector, according to one embodiment of the invention.

In some embodiments, a vertebroplasty system includes a steerable and curvable drill 1000, and a steerable and curvable injector 10 configured to removably receive the steerable and curvable drill 1000 therethrough. A schematic illustration of such a system is illustrated in FIG. 26. A steerable and curvable injector as illustrated, for example, in FIGS. 4-17B and described in the accompanying text, preferably having a distally facing distal opening, can be inserted into a bone, such as a vertebrae, as illustrated and described in connection with FIGS. 19A-19D. A steerable and curvable drill 1000, such as illustrated in connection with FIGS. 20A-23F, can be inserted, such as via a proximal drill port 690 of the steerable and curvable injector, which can be coaxial with the longitudinal axis of the steerable and curvable injector 10 in some embodiments. The proximal drill port 690 is operably connected to a central lumen which may be the same as, or separate from the lumen for injection media within the steerable and curvable injector 10. The drill lumen terminates distally in a distal exit port that is distally facing in some embodiments. After using the drill 1000 to create a cavity 10, the drill 1000 can be withdrawn from the steerable and curvable injector 10, and media can be introduced into the steerable and curvable injector 10 as illustrated in FIG. 19E.

While described herein primarily in the context of vertebroplasty, one of ordinary skill in the art will appreciate that the disclosed drill can be used or modified in a wide range of clinical applications, such as, for example, other orthopedic applications such as kyphoplasty, treatment of any other bones, pulmonary, cardiovascular, gastrointestinal, gynecological, or genitourinary applications. While this invention has been particularly shown and described with references to embodiments thereof, it will be understood by those skilled in the art that various changes in form and details may be made therein without departing from the scope of the invention. For all of the embodiments described above, the steps of the methods need not be performed sequentially. Additionally, the skilled artisan will recognize that any of the above-described methods can be carried out using any appropriate apparatus. Further, the disclosure herein of any particular feature in connection with an embodiment can be used in all other disclosed embodiments set forth herein. Thus, it is intended that the scope of the present invention herein disclosed should not be limited by the particular disclosed embodiments described above.

What is claimed is:

1. A steerable and curvable vertebroplasty drill, comprising:
    an elongate tubular body having a proximal end, a distal end, and a central lumen extending therethrough, wherein the elongate tubular body has a deflectable zone on the distal end of the elongate tubular body, and wherein the elongate tubular body includes a plurality of transverse slots in the deflectable zone;
    a handle on the proximal end of the tubular body, the handle comprising a deflection control for deflecting the deflectable zone on the distal end of the tubular body, wherein the deflection control comprises a mid-handle portion including a mid-handle threaded surface and a front handle portion including a front handle threaded surface, wherein the mid-handle threaded surface and the front handle threaded surface are interconnected with each other;
    a pull wire disposed within the central lumen of the elongate tubular body and a proximal end of the pull wire is operatively connected to the mid-handle portion of the handle between the deflection control and the distal end of the tubular body;
    a drive shaft housed in the central lumen of the tubular body, the drive shaft including proximal portion and a distal portion, wherein the distal portion comprises one or more slit apertures on the surface of the drive shaft, wherein the drive shaft has a central lumen extending therethrough, wherein the driveshaft is configured to rotate relative to the elongate tubular body within the central lumen, and wherein the drive shaft is configured to flex via the slit apertures upon flexing of the deflectable zone of the tubular body;
    a drive bushing disposed within the handle and configured to couple the proximal portion of the driveshaft to the handle such that rotation of the drive bushing rotates the driveshaft about its longitudinal axis while allowing free axial displacement of the entire driveshaft relative to the drive bushing upon flexing of the deflectable zone of the tubular body;
    an actuator coupled to the handle and operably coupled to the drive bushing, wherein rotation of the actuator is configured to rotate the drive bushing and the driveshaft about its longitudinal axis, and is configured to rotate the mid-handle portion relative to the front handle portion to displace the mid-handle portion axially relative to the front handle portion to change a distance between the mid-handle portion and the front handle portion so as to change the amount of tension on the pull wire thereby changing deflection of the deflectable zone of the tubular body;
    a boring member operatively coupled to the distal portion of the drive shaft configured to drill into bone; and
    an insertable wire insertable through the central lumen of the drive shaft and configured to provide radial support to the distal portion of the drive shaft having the one or more slit apertures; and
    wherein the drive shaft has a cross-sectional shape other than circular, and wherein the drive bushing comprises a through lumen with a complementary shape to the cross-sectional shape of the driveshaft, and wherein the drive shaft is disposed in the through lumen through of the drive bushing.

2. The steerable and curvable vertebroplasty drill of claim 1, wherein the slit apertures are helical.

3. The steerable and curvable vertebroplasty drill of claim 2, wherein a pitch of the slit apertures is between 0.055" and 0.075".

4. The steerable and curvable vertebroplasty drill of claim 1, wherein the transverse slots in the elongate tubular body comprise chevrons.

5. The steerable and curvable vertebroplasty drill of claim 1, wherein the insertable wire is comprised of Nitinol.

6. The steerable and curvable vertebroplasty drill of claim 1, further comprising a limit disposed proximally up the drive shaft from the distal portion of the drive shaft, wherein the limit is configured to provide a proximal stop for preventing the insertable wire from travelling proximally up the drive shaft beyond the limit.

7. The steerable and curvable vertebroplasty drill of claim 1, wherein the drive shaft is coupled to the boring member with a first interlocking member disposed on the distal portion of the drive shaft, and a second interlocking member disposed on the boring member to form a single continuous body between the drive shaft and the boring member.

8. The steerable and curvable vertebroplasty drill of claim 7, wherein the first interlocking member comprises a plurality of raised surfaces, and the second interlocking member comprises a plurality of apertures for receiving the raised surfaces.

9. The steerable and curvable vertebroplasty drill of claim 1, further comprising a drill control on the handle configured to rotate the drive shaft, the drive bushing and the boring member.

10. The steerable and curvable vertebroplasty drill of claim 9, wherein the drill control comprises a rotatable lever.

11. The steerable and curvable vertebroplasty drill of claim 9, wherein the deflection control is disposed on a distal portion of the handle and the drill control is disposed on a proximal portion of the handle.

12. The steerable and curvable vertebroplasty drill of claim 11, wherein the deflection control comprises a mid-handle portion and a front handle portion, and wherein the front handle and the mid-handle are configured to rotate relative to one another to retract the pull wire to deflect the deflectable zone.

13. The steerable and curvable vertebroplasty drill of claim 1, wherein the one or more slit apertures extend between 10 and 30 percent of an entire length of the drive shaft.

* * * * *

UNITED STATES PATENT AND TRADEMARK OFFICE
CERTIFICATE OF CORRECTION

PATENT NO. : 10,292,719 B2
APPLICATION NO. : 14/139372
DATED : May 21, 2019
INVENTOR(S) : Burger et al.

Page 1 of 1

It is certified that error appears in the above-identified patent and that said Letters Patent is hereby corrected as shown below:

In the Claims

Column 34, Line 11 reads, "...the drive shaft including proximal..." which should read, "...the drive shaft including a proximal..."

Column 34, Line 48 reads, "...the through lumen through of..." which should read, "...the through lumen of..."

Signed and Sealed this
Twelfth Day of November, 2019

Andrei Iancu
*Director of the United States Patent and Trademark Office*